(12) United States Patent
MacKinnon

(10) Patent No.: US 9,134,323 B2
(45) Date of Patent: Sep. 15, 2015

(54) ANTIBODY THAT SPECIFICALLY BINDS TO AN EPITOPE IN THE TUREET REGION OF A HUMAN KIR CHANNEL

(75) Inventor: Roderick MacKinnon, New York, NY (US)

(73) Assignee: The Rockefeller University, New York, NY (US)

( * ) Notice: Subject to any disclaimer, the term of this patent is extended or adjusted under 35 U.S.C. 154(b) by 275 days.

(21) Appl. No.: 13/513,105

(22) PCT Filed: Nov. 30, 2010

(86) PCT No.: PCT/US2010/058415
§ 371 (c)(1),
(2), (4) Date: Oct. 15, 2012

(87) PCT Pub. No.: WO2011/068801
PCT Pub. Date: Jun. 9, 2011

(65) Prior Publication Data
US 2013/0035475 A1     Feb. 7, 2013

Related U.S. Application Data

(60) Provisional application No. 61/283,317, filed on Dec. 1, 2009.

(51) Int. Cl.
| | | |
|---|---|---|
| *A61K 39/395* | (2006.01) | |
| *C12P 21/08* | (2006.01) | |
| *C07K 16/00* | (2006.01) | |
| *G01N 33/68* | (2006.01) | |
| *G01N 33/566* | (2006.01) | |

(52) U.S. Cl.
CPC .......... *G01N 33/6893* (2013.01); *G01N 33/566* (2013.01); *G01N 33/6872* (2013.01); *G01N 2800/042* (2013.01); *G01N 2800/2857* (2013.01); *G01N 2800/321* (2013.01); *G01N 2800/326* (2013.01)

(58) Field of Classification Search
None
See application file for complete search history.

(56) References Cited

U.S. PATENT DOCUMENTS

| | | | |
|---|---|---|---|
| 5,637,459 A | 6/1997 | Burke et al. | |
| 5,595,877 A | 10/1997 | Gold et al. | |
| 6,030,776 A | 2/2000 | Eaton et al. | |
| 6,051,698 A | 4/2000 | Janjic et al. | |
| 6,130,364 A | 10/2000 | Jakobovits et al. | |
| 6,180,377 B1 | 1/2001 | Morgan et al. | |
| 6,191,254 B1 | 2/2001 | Falla et al. | |
| 6,641,997 B1 | 11/2003 | MacKinnon | |
| 6,680,377 B1 | 1/2004 | Stanton et al. | |
| 6,979,572 B1 | 12/2005 | Lu | |
| 7,390,884 B2 | 6/2008 | Segal et al. | |
| 7,390,887 B2 | 6/2008 | Goddard et al. | |
| 7,629,171 B2 | 12/2009 | Meagher et al. | |
| 2004/0048369 A1 | 3/2004 | Lu | |
| 2004/0235091 A1 | 11/2004 | Altman | |
| 2005/0272093 A1 | 12/2005 | MacKinnon | |
| 2007/0031924 A1 | 2/2007 | Li et al. | |
| 2007/0172815 A1 | 7/2007 | Weaver | |
| 2009/0155779 A1 | 6/2009 | Sreevatsan et al. | |

OTHER PUBLICATIONS

Ackerman et al., "Ion channels—basic science and clinical disease." 1997, New Engl. J. Med. 336:1575-1595.
Asmar-Rovira et al., "Biophysical and ion channel functional characterization of the Torpedo californica nicotinic acetylcholine receptor in varying detergent-lipid environments." 2008, J. Membrane Biol 223:13-26.
Beck et al., "Strategies and Challenges for the Next Generation of Therapeutic Antibodies." 2010, Nature Rev. Immuno. 10:345-352.
Brunger et al., "Crystallography & NMR System: A New Software Suite for Macromolecular Structure Determination." 1998, Acta Cryst. D54:905-21.
Bunka and Stockley, "Aptamers come of age—at last" 2006, Nat Rev Microbio. 4(8): 588-96.
Cho et al., "Two Critical Cysteine Residues Implicated in Disulfide Bond Formation and Proper Folding of Kir2.1" 2000, Biochemistry 39:4649-57.
Dibb et al., "Molecular basis of ion selectivity, block, and rectification of the inward rectifier Kir3.1/Kir3.4 K(+) channel." 2003, J Biol Chem 278:49537-48.
Fakler et al., "A structural determinant of differential sensitivity of cloned inward rectifier K+ channels to intracellular spermine." 1994, FEBS Lett 356:199-203.
Fakler et al., "Kir2.1 inward rectifier K+ channels are regulated independently by protein kinases and ATP hydrolysis." 1994, Neuron 13:1413-20.
Fan and Makielski, "Anionic phospholipids activate ATP-sensitive potassium channels." 1997, J Biol Chem 272:5388-95.
Felix et al., "Characterization of Kir1.1 channels with the use of a radiolabeled derivative of tertiapin." 2006, Biochemistry 45:10129-39.
Fujiwara and Kubo, "Functional roles of charged amino acid residues on the wall of the cytoplasmic pore of Kir2.1." 2006, J Gen Physiol 127:401-19.

(Continued)

*Primary Examiner* — Christine J Saoud
*Assistant Examiner* — Jon M Lockard
(74) *Attorney, Agent, or Firm* — Riverside Law LLP

(57) ABSTRACT

Methods for identifying compounds that modulate the ion channel activity of a Kir channel are provided. Methods for identifying compounds that selectively modulate the ion channel activity of specific types of Kir channels based on the turret region of a Kir channel are also provided. Methods for identifying compounds to treat conditions associated with abnormal ion channel activity are also provided. Compounds including purified antibodies and methods of making antibodies which bind to the turret region of a Kir channel are provided. Purified polypeptides including at least a portion of the turret region of a Kir channel and nucleic acid sequences encoding these polypeptides are also provided.

11 Claims, 16 Drawing Sheets

(56) References Cited

OTHER PUBLICATIONS

Garcia et al., "Scorpion toxins as tools for studying potassium channels." 1999, Methods Enzymol 294:624-39.
Guo and Lu, "Interaction mechanisms between polyamines and IRK1 inward rectifier K+ channels." 2003, J Gen Physiol 122:485-500.
Guo and Lu, "Kinetics of inward-rectifier K+ channel block by quaternary alkylammonium ions. dimension and properties of the inner pore." 2001, J Gen Physiol 117:395-406.
Guo and Lu, "Mechanism of IRK1 channel block by intracellular polyamines." 2000, J Gen Physiol 115:799-814.
Guo et al., "Mechanism of rectification in inward-rectifier K+ channels." 2003, J Gen Physiol 121:261-75.
Hagiwara and Yoshii, "Effects of internal potassium and sodium on the anomalous rectification of the starfish egg as examined by internal perfusion." 1979, J Physiol 292:251-65.
Harvey et al., "Dendrotoxins: Structure-activity relationships and effects on potassium ion channels." 2004, Curr Med Chem 11:3065-72.
Henry et al., "Protein kinase C inhibition of cloned inward rectifier (HRK1/KIR2.3) K+ channels expressed in Xenopus oocytes." 1996, J Physiol 495( Pt 3):681-8.
Hodgkin and Horowicz, "The influence of potassium and chloride ions on the membrane potential of single muscle fibres." 1959, J Physiol 148:127-60.
Huang et al., "Direct activation of inward rectifier potassium channels by PIP2 and its stabilization by Gbetagamma." 1998, Nature 391:803-6.
Hufton et al., "Phage display of cDNA repertoires: The pVI display system and its applications for the selection of immunogenic ligands."1999, J. Immunol. Methods 231 (1-2):39-51.
Imredy, et al., "A snake toxin inhibitor of inward rectifier potassium channel ROMK1." 1998, BioChemistry 37:14867-74.
Jakobovits et al., "Analysis of homozygous mutant chimeric mice: Deletion of the immunoglobulin heavy-chain joining region blocks B-cell development and antibody production." 1993, Proc. Natl. Acad. Sci. USA, 90:2551-2555.
Jakobovits et al., "Germ-line transmission and expression of a human-derived yeast artificial chromosome." 1993, Nature, 362:255 258.
Jiang et al., "The open pore conformation of potassium channels." 2002, Nature 417:523-6.
Jin and Lu, "A novel high-affinity inhibitor for inward-rectifier K+ channels." 1998, Biochemistry 37:13291.
Jin et al., "Mechanisms of inward-rectifier K+ channel inhibition by tertiapin-Q." 1999, Biochemistry 38:14294-301.
Jones et al., "Improved methods for building protein models in electron density maps and the location of errors in these models." 1991, Acta Cryst. A47:110-119.
Kaczorowski et al., "Ion channels as drug targets: The next GPCRs," 2008, J Gen Physiol 131(5):399-405.
Kehoe and Kay "Filamentous phage display in the new millennium". 2005, Chem. Rev. 105(11):4056-4072.
Kovoor et al., "Evaluation of the role of l(KACh) in atrial fibrillation using a mouse knockout model." 2001, JACC 37:2136-2143.
Kubo and Murata, "Control of rectification and permeation by two distinct sites after the second transmembrane region in Kir2.1 K+ channel." 2001, J Physiol 531(Pt 3):645-60.
Kubo et al., "International Union of Pharmacology. LIV. Nomenclature and molecular relationships of inwardly rectifying potassium channels." 2005, Pharmacological Rev., 57:509-526.
Kuo et al., "Crystal structure of the potassium channel KirBac1.1 in the closed state." 2003, Science 300:1922-6.
Kurata et al., "The role of the cytoplasmic pore in inward rectification of Kir2.1 channels." 2007, J Gen Physiol 130(2):145-55.
Leech and Stanfield, "Inward rectification in frog skeletal muscle fibres and its dependence on membrane potential and external potassium." 1981, J Physiol 319:295-309.

Leyland et al., "The possible role of a disulphide bond in forming functional Kir2.1 potassium channels." 1999, Pflugers Arch 438:778-81.
Liu et al., "Comparison of cloned Kir2 channels with native inward rectifier K+ channels from guinea-pig cardiomyocytes." 2001, J Physiol 532:115-26.
Long et al., "Atomic structure of a voltage-dependent K+ channel in a lipid membrane-like environment." 2007,Nature 450:376-82.
Long et al., "Crystal structure of a mammalian voltage-dependent Shaker family K+ channel." 2005, Science 309:897-903.
Lopes et al., "Alterations in conserved Kir channel-PIP2 interactions underlie channelopathies." 2002, Neuron 34:933-44.
Lu and MacKinnon, "Electrostatic tuning of Mg2+ affinity in an inward-rectifier K+ channel." 1994, Nature 371:243-6.
Lu and MacKinnon, "Purification, characterization, and synthesis of an inward-rectifier K+ channel inhibitor from scorpion venom." 1997 Biochemistry 36(23):6936-6940.
Lu, "Mechanism of rectification in inward-rectifier K+ channels." 2004, Annu Rev Physiol 66:103-29.
Lunder et al., "Comparison of bacterial and phage display peptide libraries in search of target-binding motif". 2005, Appl. Biochem. Biotechnol. 127 (2):125-31.
Lunder et al., "Peptide inhibitor of pancreatic lipase selected by phage display using different elution strategies". 2005, J. Lipid Res. 46 (7):1512-6.
Namba et al., "Kir2.2v: A possible negative regulator of the inwardly rectifying K+ channel Kir2.2." 1996 FEBS Letters 386:211-214.
Nichols and Lopatin, "Inward rectifier potassium channels." 1997, Annu Rev Physiol 59:171-91.
Nishida et al., "Crystal structure of a Kir3.1-prokaryotic Kir channel chimera." 2007, EMBO 26:4005-4015.
Noble and Tsien, "The kinetics and rectifier properties of the slow potassium current in cardiac Purkinje fibres." 1968, J Physiol 195:185-214.
Oliver et al., "Interaction of permeant and blocking ions in cloned inward-rectifier K+ channels." 1998, Biophys J 74:2318-26.
Pearson and Nichols, "Block of the Kir2.1 channel pore by alkylamine analogues of endogenous polyamines." 1998, J Gen Physiol 112:351.
Pegan et al., "Andersen's syndrome mutation effects on the structure and assembly of the cytoplasmic domains of Kir2.1." 2006, Biochemistry 45:8599-606.
Pegan et al., "Cytoplasmic domain structures of Kir2.1 and Kir3.1 show sites for modulating gating and rectification." 2005, Nat Neurosci 8:279-87.
Ramu et al., "Short variable sequence acquired in evolution enables selective inhibition of various inward-rectifier K+ channels." 2004, Biochemistry 43:10701-9.
Ramu, et al. Engineered specific and high affinity inhibitor for a subtype of inward rectifier Kir channels 2008, Proc. Nat'l Acid Sci USA 105:10774-10778.
Schulze et al., "Phosphatidylinositol 4,5-Bisphosphate (PIP2) Modulation of ATP and pH Sensitivity in Kir Channels: A Tale of an Active and a Silent PIP2 Site in the N Terminus" 2003, J Biol Chem 278:10500-5.
Shin and Lu, "Mechanism of the voltage sensitivity of IRK1 inward-rectifier K+ channel block by the polyamine spermine." 2005, J Gen Physiol 125:413-26.
Shin et al., "Evidence for sequential ion-binding loci along the inner pore of the IRK1 inward-rectifier K+ channel." 2005, J Gen Physiol 126:123-35.
Shyng, et al., "Structural determinants of PIP(2) regulation of inward rectifier K(ATP) channels." 2000, J Gen Physiol 116:599-608.
Smith , GP. "Filamentous fusion phage: Novel expression vectors that display cloned antigens on the virion surface". 1985, Science 288 (4705):1315-1317.
Smith and Petrenko, "Phage display". 1997, Chem. Rev. 97 (2):391-410.
Soom et al., "Multiple PIP2 binding sites in Kir2.1 inwardly rectifying potassium channels." 2001, FEBS Lett 490(1-2):49-53.
Spassova and Lu, "Coupled ion movement underlies rectification in an inward-rectifier K+ channel." 1998, J Gen Physiol 112:211-21.

(56) References Cited

OTHER PUBLICATIONS

Spassova and Lu, "Tuning the voltage dependence of tetraethylammonium block with permeant ions in an inward-rectifier K+ channel." 1999, J Gen Physiol 114:415-26.

Stanfield et al., "A single aspartate residue is involved in both intrinsic gating and blockage by Mg2+ of the inward rectifier, IRK1." 1994, J Physiol 478( Pt 1):1-6.

Stanfield, et al., "Constitutively active and G-protein coupled inward rectifier K+ channels: Kir2.0 and Kir3.0." 2002, Rev.Physiol Biochem.Pharmacol. 145:47-179.

Swartz and MacKinnon, "An inhibitor of the Kv2.1 potassium channel isolated from the venom of a Chilean tarantula." 1995, Neuron 15:941-9.

Taglialatela et al., "C-terminus determinants for Mg2+ and polyamine block of the inward rectifier K+ channel IRK1." 1995, EMBO J 14:5532-41.

Takahashi et al., "Molecular Cloning and Functional Expression of cDNA Encoding a Second Class of Inward Rectifier Potassium Channels in the Mouse Brain." 1994, J Biol Chem 269:23274-79.

Tao et al., "Crystal Structure of the Eukaryotic Strong Inward-Rectifier K+ Channel Kir2.2 at 3.1 A Resolution" 2009, Science 326(5960)1668-74.

Vagin and Teplyakov, "An approach to multi-copy search in molecular replacement." 2000, Acta Cryst. 56(Pt 12):1622-4.

Wible et al., "Gating of inwardly rectifying K+ channels localized to a single negatively charged residue." 1994, Nature 371:246-9.

Wong, et al., "A carboxy-terminal affinity tag for the purification and mass spectrometric characterization of integral membrane proteins." 2009, J Proteome Res 8:2388-96.

Yang et al., "Control of rectification and permeation by residues in two distinct domains in an inward rectifier K+ channel", 1995, Neuron 14:1047-54.

Yang, et al., "Stabilization of ion selectivity filter by pore loop ion pairs in an inwardly rectifying potassium channel." 1997, Proc Natl Acad Sci U S A 94:1568-72.

Zeng, et al., "Structural determinants and specificities for ROMK1-phosphoinositide interaction." 2002, Am J Physiol Renal Physiol 282:F826-34.

Zhang et al., "Activation of inwardly rectifying K+ channels by distinct PtdIns(4,5)P2 interactions." 1999, Nat Cell Biol 1:183-8.

Zhou and MacKinnon, "Ion binding affinity in the cavity of the KcsA potassium channel." 2004, Biochemistry 43:4978-82.

Zhou et al., "Chemistry of ion coordination and hydration revealed by a K+ channel-Fab complex at 2.0 A resolution." 2001, Nature 414:43-48.

FIG. 1A

```
                     βA                       Interfacial helix          Outer helix
                                                      αA              αB
cKir2.2    RRLCRNRFVKKNGQCNVEFTNMDDKPQR--YIADMFTTCVDIRWRYMLLLFSLAFLVSWLL    96
hKir2.2    RRRCRNRFVKKNGQCNIEFANMDEKSQR--YLADMFTTCVDIRWRYMLLIFSLAFLASWLL    97
hKir2.1    RQQCRSRFVKKDGHCNVQFINVGEKGQR--YLADIFTTCVDIRWRWMLVIFCLAFVLSWLF    98
hKir1.1    HSRQRARLVSKDGRCNIEFGNVEAQSRFIFFVDIWTTVLDLKWRYKMTIFITAFLGSWFF    94
hKir3.1    PKKKRQRFVDKNGRCNVQHGNLGSETSRI-YLSDLFTTLVDLKWRNLFIFILTYTVAWLF    97
hKir3.4    GKKPRQRYMEKSGKCNVHHGNV-QETYRL-YLSDLFTTLVDLKWRFNLLVFTMVYTVTWLF   103
hKir6.1    DRLPKARFIAKSGACNLAHKNI-REQGRL-FLQDIFTTLVDLKWRHTLVIFTMSFLCSWLL    86
hKir7.1    LSQRYRRMVTKDGHSTLQMDGA--QRGLAYLRDAWGILMDMRWRWMMLVFSASFVVHWLV    70
KirBac1.1  SPARKPPRGGRRIWSGTREVIAYGMPASVWR-DLYYWALKVSWPVFFASLAALFVVNNTL    77
KcsA       -------------------------------MAPMLSGLLARLVKLLLGRHGSALHWRAAGAATVLLVIVLLAG    43
rKv1.2     -----------------------------------------------MRELGLLIFFLFIGVILF         342

αB          310                  αC           Turret       C123         Pore helix         Filter
cKir2.2    FGLIFWLIALIHGDLEN--PGGDDTFK-P----------CVLQVNGFVAAFLFSIETQTTIGYGF    148
hKir2.2    FGIIFWVIAVAHGDLEP-AEGRGR--T-P----------CVMQVHGFMAAFLFSIETQTTIGYGL    148
hKir2.1    FGCVFWLIALLHGDLDASKEGKA-------------CVSEVNSFTAAFLFSIETQTTIGYGF    147
hKir1.1    FGLLWYAVAYIHKDLPEFH-PSA-NHT-P----------CVENINGLTSAFLFFIETEATIGYGY    146
hKir3.1    MASMWWVIAYTRGDLNKAHVG---NYT-P----------CVANVYNFPSAFLFFIETETEATIGYGY    148
hKir3.4    FGFIWWLLIAYIRGDLD--HVG-DQWEI-P----------CVENLSGFVSAFLFSIETETTIGYGF    154
hKir6.1    FAIMWWLVAFAHGDIYAYME-KSGMEKSGLESTVCVTNVRSFTSAFLFSIEVQVTIGFGG    145
hKir7.1    FAVLWYVLAEMNGDLELDHDAPPENHTI---------CVKYITSFTAAFSFLEIQTIGYGT    124
KirBac1.1  FALLYQLGDAPIANQSP---------------------PGFVGAFFFSVETLATVGYGD    115
KcsA       SYLAVLAERGAPGAQLI--------------------TYPRALWWSVETATITVGYGD    80
rKv1.2     SSAVYFAEADERDSQFP--------------------SIPDAFWWAVVSMTTVGYGD    379
```

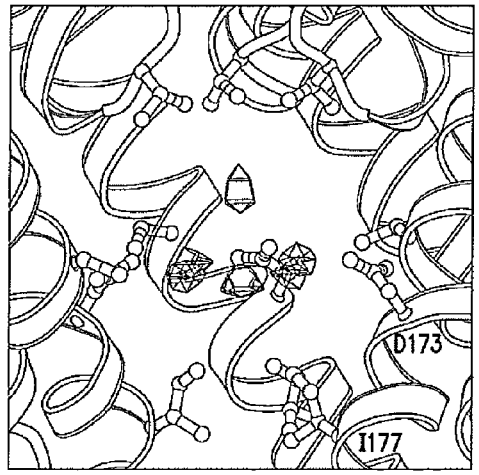 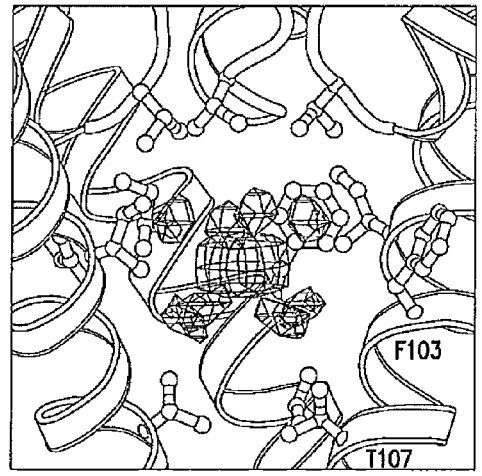
FIG. 3A                    FIG. 3B
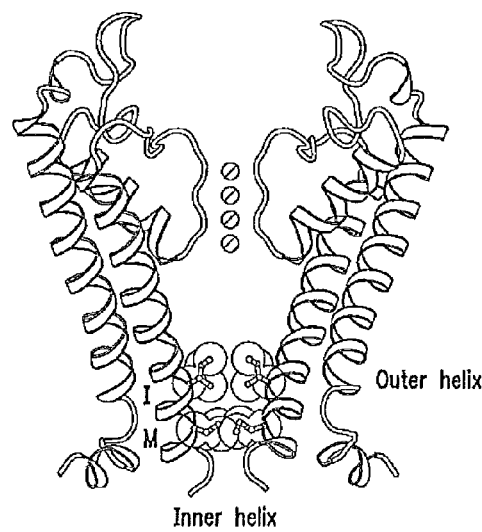 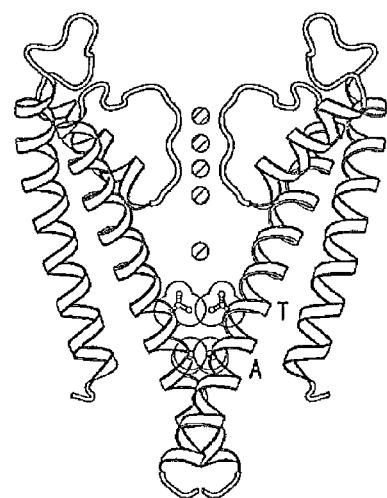
FIG. 3C                    FIG. 3D

FIG. 3E
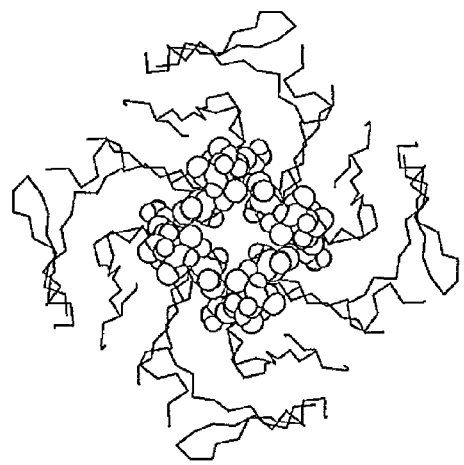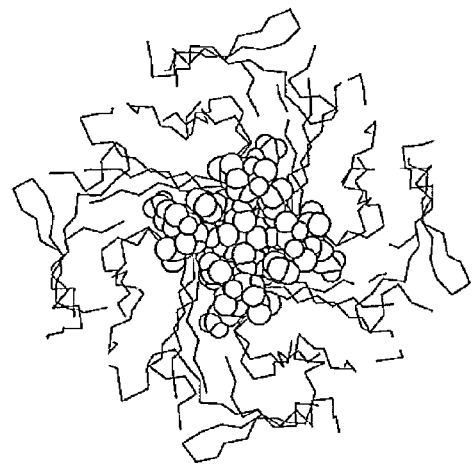
FIG. 3F FIG. 3G

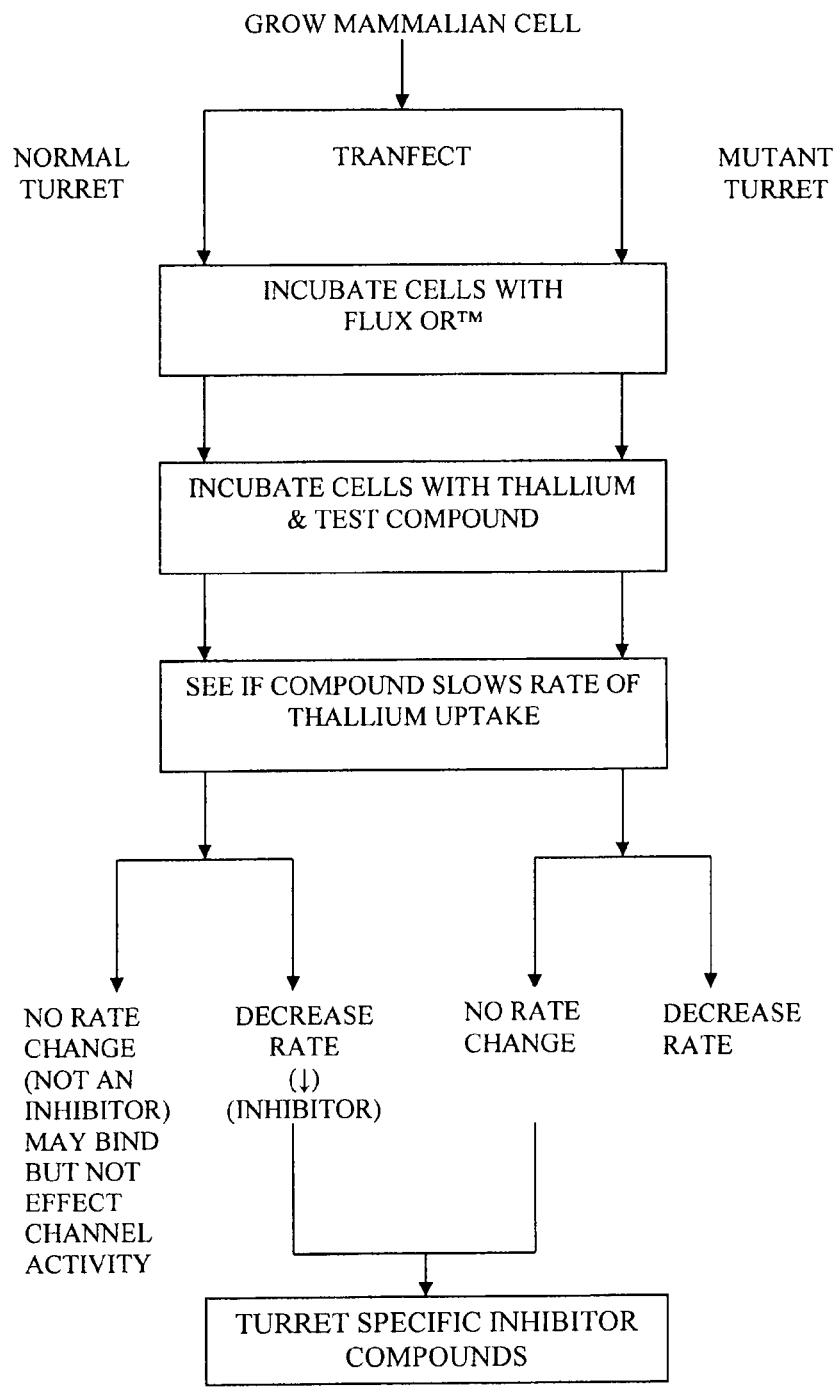

ANTIBODY THAT SPECIFICALLY BINDS TO AN EPITOPE IN THE TUREET REGION OF A HUMAN KIR CHANNEL

CROSS-REFERENCE TO RELATED APPLICATION

This application is the U.S. national phase application filed under 35 U.S.C. §371 claiming benefit to International Patent Application No. PCT/US2010/058415, filed on Nov. 30, 2010, which is entitled to priority under 35 U.S.C. §119(e) to U.S. Provisional Patent Application No. 61/283,317, filed on Dec. 1, 2009, each of which application is hereby incorporated herein by reference in its entirety.

FIELD OF INVENTION

The present invention relates to Kir channel proteins and methods for identifying compounds that modulate ion channel activity by Kir channels. In particular, the present invention relates to identifying compounds which are useful for treating diseases related to the function of Kir channel proteins.

BACKGROUND OF TIE INVENTION

Inward rectifier K+ channels (Kir channel proteins) are involved in the control of many physiological processes that are important to human health. Kir channel proteins normally function as K+ (potassium) selective pores that span cell membranes. The Kir channels are referred to as inward rectifier K+ (Kir) channels based on a fundamental ion conduction property of these channels: given an equal but opposite electrochemical driving force K+ conductance into the cell far exceeds conductance out of the cell.

Among their many functions Kir channel proteins control the pace of the heart, regulate secretion of hormones into the blood stream, generate electrical impulses underlying information transfer in the nervous system and control airway and vascular smooth muscle tone. It is believed that various disease states are directly related to the function of Kir channel proteins. Members of this channel family include Kir1-Kir7, (Kubo et al., Pharmacological Rev., 57:509-526, 2005) Hypertension, atrial fibrillation, and type 2 diabetes are related to Kir channel protein function and are serious conditions for which new therapies are needed. Specific links between Kir channel proteins and disease have been found. Kir1.1 channels are present in the kidney and regulate salt secretion into the urine. Heritable mutations involving Kir1.1 cause Barter's syndrome and hypotension. Compounds which selectively inhibit Kir1.1 have the potential to serve as a new form of anti-hypertensive agent in which hypokalemia, a major side-effect of currently used diuretics, should in principle not be a problem. Thus, hypertensive individuals could benefit from Kir1.1 inhibitor-based therapies. Kir3.1 and Kir3.4 channels, which assemble to form a heteromultimer, are called G-protein-gated K+ channels (GIRK). These channels control heart rate through stimulation by the parasympathetic nervous system. GIRK channel knock-out mice do not develop atrial fibrillation under any of the usual stimuli that induce this arrhythmia in mice. (Claphan et al., JACC 37, 2136-2143 (Jun. 15, 2001)) Accordingly, inhibition of GIRK channels in humans might provide effective treatment for atrial fibrillation. Kir6 channels are expressed in beta cells of the pancreas and control insulin secretion. With the identification of compounds that selectively inhibit the Kir6 channel new therapies could be realized for the treatment of type 2 diabetes. Accordingly, Kir channel proteins are good targets for the treatment of various diseases.

The Kir channel family of proteins are very similar to each other in both sequence and, by inference, structure; thus, it has been very difficult to identify compounds that can specifically modulate one kind of Kir channel protein without cross-reacting with other types of Kir channel proteins.

For the first time the structure of a eukaryotic Kir channel has been determined, and a structural feature "the turret region" has been identified that is highly ordered in structure and, based on the amino acid sequences will differ among Kir channels. Prior to this structure, only the structure of a prokaryotic Kir channel had been determined. (Nishida et al., EMBO, vol. 26, pp. 4005-4015 (2007)) The turret is an important functional region of the protein and faces the outside of the cell making this region an attractive target for identifying potential therapeutic compounds. Given the identification of the turret region in the various Kir channel proteins and the structure in a prototype, the present invention provides a variety of methods by which the turret region may be used to identify compounds having therapeutic utility for treating the various diseases related to the function of Kir channels.

The present invention provides for the first time the expression and purification of a eukaryotic Kir channel as explained in detail below. Study of the structure of this eukaryotic Kir channel resulted in a realization of the importance of the turret region and the invention of methods which allow identification of therapeutic compounds that can selectively bind to different members of the Kir channel family of proteins.

SUMMARY OF THE INVENTION

The present invention relates to methods for identifying a compound that modulates ion channel activity of a Kir channel including identifying a compound which binds the turret region of a Kir channel; and determining if the compound modulates ion channel activity of the Kir channel.

In particular embodiments, the method may be used to identify an antibody that binds the turret region of a Kir channel and modulates the Kir channel's activity. The antibody may be human, chimeric or humanized. The antibody may also be a polyclonal antibody, monoclonal antibody, an intact immunoglobulin molecule, an antibody fragment, a scFv, a Fab, a F(ab)2, a Fv, or a disulfide linked Fv.

In another embodiment, the method may be used to identify suitable nucleic acid molecules that can modulate a Kir channel's activity by binding to its turret region. In such an embodiment, the nucleic acid may be a DNA or RNA molecule. In certain embodiments the nucleic acid is an aptamer. The method may also include identifying a suitable nucleic acid by using in vitro selection techniques.

In another embodiment, the method is used to identify a protein or peptide that can bind a turret region of a Kir channel and modulate the Kir channel. In this embodiment, the protein/peptide may be attached to a protein scaffold or displayed on the surface of a phage.

In another embodiment, the method discussed above is used to screen for small molecules that can modulate Kir channel activity by binding to the Kir channel's turret region.

In any of the methods discussed above, the Kir channel may be a human Kir channel or a chicken/human hybrid Kir channel. Typically, the chicken/human hybrid Kir channel will comprise a human Kir channel turret region.

Various standard biochemical assays may be used to identify whether a compound binds to the turret region of a Kir channel in the method of the present invention. For example, the identifying step may comprise an ELISA and a Western blot to determine if the compound binds to a properly folded Kir channel but not to a denatured Kir channel. Moreover, the identifying step may comprise determining if the compound binds to a Kir channel with a normal turret region but not a mutated turret region.

Regarding the determining whether a compound modulates the activity of a Kir channel, various electrophysiological assays may be used such as two-electrode voltage clamp, patch clamp, and planar lipid bilayer assays. Alternatively or additionally, the determining step may include a fluorescent assay such as one utilizing a thallium specific fluorescent dye.

In another aspect, the present invention relates to a method for identifying a compound that selectively modulates ion channel activity of a specific type of Kir channel including identifying a compound which binds the turret region of a specific type of Kir channel but does not bind to other types of Kir channels; and determining if the compound modulates the activity of the Kir channel.

In another embodiment, the present invention relates to a method of identifying a compound to treat a condition associated with abnormal ion channel activity by a Kir channel including identifying a compound which binds the turret region of a Kir channel; determining if the compound modulates ion channel activity of the Kir channel; and administering the compound which modulates ion channel activity to a subject to determine if the compound is able to treat the condition. In such a method, the condition may be diabetes mellitus, hypertension, cardiac arrhythmia, or epilepsy.

In another aspect, the present invention relates to a purified antibody that specifically binds to an epitope in the turret region of a Kir channel. In this embodiment, the purified antibody may be a polyclonal antibody, a monoclonal antibody, an intact immunoglobulin molecule, an antibody fragment, a scFv, a Fab, a F(ab)2, a Fv, or a disulfide linked Fv. The antibody may specifically bind to a human Kir channel such as a Kir1, Kir2, Kir3, Kir4, Kir5, Kir6, or Kir7 channel. The antibody preferably binds to an epitope within the turret region of a human Kir channel such as Kir1.1, Kir1.2, Kir2.1, Kir2.2, Kir2.3, Kir2.4, Kir3.1, Kir3.4, Kir4.1, Kir4.2, Kir5.1, Kir6.1, or Kir6.2 channel. Even more preferably, the antibody binds to the variable portion of the turret region of a human Kir channel.

In another embodiment, the present invention relates to a method of making an antibody that specifically binds to an epitope in the turret region of a human Kir channel, including providing a chicken/human hybrid Kir channel, wherein the chicken/human hybrid comprises a human Kir channel turret region; immunizing a non-human animal with the chicken/human hybrid Kir channel; and determining whether the antibody is binding to the human Kir channel turret region. In this embodiment, the chicken portion of the chicken/human hybrid Kir channel may be derived from a chicken Kir2.2 channel. Moreover, in this embodiment, the human Kir channel turret region may be derived from Kir1, Kir2, Kir3, Kir4, Kir5, Kir6, or Kir7. Preferably, the human Kir channel turret region is derived from a human Kir1.1, Kir1.2, Kir2.1, Kir2.2, Kir2.3, Kir2.4, Kir3.1, Kir3.4, Kir4.1, Kir4.2, Kir5.1, Kir6.1, or Kir6.2 channel.

In another embodiment, the present invention relates to a method of making an antibody that specifically binds to an epitope in the turret region of a human Kir channel, including providing a human Kir channel; immunizing a non-human animal with the Kir channel; and determining whether the antibody is binding to the human Kir channel turret region.

In another embodiment, the present invention relates to a purified polypeptide that consists of the turret region of human Kir channels such as Kir1.1, Kir1.2, Kir2.1, Kir2.2, Kir2.3, Kir2.4, Kir3.1, Kir3.4, Kir4.1, Kir4.2, Kir5.1, Kir6.1, or Kir6.2. In another aspect, the present invention relates to an isolated nucleic acid comprising a nucleotide sequence that encodes a polypeptide that consists of the turret region of human Kir channels such as Kir1.1, Kir1.2, Kir2.1, Kir2.2, Kir2.3, Kir2.4, Kir3.1, Kir3.4, Kir4.1, Kir4.2, Kir5.1, Kir6.1, or Kir6.2.

BRIEF DESCRIPTION OF THE DRAWINGS

FIG. 1A-1C shows key residues in eukaryotic Kir channels. A sequence alignment of sequences of chicken Kir2.2 (GI:118097849, SEQ ID NO. 18), human Kir2.2 (GI: 23110982, SEQ ID NO. 17), human Kir2.1 (GI:8132301, SEQ ID NO. 16), human Kir1.1 (GI:1352479, SEQ ID NO. 14), human Kir3.1 (GI:1352482, SEQ ID NO. 20), human Kir3.4 (GI:1352484, SEQ ID NO. 21), human Kir6.1 (GI: 2493600, SEQ ID NO. 25), human Kir7.1 (GI:3150184, SEQ ID NO. 27), KirBac1.1 (GI:33357898, SEQ ID NO. 59), KcsA (GI:39654804, SEQ ID NO. 60), and rat Kv1.2 (GI: 73536156, SEQ ID NO. 61) is shown. For all the Kir sequences only the core region corresponding to the expressed protein and atomic structure of Kir2.2 is included in the alignment. For Kv1.2 only the transmembrane pore region is shown. Secondary structure elements are indicated above the sequences and the turret is shown in small dotted lines above the sequence. Residues discussed in the text are boxed in a series of alternating dashes and dots (acidic residues), a series of large dots (two disulfide-bonded cysteines), alternating dashes and pairs of dots (the inner helix bundle activation gate), series of small dashes (conserved residues among the turrets of eukaryotic Kir channels), a series of small dots (the selectivity filter and E139), and a series of large dashes (critical residues for channel-$PIP_2$ interactions).

(FIG. 2A) Stereoview of a ribbon representation of the Kir2.2 tetramer from the side with the extracellular solution above. Four subunits of the channel are shown. Approximate boundaries of the lipid bilayer are shown as bars. (FIG. 2B) A close-up view of the pore-region of a single subunit (in ribbon representation) with the turret, pore helix and selectivity filter labeled. Side chains of residues E139, R149 and a pair of disulfide-bonded cysteines (C123 and C155) are shown as sticks. Ionized hydrogen-bonds are indicated by dashed black lines. The region flanked by the two disulfide-bonded cysteines is stippled. (FIG. 2C) Electron density (wire mesh, $2F_o-F_c$, calculated from 50-3.1 Å using phases from the final model and contoured at 1.0σ) is shown for the side chains of E139 and R149 forming a salt-bridge. (FIG. 2D) (FIG. 2E) $K^+$ selectivity filter of the Kir2.2 channel (FIG. 2 D) compared with that of the Kv1.2-Kv2.1 paddle chimera channel (FIG. 2E, PDB ID 2R9R). For clarity, only two of the four subunits are shown. $K^+$ (cross hatched circles), water molecules (solid spheres), and hydrogen bonds between R149 and E139 (Kir, dashed black lines), or between D379, M380 and waters (Kv, dashed black lines) are shown.

FIG. 3A-3G illustrates the cavity and gates region of a Kir channel. (FIG. 3A) (FIG. 3B) Electron density in the cavity of the Kir2.2 channel (A, $F_o-F_c$ omit map, calculated from 50-3.1 Å using phases from the final model and contoured at 2.0σ) and of the KcsA channel (FIG. 3B, PDB ID 1K4C, $F_o-F_c$ omit map, calculated from 50-3.1 Å using phases from the final model and contoured at 2.8σ). The channels are shown as ribbon representations with the subunit closest to the viewer removed. Only the side chains facing the cavity are shown (sticks). (FIG. 3C) (FIG. 3D) Comparison of the transmembrane inner helix bundle activation gate of Kir2.2 (FIG.

3C) with the KcsA structure (FIG. 3D, PDB ID 1K4C). For clarity, only two of the four subunits (ribbon) are shown. Side chains of the residues in the bundle crossing are shown as sticks and van der Waals surfaces. $K^+$ ions are shown as cross hatched spheres. Inner and Outer helices are indicated. (FIG. 3E) Superposition of the chicken Kir2.2 cytoplasmic domain (α-carbon trace) and the mouse Kir2.1 cytoplasmic domain (α-carbon trace, PDB ID 1U4F) in stereo viewed from the extracellular side. (FIG. 3F) (FIG. 3G) Comparison of the apex (G-loop) of the cytoplasmic pores of Kir2.2 (FIG. 3F) and mouse Kir2.1 (FIG. 3G), with the same view as FIG. 3E. The cytoplasmic domains are shown as α-carbon traces, with residues 303-309 (Kir2.2) and 302-308 (Kir2.1) shown as CPK models.

(FIG. 4A) (FIG. 4B) (FIG. 4C) Electron density (wire mesh) of $Rb^+$ (FIG. 4A, $F_o$-$F_c$ map calculated to 4.0 Å, contoured at 3.5σ for density in the filter and 2.0σ for density elsewhere), $Sr^{2+}$ (FIG. 4B, 10 mM, $F_o$-$F_c$ map calculated to 3.3 Å, contoured at 1.5σ for density in the cavity and 3.0σ for density elsewhere) and $Eu^{3+}$ (FIG. 4C, 10 mM, anomalous difference map calculated to 6.0 Å, contoured at 2.8σ) inside the Kir2.2 channel ion conduction pathway. Kir2.2 is represented as a α-carbon trace with the transmembrane domain and cytoplasmic domain closest to viewer removed for clarity. The ions are shown as spheres. (FIG. 4D) Electron density (200 mM $Sr^{2+}$, $F_o$-$F_c$ map calculated from 50-3.8 Å, contoured at 2.5σ, wire mesh) of $Sr^{2+}$ (spheres) in the cavity of Kir2.2. The channel is shown as a ribbon with the subunit closest to the viewer removed. Only the side chains facing the cavity are shown (sticks). (FIG. 4E) Stereoview of the ion binding site near the upper ring of charges in the cytoplasmic domain of Kir2.2, viewed from the extracellular side. Residues E225, H227, E300, and Q311 are shown as sticks, and hydrogen bonds between them are indicated as dashed black lines. Electron density (200 mM $Sr^{2+}$, $F_o$-$F_c$ map calculated from 50-3.8 Å, contoured at 4.5σ) of $Sr^{2+}$ (spheres) is shown as wire mesh. (FIG. 4F) Stereoview of the ion binding site at the lower ring of charges in the cytoplasmic domain of Kir2.2, viewed from the intracellular side. Residues F255, D256, and K257 are shown as sticks, and hydrogen bonds between D256 from different subunits are indicated as dashed black lines. Electron density (200 mM $Sr^{2+}$, $F_o$-$F_c$ map calculated from 50-3.8 Å, contoured at 4.5σ) of $Sr^+$ (spheres) is shown as wire mesh.

(FIG. 5A) (FIG. 5B) Surface representation of chicken Kir2.2 (FIG. 5A) and Kv1.2-Kv2.1 paddle chimera (FIG. 5B, PDB ID 2R9R) in stereo, viewed from the extracellular side. The four protrusions formed by the top of the turrets are highlighted with a black perimeter and F148 in Kir2.2 is labeled. (FIG. 5C) Stereo representation of electron density (wire mesh) for the turret region ($2F_o$-$F_c$, calculated from 50-3.1 Å using phases from the final model and contoured at 1.0σ). The turret is shown as sticks (colored according to atom types), and residues corresponding to the highlighted protrusions in panel A are labeled. (FIG. 5D) A close-up view of the turret region in a single subunit in stereo. Side chains of those conserved residues among the turrets of eukaryotic Kir channels, as well as C155 are shown as sticks. Hydrogen bonds between H108, D110 and C123 are indicated as dashed black lines.

(FIG. 6A) (FIG. 6B) Macroscopic currents are shown from an uninjected oocyte (FIG. 6A) and a chicken Kir2.2 channel injected oocyte (FIG. 6B) without subtracting leak and capacitive currents. The currents were recorded from oocytes using two-electrode voltage-clamp. Voltage pulses: holding potential (h.p.) 0 mV, depolarizing steps: −80 mV to +80 mV, ΔV=10 mV, stepping back to 0 mV. (FIG. 6C) Macroscopic currents recorded from oocytes using patch-clamp. The three current traces show a current trace recorded on-cell (labeled B), a trace recorded immediately after excision of the inside-out patch (labeled C), and a trace recorded approximately 10 minutes after the excision (labeled A) Voltage pulses: ramp from −80 mV to =80 mV over 10 seconds duration, (FIG. 6D) I-V curve from a patch containing only a few channels. The single channel current is graphed as a function of voltage (inset).

FIG. 10 depicts FLOWCHART 2, which illustrates an assay that may be used to identify compounds which specifically bind the Kir channel turret region is an assay utilizing a fluorescent dye.

DETAILED DESCRIPTION OF THE INVENTION

The present invention is based in part on the discovery of an important structural feature present in Kir channel proteins. In particular, the present invention relates to the discovery of a "turret region" which is highly ordered in structure and which differs in sequence among different Kir channel proteins. In addition, this turret region faces the outside of the cell making the protein accessible to compounds that bind or otherwise interact with this turret region thereby affecting the ability of the Kir channel to function. The discovery of the fact that this turret region, which differs in sequence among members of the Kir channel family, is structured provides a basis to identify compounds which can treat disease states related to Kir channel functions.

Example 1 provided below presents a determination of the crystal structure of a eukaryotic Kir channel protein. In particular, the crystal structure of the chicken Kir channel protein, Kir2.2 is presented. Excluding unstructured amino and carboxy termini, the chicken Kir2.2 protein is 90% identical to human Kir2.2. More importantly, for the purposes of the present invention, these structural studies demonstrate that Kir channels have a large structured turret region which provide the basis for the development of compounds that may be used to bind and interact with these turrets and treat disease states related to the functioning of Kir channels. In particular, these turret regions suggest approaches to the development of inhibitory compounds which will bind to a specific member of the Kir channel family of proteins and inhibit Kir channel function.

Figure 1B:
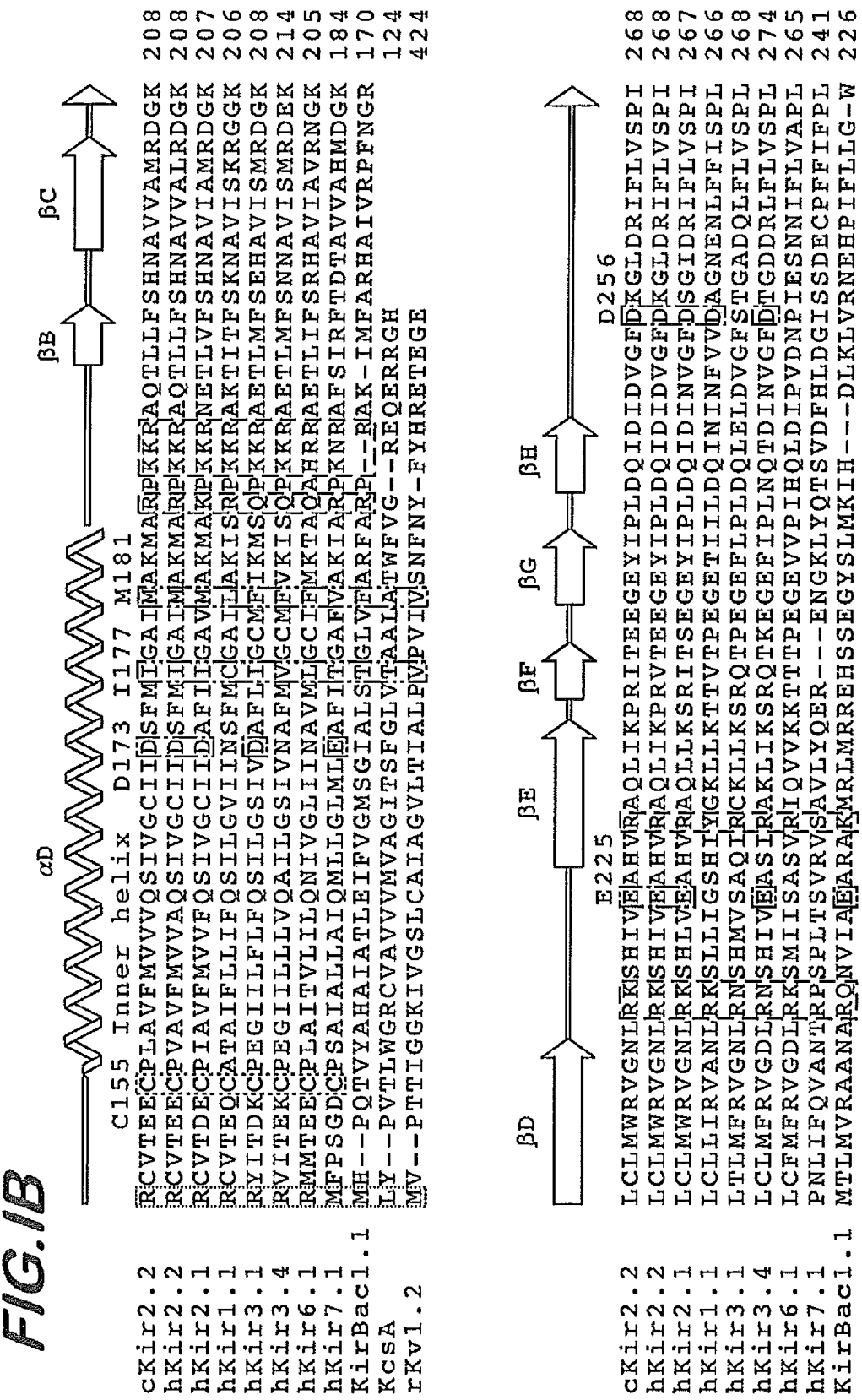
Figure 1C:
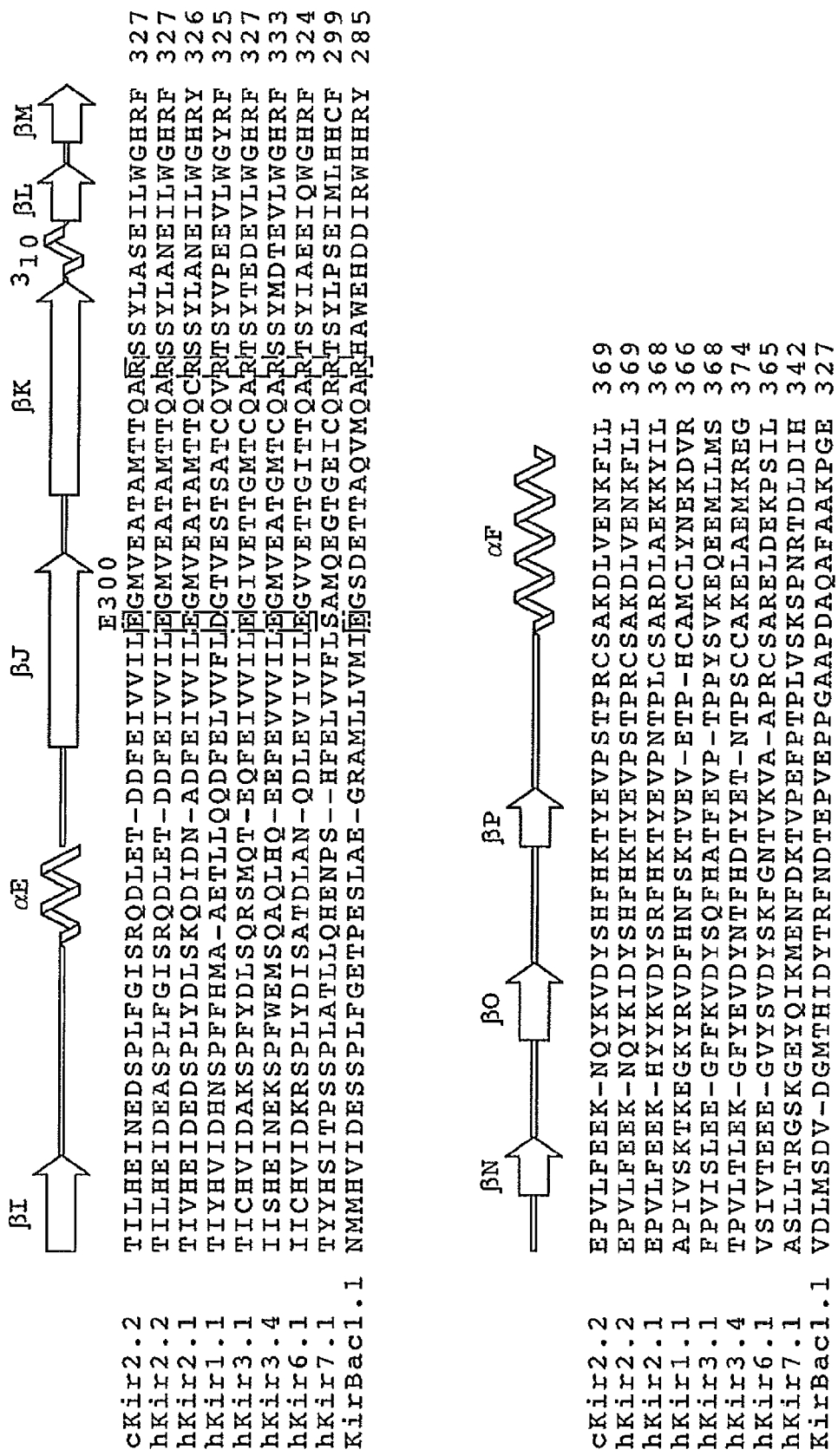

The turret region of a variety of Kir channel proteins are identified in FIGS. 1A-1C and in the sequence listings of the present application. In particular, FIGS. 1A-1C illustrates that a sequence alignment of various human Kir channels indicates that the turret region begins with a consensus sequence HGDL (or minor sequence variations thereof) and extends six amino acid residues after a highly conserved cysteine residue labeled as C123 in FIGS. 1A-1C. This turret region is highly conserved and most of the variation that occurs in the sequence is located in a variable portion located after the sequence HGDL up to the cysteine labeled as C123. This variable portion within the turret region constitutes a basis for differentiating Kir channels from one another and provides a target for mutagenesis assays to identify compounds capable of turret specific binding.

Given the identification of the structured turret region in the crystal structure, the turret region of other Kir channels may be identified using sequence alignment programs and the teachings of the present invention relating to the consensus sequence and structural features of the Kir channels.

Based on this structural information, methods are presented below in which the identification of the turret region and knowledge of the amino acid sequence of the turret may be used to develop assays to identify therapeutic compounds which include, but are not limited to, antibodies, nucleic acids, peptides and small molecules that are capable of selective binding to Kir channel proteins.

In general the methods of the present invention for identifying a compound that modulates ion channel activity of a Kir channel comprises a two step process: a first step of identifying a compound which binds the turret region of a Kir channel; and a second step of determining if the compound modulates the ion channel activity of the Kir channel.

Production of Antibodies

In a first method for identifying compounds that modulate the ion channel activity of a Kir Channel, antibodies are prepared against a Kir channel. A variety of Kir channels are known and the methods described below may be used to prepare antibodies against any Kir channel. Given the present discovery of the importance of the turret region in distinguishing one Kir channel from another, it is particularly useful to obtain antibodies which bind the turret region, The Antigens and Assay Reagents Two types of Kir channel proteins may be of particular utility in preparing antibodies. The first type are human Kir channel proteins. The second type are chimeric constructs which utilize a non-human sequence, preferably a eukaryotic sequence, such as a chicken sequence, in particular a chicken Kir 2.2 sequence into which a human Kir channel turret region has been inserted, thereby replacing the native turret region. As an example, chimeric proteins which utilize a chicken Kir2.2 "scaffold" into which the turret region from a given human Kir channel is inserted may be used to prepare antibodies which are specific for different human Kir channel proteins. Both human and chimeric Kir channels may be full length proteins or may contain deletions at the amino and/or carboxy termini of the protein if desired.

Conventional molecular biology, microbiology, and recombinant DNA techniques within the skill of the art may be used in order to prepare human and chimeric Kir channel proteins. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)1; B. Perbal, A Practical Guide To Molecular Cloning (1984); F. M. Ausubel et al. (eds.), Current Protocols in Molecular Biology, John Wiley & Sons, Inc. (1994); Molecular Cloning: A Laboratory Manual Third Edition (Joseph Sambrook and David W, Russell Cold Spring Harbor Laboratory Press (2001)]; The Condensed Protocols from Molecular Cloning: A Laboratory Manual [Joseph Sambrook and David W. Russell, Cold Spring Harbor Laboratory Press (2006)]; Gene Cloning and Manipulation Second Edition [Christopher Howe, Cambridge University Press (2007)].

The cDNA sequences for exemplary human Kir channels are presented in SEQ ID NOS 30-43. The cDNA sequence of the chicken Kir2.2 channel is presented in SEQ ID NO: 45. DNA and cDNA sequences for other types of Kir channels are available in public databases. The turret regions of exemplary human Kir proteins are identified in SEQ ID NOs: 46-56.

Expression of Chicken Kir 2.2

As an example of expression and purification of a eukaryotic Kir channel a protocol for preparing a chicken Kir 2.2 channel protein is provided below. Using standard techniques this procedure may be modified to prepare any of the human Kir channel proteins or a desired chimeric Kir channel protein.

To prepare the chicken Kir 2.2 channel, a synthetic gene fragment (Bio Basic, Inc.) encoding residues 38 to 369 of chicken Kir2.2 channel (GI:118097849) was ligated into the XhoI/EcoRI cloning sites of a modified pPICZ-B vector (Invitrogen). The resulting protein has green fluorescent protein (GFP) and a 1D4 antibody recognition sequence (TETSQVAPA) on the C terminus (I), separated by a PreScission protease cleavage site (SNSLEVLFQ/GP).

The construct was linearized using PmeI and transformed into a HIS+ strain of SMD1163 of *Pichia pastoris* (Invitrogen) by electroporation (BioRad Micropulser). Transformants were selected on YPDS plates containing 400-1200μ/ml Zeocin (Invitrogen). Resistant colonies were tested for expression by anti-1D4 tag Western Blot. For large-scale expression, small cultures grown from the best expressing colony were diluted into BMGY media (Invitrogen) and inoculated at 29° C. overnight, until OD600 reached between 20-30. Cells were then pelleted, resuspended in BMM media (Invitrogen) and expressed overnight at 24° C. Cells were harvested, flash-frozen in liquid N2, and stored at −80° C. until needed.

Cells were lysed in a Retsch, Inc. Model MM301 mixer mill (5×3.0 minutes at 25 cps). The lysis buffer contained 150 mM KCl, 50 mM TRIS-HCl pH 8.0, 0.1 mg/ml deoxyribonuclease I, 0.1 μg/ml pepstatin, 1 μg/ml leupeptin, 1 μg/ml aprotinin, 0.1 mg/ml soy trypsin inhibitor, 1 mM benzamidine, 0.1 mg/nil AEBSF, with 1 mM phenylmethysulfonyl fluoride added just before lysis (3.0 ml lysis buffer/g cells). pH of the lysate was adjusted to 8.0 with KOH. The lysate was extracted with 100 mM DM (n2 decyl-β-D-maltopyranoside, Anatrace, solgrade) at room temperature for 1 hour with stirring, and then centrifuged for 40 minutes at 30,000 g, 10° C. Supernatant was added to 1D4-affinity resin pre-equilibrated with 150 mM KCl, 50 mM TRIS-HCl pH 8.0, and 4 mM DM. Suspension was layered with Argon and mixed by inversion for 2 hours at room temperature. Beads were collected on a column by gravity, washed with 2 column volumes of buffer (150 mM KCl, 50 mM TRIS-HCl pH 8.0, 1 mM EDTA pH 8.0, and 4 mM DM), and eluted with buffer plus 1 mg/ml 1D4 peptide (AnaSpec, Inc.) over 1 hour at room temperature. 20 mM DTT (Dithiothreitol) and 3 mM TECP were added to eluted protein. The protein was then digested with PreScission protease (20:1 w/w ratio) overnight at 4° C. Concentrated protein was further purified on a Superdex-200 gel filtration column in 150 mM KCl, 20 mM TRIS-HCl pH 8.0, 4 mM DM (anagrade), 3 mM TCEP, 20 mM DTT and 1 mM EDTA at 4° C. In a preferred embodiment, the protein extract is maintained in a mild detergent, such as DM, which will maintain the three-dimensional structure of the Kir channel.

Preparation of Human/Chicken Hybrid Kir Channels

Using standard techniques in molecular biology, chimeric Kir channel protein may be prepared by inserting the turret region of a human Kir channel protein into the Kir2.2 chicken sequence described above. The location of the turret regions are identified in FIGS. 1A-1C.

By way of example, site-directed mutagenesis procedures may be used to insert the coding sequence for a human turret region into a eukaryotic "scaffold" Kir channel coding region. In a preferred embodiment, Strategene's QuickChange® is used. QuickChange® utilizes a supercoiled double-stranded DNA (dsDNA) vector with an insert of interest and two synthetic oligonucleotide primers containing the desired mutation. The oligonucleotide primers, each complementary to opposite strands of the vector, are extended during temperature cycling by PfuTurbo DNA polymerase. The desired mutation (in this case—the insertion of the human turret region) should be in the middle of the primer with about 10-15 bases of correct sequence on both sides. Incorporation of the oligonucleotide primers generates a mutated plasmid containing staggered nicks. Following temperature cycling, the product is treated with Dpn I. The Dpn I endonuclease (target sequence: 5'-Gm$^6$ATC-3') is specific for methylated and hemimethylated DNA and is used to digest the parental DNA template and to select for mutation-containing synthesized DNA. DNA isolated from almost all *E. coli* strains is Dam methylated and therefore susceptible to Dpn I digestion. The nicked vector DNA containing the desired mutations is then transformed into XL1-Blue supercompetent cells. See, e.g. U.S. Pat. Nos. 5,789,166, 5,932,419, and 6,391,548.

As an example, the chicken Kir2.2 protein may be used as a scaffold and the human Kir2.2 channel turret region synthesized for insertion. This methodology can be repeated with any combination of scaffold protein and human turret region.

Preparation of Mutated Turret Regions

Given the identification of the turret regions in the human Kir channels site directed mutagenesis or other techniques known in the art may be used to prepare proteins having mutations in the DNA sequence of the turret. In a preferred embodiment, Strategene's QuickChange® is used. Such mutations should be non-silent mutations—that is the mutations should result in amino acid changes at positions within the turret region.

Generation of Antibodies

A human Kir protein or a chimeric Kir channel protein is prepared using standard techniques such as those outlined herein, and used in standard techniques to obtain antibodies.

A variety of antibodies may be used in the present invention and such antibodies include but are not limited to polyclonal, monoclonal, human, humanized chimeric, an intact immunoglobulin molecule, an antibody fragment, single chain, ScFv, Fab fragments, F(ab)$_2$ Fab, Fv and a disulfide linked Fv.

Various procedures known in the art may be used for the production of antibodies. Host animals can be immunized by injection with a human Kir channel protein, or chimeric Kir protein or fragments of these proteins. Animals which may be used to generate antibodies include, but are not limited to, rabbits, mice, rats, sheep, goats, and others known in the art. The human and chimeric proteins of the present invention may also be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies directed toward a Kir channel protein of the present invention, any technique that provides for the production of antibody molecules by continuous cell lines in culture may be used. These include but are not limited to the hybridoma technique originally developed by Kohler and Milstein [Nature 256:495-497 (1975)], as well as the trioma technique, the human B-cell hybridoma technique [Kozbor et al., Immunology Today 4:72 1983); Cote et al., Proc. Natl. Acad. Sci. U.S.A. 80:2026-2030 (1983)], and the EBV-hybridoma technique to produce human monoclonal antibodies [Cole et al., in Monoclonal Antibodies and Cancer Therapy, Alan R. Liss, Inc., pp. 77-96 (1985)]. In addition, techniques developed for the production of "chimeric antibodies" [Morrison et al., J. Bacterial. 159: 870 (1984); Neuberger et al., Nature 312:604-608 (1984); Takeda et al., Nature 314:452-454 (1985)] by splicing the genes from a mouse antibody molecule specific for an isolated Kir channel protein of the present invention, or conserved variants thereof, together with a fragment of a human antibody molecule of appropriate biological activity can be used.

Human antibodies can be prepared using any technique. Examples of techniques for human monoclonal antibody production include those described by Cole et al. (Monoclonal Antibodies and Cancer Therapy, Alan R. Liss, p. 77, 1985) and by Boemer et al. (J. Immunol., 147(1):86-95, 1991). Human antibodies (and fragments thereof) can also be produced using phage display libraries (Hoogenboom et al., J. Mol. Biol., 227:331, 1991; Marks et al., J. Mol. Biol., 222: 581, 1991), Information on monoclonal and other types of therapeutic antibodies can also be found in Cellular and Molecular Immunology, 6th Edition, [A. K. Abbas, A. H. Lichtman, S. Pillai (Saunders Elsevier Press, 2007)], and U.S. Pat. Nos. 7,390,887 and 7,629,171. For a discussion of various types of therapeutic antibodies, see Strategies and Challenges for the Next Generation of Therapeutic Antibodies, A. Beck, T. Wurch, C, Bailly and N. Corvaia, Nature Rev. Immuno. 10, 345-352 (2010).

Human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA, 90:2551-255 (1993); Jakobovits et al., Nature, 362:255-258 (1993); Bruggermann et al., Year in Immunol., 7:33 (1993)).

Humanized antibodies may also be used in the present invention. Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody. Methods for humanizing non-human antibodies are well known in the art. For example, humanized antibodies can be generated according to the methods of Winter and co-workers (Jones et al., Nature, 321:522-525 (1986), Riechmann et al., Nature, 332:

323-327 (1988), Verhoeyen et al., Science, 239:1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

Techniques described for the production of single chain antibodies [U.S. Pat. Nos. 5,476,786 and 5,132,405 to Huston; U.S. Pat. No. 4,946,778] can be adapted to produce single chain antibodies specific for a Kir channel protein. An additional embodiment of the invention utilizes the techniques described for the construction of Fab expression libraries [Huse et al., Science 246:1275-1281 (1989)] to allow rapid and easy identification of monoclonal Fab fragments with the desired specificity for the Kir channel proteins.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

Antibodies or fragments thereof, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. Such methods are readily apparent to a skilled practitioner in the art and can include site-specific mutagenesis of the nucleic acid encoding the antibody or antibody fragment.

Nucleic Acids

The compounds of the present invention include nucleic acids. In particular, nucleic acid sequences capable of binding to a Kir channel may be used in the practice of the present invention. These nucleic acids may be identified using in vitro selection of sequences which bind Kir channel proteins, in particular the turret region of the Kir channel proteins. One type of nucleic acid that is of particular interest is an aptamer. Typically aptamers are small nucleic acid sequences ranging from 15-50 bases in length that fold into defined secondary and tertiary structures that bind to another molecule. This binding is not the typical nucleic acid to nucleic acid hydrogen bond formation but the binding of aptamers can include all other types of covalent and noncovalent binding. In a preferred embodiment, the nucleic acid is DNA, however, other nucleic acids such as RNA may be used. The nucleic acids may be modified or prepared using techniques known in the art to increase the stability of nucleic acids. Representative examples of how to make and use aptamers to bind a variety of different target molecules can be found in the following U.S. Pat. Nos. 5,582,981; 5,595,877; 5,637,459; 6,020,130; 6,028,186; 6,030,776; and 6,051,698. See also Published U.S. patent application Ser. No. 11/917,884 (publication No. US2009/0155779A1); Bock L C, Griffin L C, Latham J A, Vermaas E H, Took J J (February 1992). "Selection of single-stranded DNA molecules that bind and inhibit human thrombin" *Nature* 355(6360): 564-6; Bunka D H, Stockley P G (August 2006) "Aptamers come of age—at last" *Nat Rev Microbio.* 4(8): 588-96.

Small Protein/Peptide Compounds

Small Protein/Peptide Compounds may also be used in the practice of the present invention. In particular, small proteins may be prepared and screened for the ability to bind to a Kir channel protein based on binding assays disclosed herein and known in the art. Small molecules such as toxins may also be used in the practice of the invention. In particular, small proteins/peptides modeled on toxins which bind to Kir channel proteins may be prepared and tested for the ability to bind and modulate the activity of Kir channel proteins. (Ramu, et al. (2008) Engineered specific and high affinity inhibition for a subtype of inward rectifier Kir channels Proc. Nat'l Acid Sci USA 105:10774-10778)

A variety of toxins may provide information useful in designing a compound useful in the practice of the present invention. In particular, scorpion toxins (Lu and Mackinnon, 1997 Biochemistry, vol. 36, no, 23, pp 6936 to 6940) snake toxins (for example, the 57 amino acid δ-dendrotoxin from the green mamba snake which inhibits Kir 1.1 channels, (J. P. Imredy, C. Chen, R. Mackinnon, BioChemistry 37, 14867 (Oct. 20, 1998)) and bee venom toxins (Ramu, et al. (2008) Engineered specific and high affinity inhibition for a subtype of inward rectifier Kir channels Proc. Nat'l Acid Sci USA 105:10774-10778) may be helpful in synthesizing libraries of protein/peptide compounds that can bind and effect a Kir channel. Known toxins are often small proteins typically between 20 and 50 amino acids in size containing disulfide bridges. For some of these toxins, the surface important for binding to a Kir channel protein is known and stretches of amino acids of less than 10 amino acids are believed to be important for binding specificity.

A library of these toxin-based compounds may be prepared while maintaining the key amino acids such as cysteine residues that are important for the folding and structure of the proteins. The amino acid residues important for binding to a Kir channel may be randomized to generate proteins/peptides with enhanced binding strength and turret based specificity for the different members of the Kir channel family of proteins.

Phage Display

One method known in the art to rapidly screen a large variety of potential binding proteins/peptides is a phage display assay.

Phage display libraries may be prepared using known protocols. "Filamentous fusion phage: novel expression vectors that display cloned antigens on the virion surface". *Science* 288 (4705): 1315-1317. Smith G P, Petrenko V A (1997). "Phage display". *Chem. Rev.* 97 (2): 391-410. Kehoe J W, Kay B K (2005), "Filamentous phage display in the new millennium". *Chem. Rev.* 105 (11): 4056-4072. Hufton S E, Moerkerk P T, Meulemans E V, de Bruine A, Arends J W, Hoogenboom H R (1999). "Phage display of cDNA repertoires: the pVI display system and its applications for the selection of immunogenic ligands." *J. Immunol. Methods* 231 (1-2): 39-51. Lunder M, Bratkovie T, Doljak B, Kreft S, Urleb U, Strukelj B, Plazar N. (2005). "Comparison of bacterial and phage display peptide libraries in search of target-binding motif". *Appl. Biochem. Biotechnol.* 127 (2): 125-31. Lunder M, Bratkovic T, Kreft S, Strukelj B (2005). "Peptide inhibitor of pancreatic lipase selected by phage display using different elution strategies". *J. Lipid Res.* 2005 46 (7): 1512-6.)

Using phage display the protein/peptide constructs may be expressed on the outer coat of the phage. To identify useful sequences a Kir channel protein may be immobilized on the surface of a well of a standard assay plate, and a phage that displays a protein that binds to Kir channels will bind the target Kir channel protein and remain bound while non-binding phage are removed by washing the plates. The bound phage can be eluted and used to produce more phage for further binding assays. These binding assays may be performed with Kir channels having mutated turrets and wild type turrets to select for proteins/peptides that bind in the turret region. Repeated cycles of these binding assays ('panning') results in the identification of phage containing potentially strong binding sequences.

Phage that contain these strong binding sequences can be used to infect a suitable bacterial host, and phagemids are collected and the DNA sequence of interest encoding the binding region excised and sequenced to identify the protein/peptide compound which be further tested using the assays described below.

Small Molecules

Small molecules may also be used in the practice of the present invention. In particular, small molecules may be prepared and screened for the ability to bind to a Kir channel protein based on binding assays disclosed herein and known in the art. See for example U.S. Pat. No. 6,641,997. Additionally, small molecule libraries may also be screened.

Immunoassays

Once an antibody has been generated by the methods described above, a variety of different immunoassays may be performed to identify antibodies that bind property folded Kir channels, are specific for the turret region of the Kir channel and can differentiate between different members of the Kir family based on the turret region.

It is believed that ELISA and Western blot assays are straightforward and efficient assays to identify such antibodies before performing functional assays such as electrophysiological assays.

In general, immunoassays involve contacting a Kir channel protein with an anti-Kir channel antibody under conditions effective, and for a period of time sufficient, to allow the formation of immune complexes (primary immune complexes). Forming such complexes is generally a matter of simply bringing into contact the antibody and the Kir channel protein sample and incubating the mixture for a period of time long enough for the antibodies to form immune complexes with, i.e., to bind to, any molecule (e.g., antigens) present to which the antibodies can bind.

In many forms of immunoassay, the sample-antibody composition, such as an ELISA plate or Western blot, can then be washed to remove any non-specifically bound antibody species, allowing only those antibodies specifically bound within the primary immune complexes to be detected. Immunoassays can include methods for detecting or quantifying the amount of a molecule of interest (such as the disclosed biomarkers or their antibodies) in a sample. In general, the detection of an immunocomplex formation is well known in the art and can be achieved by numerous approaches. These methods are generally based upon the detection of a label or marker, such as any radioactive, fluorescent, biological or enzymatic tags or any other known label. Such assays include but are not limited to ELISA, western blots, radioimmunoassay, (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), precipitation reactions, agglutination assays (e.g., gel agglutination assays, hemagglutination assays), complement fixation assays, immunofluorescence assays, protein A assays, and immunoelectrophoresis assays, and other assays known in the art.

Antibody binding can be detected by detecting a label on the primary antibody or the primary antibody is detected by detecting binding of a secondary antibody or reagent to the primary antibody. For some assays, the secondary antibody is labeled. Many means are known in the art for detecting binding in an immunoassay and are within the scope of the present invention.

The use of immunoassays to detect a specific protein can involve the separation of the proteins by electrophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique. Electrophoresis is used in the Western blots described below.

ELISA

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase. For descriptions of ELISA procedures, see Voller, A. et al., J. Clin. Pathol. 31:507-520 (1978); Butler, J. E., Meth. Enzymol. 73:482-523 (1981); Maggio, E. (ed.), Enzyme Immunoassay, CRC Press, Boca Raton, 1980; Butler, J. E., In: Structure of Antigens, Vol. 1 (Van Regenmortel, M., CRC Press, Boca Raton, 1992, pp. 209-259; Butler, J. E., In: van Oss, C. J. et al., (eds), Immunochemistry, Marcel Dekker, Inc., New York, 1994, pp. 759-803; Butler, J. E. (ed.), Immunochemistry of Solid-Phase Immunoassay, CRC Press, Boca Raton, 1991); Crowther, "ELISA: Theory and Practice," In: Methods in Molecule Biology, Vol. 42, Humana Press; New Jersey, 1995;U.S. Pat. No. 4,376,110, each of which is incorporated herein by reference in its entirety and specifically for teachings regarding ELISA methods.

In preferred embodiments of the present invention, ELISA assays are used to identify antibodies that bind to the Kir channel proteins and are specific to the turret region.

As illustrated in FLOWCHART 1, a first ELISA assay is performed to identify antibodies that bind to the Kir channel protein. As an example, if a human Kir 2.2 channel protein is used as an antigen, an ELISA Assay is performed to identify antibodies that bind to human Kir 2.2 channel protein.

By way of an example ELISA assay, solutions are prepared as follows:

Buffer A: Protein buffer containing detergent slightly above CMC
Coating Solution—Buffer A+20 ug/ml Protein (50 ul/well, 5.0 ml./plate)
Wash Solution—Buffer A (200 ul/well×14 washes; 2.8 ml/well, 280 ml total/plate)
Blocking Solution—Buffer A+5% BSA (0.45 u filtered) (400 ul/well, 40 ml./plate)

Primary Ab solution—Cell culture supernatant (diluted 1:1 with 2× Buffer A/2% BSA) or control sera (1:100 in Buffer A+2% BSA)

Secondary Ab Solution—1:10,000 goat a mouse-Horseradish peroxidase conjugate in Buffer A+2% BSA (100 ul/well, 10 ml/plate)

Substrate Solution—1:1 TMB:$H_2O_2$ (100 ul/well, 10 ml/plate)

Stop Solution—2M H2SO4 (100 ul/well, 10 ml./plate)

The following steps are then performed:
a) Add 50 ul of coating solution to each well. Prepare coated plates the day before the assay and store at 4° C. overnight, or prepare on day of assay and allow to shake for 1 hour at room temperature. Add solution directly to the bottom of the well, avoiding the sides as much as possible. Coat at least 2 more wells than you have samples for (+) and (−) controls, Leave at least 2 wells uncoated (just wash solution) as negative controls.
b) Remove coating solution by pouring out and smacking plate face down on a paper towel. Wash wells 3× by adding 200 ul of wash solution to each well, shaking for 1 minute, pouring out wash solution and smacking plates face down on paper towels.
c) Add 300 ul of blocking solution to each well and let plates sit at room temperature for 2 hour.
d) Remove blocking solution and wash wells 3× with 200 ul of washing solution.
e) Add 50 ul 2× Buffer to each well (except controls)
f) Add 50 ul primary antibody solution to the 50 ul 2× buffer in each well and mix. Add diluted (+) control serum to a coated and uncoated well and diluted (−) control serum to coated and uncoated well. Let plates sit at room temperature for 1 hour on orbital shaker.
g) Remove Primary Ab solution and wash wells 3× with 200 ul washing solution.
h) Add 100 ul secondary Ab solution to each well and let plates sit at room temperature for 1 hour.

The plates are then examined to determine if antibodies for a Kir channel protein are present using standard techniques as described above.

Western Blot

Western blotting or immunoblotting allows the determination of the molecular mass of a protein and the measurement of relative amounts of the protein present in different samples. Detection methods include chemiluminescence and chromagenic detection. Standard methods for Western blot analysis can be found in, for example, D. M. Bollag et al., Protein Methods (2d edition 1996) and E. Harlow & D. Lane, Antibodies, a Laboratory Manual (1988), U.S. Pat. No. 4,452,901, each of which is herein incorporated by reference in their entirety for teachings regarding Western blot methods. Generally, proteins are separated by gel electrophoresis, usually SDS-PAGE. For the assays used in the present invention for initial antibody screening, it is preferred to use an SDS-PAGE so as to denature the Kir channel proteins used in the blot. The proteins are transferred to a sheet of special blotting paper, e.g., nitrocellulose, though other types of paper, or membranes, can be used. The proteins retain the same pattern of separation they had on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, $^{125}$I). Probes for the detection of antibody binding can be conjugated anti-immunoglobulins, conjugated staphylococcal Protein A (binds IgG), or probes to biotinylated primary antibodies (e.g., conjugated avidin/streptavidin).

As illustrated in FLOWCHART 1, a western blot is performed to determine if an antibody binds to the denatured form of a Kir channel protein. The combination of the ELISA and the Western blot Kir channel assays as illustrated in FLOWCHART 1 facilitates the identification of antibodies that recognize the properly folded native Kir channel (ELISA Positive) but not the denatured (Western Negative) form of the protein.

In particular, if a given antibody binds to a Kir channel protein in an ELISA assay ("ELISA Positive"), but fails to bind to the same Kir channel protein in a Western blot (Western Negative), then the antibody is binding to the native conformation of the protein but not the denatured form.

Identification of Antibodies with Turret Specificity

Given the discovery in the present invention of the importance of the turret regions and the identification of the region of the Kir proteins which constitute the turret region it is possible to prepare Kir channel proteins which contain mutations located in the turret region. This in turn provides the basis for identification of antibodies that are specific for the turret region of the Kir channel proteins. In particular, the determination of the atomic structure of what constitutes the turret region of the Kir channels identifies where to introduce such mutations so as to selectively identify anti-Kir Channel antibodies that are directed against the turret. Such mutations may be made in a variety of places, such as following the L residue in the sequence HGDL (or slight variations of that sequence) and up to but not including the conserved cysteine labeled C123 in the structure of the proteins (see FIGS. 1A-1C). Examples of these variable portions of certain turret regions is provided in SEQ ID NOs 1-13. Kir channel proteins which contain mutations in the turret region, or preferably in the variable portion, may be used in assays described below.

To identify antibodies that are specific for the turret region of the Kir channel further ELISA assays may be performed as illustrated in FLOWCHART 1. These ELISA assays utilize Kir channels with mutated turret regions. Antibodies that bind a normal Kir channel in an ELISA assay but do not bind a channel with a mutated turret will be isolated since these antibodies may be considered turret specific—that is the epitope for the antibody is located in the turret region of the protein. The source of these antibodies will be used to prepare monoclonal antibodies using standard techniques as described above. An additional assay described below and presented in FLOWCHART 2 identifies antibodies or other compounds with the ability to bind the turret region using a fluorescent assay.

Assays for Kir Channel Activity

Even if an antibody or other type of compound binds the turret region its utility as a therapeutic compound is based on its functional effect on a Kir channel. Accordingly, the next step is to determine if an antibody which binds the turret region of a Kir channel is capable of modulating electrolyte processing. Monoclonal antibodies prepared from turret specific antibodies identified above can be used in electrophysiological assays as can other compounds found to have binding specificity for the turret region of Kir channels.

There are a variety of electrophysiological assays known to those with skill in the art which may be used to determine whether the compounds of the present invention have an effect on the electrophysiological state of a Kir Channel.

Useful electrophysiological assays include a variety of in vitro and in vivo assays, e.g., measuring voltage, current, measuring membrane potential, measuring ion flux, e.g., potassium or rubidium, measuring potassium concentration, measuring second messengers and transcription levels, and using e.g., voltage-sensitive dyes, radioactive tracers, electrode voltage clamps and patch-clamp electrophysiology. Such assays can be used to test for both inhibitors and activators of Kir channels.

Modulators of the Kir channels may be tested using biologically active, functional Kir channels, either recombinant or naturally occurring. In recombinantly based assays, the subunits are typically expressed and modulation is tested using one of the in vitro or in vivo assays described herein.

In brief, samples or assays that are treated with a potential Kir channel turret binding compounds inhibitors or activators are compared to control samples without the test compound, to examine the extent of modulation. Control samples e.g. those untreated with the compounds are assigned a relative Kir channel activity value of 100. Inhibition is present when Kir channel activity value relative to the control is about 90%, preferably 50%, more preferably 25%.

It should be noted that the compounds may also result in activation of Kir channels. Activation of channels is achieved when the select Kir channel activity value relative to the control is 110%, more preferably 150%, more preferable 200% higher. It is possible that for treating some diseases states such activating compounds may be useful alone or in combination with inhibitors.

Changes in ion flux may be assessed by determining changes in polarization (i.e., electrical potential) of the cell or membrane expressing the Kir channels of this invention. A preferred means to determine changes in cellular polarization is by measuring changes in current (thereby measuring changes in polarization) with voltage-clamp and patch-clamp techniques, e.g., the "outside-out" mode, and the "whole cell" mode (see, e.g., Ackerman et al., New Engl. J. Med. 336: 1575-1595 (1997) and *Single Channel Recording*, Plenum Press, B. Sakmann and E. Neher eds). Whole cell currents are conveniently determined using the standard methodology (see, e.g., Hamil et al., P Flugers. Archly. 391:85 (1981). Other known assays include: radiolabeled rubidium flux assays and fluorescence assays using voltage-sensitive dyes (see, e.g., Vestergarrd-Bogind et al., J. Membrane Biol. 88:67-75 (1988); Daniel et al., J. Pharmacol. Meth. 25:185-193 (1991); Holevinsky et al., J. Membrane Biology 137:59-70 (1994)). Assays for compounds capable of inhibiting or increasing potassium flux through the channel proteins can be performed by application of the compounds to a bath solution in contact with and comprising cells having an channel of the present invention (see e.g., Blatz et al., Nature 323:718-720 (1986); Park, J. Physiol. 481:555-570 (1994)). Generally, the compounds to be tested are present in the range from 1 pM to 100 μM.

The effects of the test compounds upon the function of the Kir channels can be measured by changes in the electrical currents or ionic flux or by the consequences of changes in currents and flux. Changes in electrical current or ionic flux are measured by either increases or decreases in flux of cations such as potassium or rubidium ions. The cations can be measured in a variety of standard ways. They can be measured directly by concentration changes of the ions or indirectly by membrane potential or by radiolabeling of the ions. Consequences of the test compound on ion flux can be quite varied. Accordingly, any suitable physiological change can be used to assess the influence of a test compound on the Kir channels of this invention. The effects of a test compound can be measured by a toxin binding assay. When the functional consequences are determined using intact cells or animals, one can also measure a variety of effects such as transmitter release (e.g., dopamine), hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as $[Ca^{2+}]$.

Two Electrode Voltage Clamp Assay

One assay that may be of particular use in the present invention is a two electrode voltage clamp assay. This assay may be performed using any of these Kir channel proteins and compounds of the present invention using modifications readily known to those in the art. In the example below, this assay was conducted using the chicken Kir 2.2 channel. To perform this assay, *Xenopus* oocytes will be harvested from mature female *Xenopus laevis* and defolliculated by collagenase treatment for 1-2 hours. Oocytes will then rinsed thoroughly and stored in ND96 solution (96 mM NaCl, 2 mM KCl, 1.8 mM $CaCl_2$, 1.0 mM $MgCl_2$, 5 mM HEPES, 50 μg/ml gentamycin, pH 7.6 with NaOH). Defolliculated oocytes will be selected 2-4 hours after collagenase treatment and injected with cRNA the next day. The injected oocytes will be incubated in ND96 solution for 1-5 days before recording. All oocytes will be stored in an incubator at 18° C.

The desired human or chimeric Kir channel protein DNA will be sub-cloned into the pGEM vector (Promega). cRNA will be prepared using T7 RNA polymerase (Promega) from NdeI-linearized plasmid DNA.

All recordings will be performed at room temperature. For two-electrode voltage-clamp experiments, oocytes will be held at 0 mV and pulsed from −80 mV to +80 mV with 10 mV increment steps. Recording solution will contain 98 mM KCl, 0.3 mM $CaCl_2$, 1 mM $MgCl_2$, and 5 mM HEPES pH 7.6. The ionic currents will be recorded with an oocyte clamp amplifier (OC-725C, Warner Instrument Corp.). The recorded signal will be filtered at 1 kHz and sampled at 10 kHz using an analogue-to-digital converter (Digidata 1440A, Axon Instruments, Inc) interfaced with a computer. pClamp10.1 software (Axon Instruments, Inc) will be used for controlling the amplifier and data acquisition.

Patch Clamp Assays

Patch clamp assays use a micropipette attached to a cell membrane to allow recording from a single ion channel in the cell membrane.

To perform this type of assay a micropipette which serves as a microelectrode is positioned next to a cell, and a piece of the cell membrane (the 'patch') is drawn into the microelectrode tip; the glass tip of the micropipette forms a high resistance 'seal' with the cell membrane, then whole cell mode is entered by applying suction. Next, the pipette is moved away from the cell to form an outside-out patch. Examples of useful protocols may be found in *Single Channel Recording*, Plenum Press, B. Sakmann and E. Neher eds. This configuration can be used to study Kir channels present in the isolated patch of membrane. Variations of this technique include the "perforated patch" technique, or the patch of membrane can be pulled away from the rest of the cell.

As an example, for patch-clamp experiments in the outside-out mode, each oocyte will be incubated in a hypertonic solution containing 200 mM NaCl, 130 mM KCl, 5 mM $K_2EDTA$, 5 mM $K_2HPO_4$, 5 mM $KH_2PO_4$ pH 7.2 for 5-10 minutes and the vitelline membrane will be removed before seal formation. Currents will be recorded in either cell-attached or outside-out configuration with an Axopatch 200B amplifier, Digidata 1440A analogue-to-digital converter and pClamp10.1 software to control membrane voltage and record. During the current recordings, the membrane will be first held at 0 mV followed by a 10-second voltage ramp from +80 mV to −80 mV. The pipette solution will contain 140 mM KCl, 5 mM $K_2HPO_4$, 5 mM $KH_2PO_4$, 0.3 mM $CaCl_2$, 1 mM $MgCl_2$, pH 7.2 with KOH. The bath solution will contain 130 mM KCl, 5 mM $K_2EDTA$, 5 mM $K_2HPO_4$, 5 mM $KH_2PO_4$, pH 7.2 with KOH.

To measure a compound for activity, first a control current is measured while perfusing with the recording solution without the compound present. Then, a second current is recorded while perfusing with the solution and the compound of interest. Any difference in current levels indicates that the compound acts to modulate the activity of the Kir channel. An example of this type of assay may be found in Lu and MacKinnon 1997 Biochemistry, vol. 36, no. 23, pp. 6936-6940 or Namba et al., 1996 FEBS Letters vol. 386, pp. 211-214.

Planar Lipid Assay

Another electrophysiological assay which may be used in the present invention is a planar lipid bilayer assay. In this type of assay a lipid bilayer is created and the Kir channel protein is introduced into the lipid bilayer. A hydrophobic material such as Teflon is used to prepare the lipid bilayer by making a small hole (an aperture) in a sheet of Teflon. A syringe containing a solution of lipids dissolved in an organic solvent is introduced to the hole and a bilayer is formed in the center of the aperture, with solvent forming the perimeter of the newly formed bilayer.

The Teflon sheet provides a partition between two chambers allowing the placement of electrodes on both sides of the sheet. Preferably, the purified Kir channel is reconstituted into lipid vesicles and then fused with the bilayer after it is formed. The detergent coating facilitates insertion into the bilayer. (See U.S. Pat. No. 6,191,254 and Guillermo et al J. Membrane Biol (2008) 223: 13-26).

The amount of lipid desired (preferably PE:PG 3:1) is pipetted into a glass vial (about 5-10 mg). The lipid is dried under argon and then further under a room temperature vacuum for about 3 hours.

The lipid is rehydrated with hydration buffer (10 mM HEPES 7.4 (KOH), 450 mM KCl, 4 mM N-methylglucamine, 2 mM DTT) to a final lipid concentration of 10 mg/ml and vortexed briefly. The glass vial is flushed with argon and the lipid mixture is sonicated mildly, i.e., with short pulses of no longer than 30 seconds each. In between sonication pulses, the lipid mixture is cooled in a room temperature water bath to ensure that the lipid mixture does not get too hot. This procedure is repeated until the lipid mixture becomes translucent with a distinct pink shade.

A solution containing 50 mM DM in the hydration buffer is prepared. The DM solution is added to the lipid mixture to give a final concentration of 10 mM of DM and rotated at room temperature for 2 hours. To the detergent/lipid mixture, the Kir channel is added to the desired ratios (e.g., about 0.05-0.1). The concentration of DM is then raised to 17.5 mM and the mixture is rotated at room temperature for 1 hour. The detergent/lipid mixture is then put into dialysis tubing and dialysed against the hydration buffer.

Fluorescent Dye Assay

Another assay which may be used to identify compounds which specifically bind the Kir channel turret region is an assay utilizing a fluorescent dye. An example of a suitable dye is FluxOR™ available from Invitrogen (catalog nos. F10016, F10017). An example of this method is shown in FLOW-CHART 2.

The FluxOR™ reagent is a fluorogenic indicator dye, which is loaded into cells as a membrance-permeable Acetoxymethanol (AM) ester. According to the protocol, the FluxOR™ reagent is dissolved in DMSO and further diluted with the FluxOR™ assay buffer, a physiological Hank's balanced salt solution, for loading into cells. Pluronic® surfactants, which disperse and stabilize the dye are used to facilitate loading in aqueous solution.

Mammalian cells such as HEK, COS or CHO cells are grown in culture and incubated with the dye. Inside the cell, the non-fluorescent AM ester form of the FluxOR™ dye is cleaved by endogenous esterases into a flourogenic thallium-sensitive indicator. The thallium-sensitive form is retained in the cytosol and its extrusion is inhibited by water-soluble Probenecid, which blocks organic anion pumps. The dye-loading buffer is replaced with fresh, dye-free assay buffer, composed of physiological HBSS containing Probenecid, before the assay. During the assay, a small amount of thallium is added to the cells with a stimulus solution that opens potassium-permeant ion channels with a mild depolarization or agonist addition. Thallium then passes into cells through open potassium channels according to a strong inward driving force. Upon binding cytosolic thallium, the de-esterified FluxOR™ dye exhibits a strong increase in fluorescence intensity at its peak emission of 525 nm. Baseline and stimulated fluorescence is monitored in real time to give a dynamic, functional readout of thallium redistribution across the membrance with no interference from quencher dyes.

Inhibitors such as, for example, the compounds of the present invention may slow the rate of entry of thallium and thus reduce the onset of a fluorescent signal. This assay may be used for the selection of compounds that specifically bind to the turret regions of the Kir proteins. To identify such compounds a first group of cells would be transfected with wild type Kir channels and a second group of cells transfected with Kir channel having mutated turrets as illustrated in FLOWCHART 2. Test compounds such as the antibodies identified in the assays above would be added to the cells to screen for those compounds which inhibit or reduce the onset of fluorescence upon addition of the thallium dye due to inhibition of the channel. Compounds which reduced the rate of thallium intake in cells with normal turrets but had no effect on cells with mutant turrets would be classified as turret specific inhibitor compounds.

This assay may also be used to determine the specificity of the compounds for given turrets, in other words, the compounds may be introduced into cells which have been transfected with different versions of the Kir Channel to determine if the compound is specific for a given type of Kir Channel protein.

Assay for Selective Binding to Specific Types of Kir Channels

In order to determine whether a given antibody is specific for a given type of Kir Channel, assays such as an ELISA assay may be performed in which an antibody is tested against a variety of different Kir Channels to determine if the antibody is specific for a single type of Kir Channel. Ideally, antibodies that would be used as therapeutic compounds will bind to only one type of Kir channel in the turret region.

Methods to Identify Compounds to Treat Conditions

Compounds that bind to the turret region of a Kir channel and which modulate the ion channel activity of a Kir channel may be administered to a subject to determine if such compounds are able to treat a given condition. As an example, a compound may be administered to a subject such as a mammal with a given disease state using known methods of administration and the subject is then monitored clinically and tested using biochemical assays to determine if the compound is able to treat the condition using known assays for the disease state. It is believed that a variety of conditions may be treated with the compounds of the present invention, including, but not limited to, diabetes mellitus, hypertension, cardiac arrhythmia and epilepsy.

The present invention may be better understood by reference to the following non-limiting example, which is provided as exemplary of the invention. This example should in no way be construed, however, as limiting the broad scope of the invention. Example 1, which follows below, provides the first determination of the crystal structure of a euraryotic Kir channel protein and identification of the structured turret region present in Kir channel proteins. (See *Crystal Structure of the Eukaryotic Strong Inward-Rectifier $K^+$ Channel Kir2.2 at 3.1 Å Resolution*, X. Tao, J. L. Avalos, J. Chen and R. MacKinnon, *Science* 2009 Dec. 18; 326 (5960); 1668.)

Example 1

Crystal Structure of the Eukaryotic Strong Inward-Rectifier $K^+$ Channel Kir2.2 at 3.1 Å Resolution Inward-rectifier $K^+$ channels conduct $K^+$ ions most efficiently in one direction, into the cell. Kir2 channels control the resting membrane voltage in many electrically excitable cells and heritable mutations cause periodic paralysis and cardiac arrhythmia. We present the crystal structure of Kir2.2 from chicken, which, excluding the unstructured N- and C-termini, is 90% identical to human Kir2.2. Crystals containing $Rb^+$, $Sr^{2+}$ and $Eu^{3+}$ reveal binding sites along the ion conduction pathway that are both conductive and inhibitory. The sites correlate with extensive electrophysiological data and provide a structural basis for understanding rectification. The channel's extracellular surface, with large structured turrets and an unusual selectivity filter entryway, might explain the relative insensitivity of eukaryotic inward rectifiers to toxins. These same surface features also suggest a possible approach to the development of inhibitory agents specific to each member of the inward-rectifier $K^+$ channel family.

A crystal structure reveals the structural basis of diode-like conduction properties and relative toxin insensitivity in inward rectifier $K^+$ channels.

Introduction

In 1949 Bernard Katz introduced the term 'anomalous rectification' to distinguish the $K^+$ currents he observed in frog skeletal muscle from the 'delayed rectification' $K^+$ currents of the squid axon action potential (1, 2). Today we know that 'delayed rectifiers' are a subset of the large family of voltage-dependent $K^+$ (Kv) channels, while 'anomalous rectifiers' are members of a different family of channels more commonly known as inward rectifier $K^+$ (Kir) channels (3). The name inward rectifier refers to a fundamental ion conduction property exhibited to a greater or lesser degree by all members of the family: given an equal but opposite electrochemical driving force, $K^+$ conductance into the cell far exceeds conductance out of the cell. Thus, Kir channels are analogous to one-way conductors, or diodes, in solid-state electronic devices.

Electrophysiological experiments have shown that inward rectification is a consequence of voltage-dependent pore blockage by intracellular multivalent cations, especially $Mg^{2+}$ and polyamines (4-8). At internal negative (hyperpolarizing) membrane voltages the blocking ions are cleared from the pore so that $K^+$ conducts, whereas at internal positive (depolarizing) membrane voltages the blocking ions are driven into the pore from the cytoplasm so that $K^+$ conduction is blocked. As a result, Kir channels are conductive when an excitable cell is at rest and non-conductive during excitation. This property is thought to foster energy efficiency because it enables Kir channels to regulate the resting membrane potential, but not dissipate the $K^+$ gradient during an action potential (3).

A central mechanistic question is why are Kir channels blocked by intracellular multivalent cations? Mutational studies have identified several amino acids that confer sensitivity to blocking ions (9-19), but a structural description of these sites has remained elusive. Structures of prokaryotic Kir channels, due to their low sequence similarity to eukaryotic Kir channels, do not contain the specific amino acids that are known to underlie blockage and rectification (20, 21).

Another longstanding puzzle in eukaryotic Kir channel studies is their relative insensitivity to natural toxins that typically inhibit other $K^+$ channels (22-24). Snake, spider and scorpion venoms, for example, contain numerous toxins against various Kv channels and $Ca^{2+}$-activated $K^+$ channels (25-27). By contrast, Kir channel toxins are rare, and no specific toxins against Kir2 channels have been discovered.

Results and Discussion

Eukaryotic Kir channels as a Molecular Family

The eukaryotic Kir channels contain several amino acid sequence motifs and conserved amino acids that are essential to their functional properties (FIGS. 1A-1C). For example, in most other $K^+$ channels the selectivity filter comprises the 'canonical' filter sequence TXGYGDX, where X represents an aliphatic amino acid (FIGS. 1A-1C). The corresponding sequence in eukaryotic Kir channels is TXGYGFR, with F sometimes replaced by another amino acid. In light of the structural importance of DX in the canonical sequence, the amino acids FR signify a marked variation on the filter sequence. Eukaryotic Kir channels also contain an absolutely conserved pair of cysteine residues flanking the pore-region, which is the re-entrant peptide segment that forms the pore-helix and selectivity filter of $K^+$ channels. Between the outer helix (the first transmembrane segment) and pore-region the 'turret', though varied amongst inward rectifiers, contains the sequence HGDL that could be considered a signature of eukaryotic Kir channels. Finally, through extensive studies combining electrophysiology and mutagenesis several acidic amino acids (D and E) are known to be critical to inward rectification (9-19), and motifs containing basic amino acids (e.g. PKKR) are critical to $PIP_2$ activation of Kir channels (28-35). These positions are enclosed in boxes on the sequences in FIGS. 1A-1C.

Figure 6A:
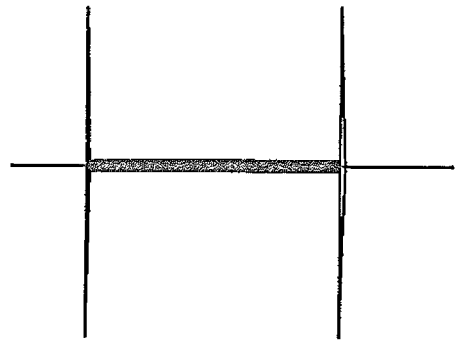
FIG. 6A-6D results showing the chicken Kir2.2 channel is a strong inward rectifier.
Figure 6B:
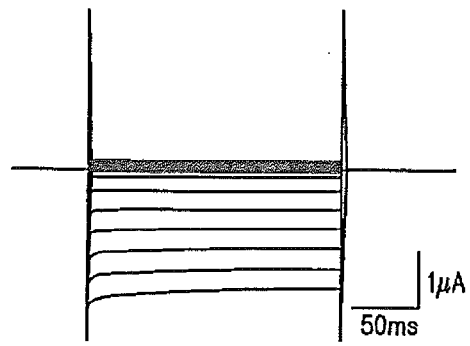
Figure 6C:
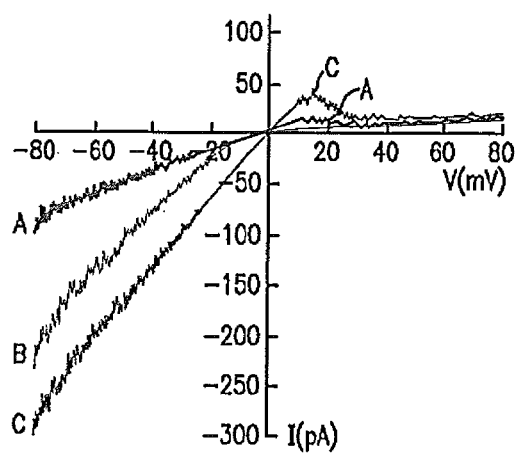
Figure 6D:
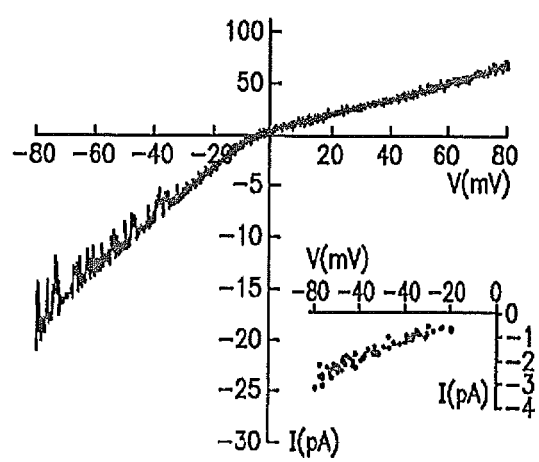

The Kir2.2 channel from chicken is 90% identical to the human ortholog (excluding the N- and C-termini) and contains all of the sequence characteristics of a strong inward rectifier (36). FIGS. 6A-6D shows that the chicken Kir2.2 channel expressed in *Xenopus* oocytes indeed functions as a strong rectifier. In oocyte two-electrode voltage clamp recordings with 98 mM KCl in the bath solution inward currents are much larger than outward currents (FIG. 6B). In on-cell and excised gigaseal patch recordings channel activity is observed at hyperpolarizing (negative internal) membrane voltages but not at depolarizing (positive internal) voltages (FIG. 6C). The single channel conductance measured near −80 mV is approximately 40 pS, which is very similar to the values reported for the guinea pig and mouse Kir2.2 channels (37, 38) (FIG. 6D, inset). The sharp transition between channel conductance and non-conductance as a function of membrane voltage is characteristic of a strong rectifier (36). Note that upon patch excision from the oocyte surface some outward current is observed at voltages slightly positive to the reversal potential because the concentration of intracellular blockers is decreased (FIG. 6C, trace labeled (C)). However, the current still decreases with further depolarization (negative conductance) as channels become blocked in a voltage-dependent manner: this behavior reflects the inherent difficulty in washing away trace yet still active concentrations of polyamine molecules due to their very high affinity for the pore in strong rectifiers (39, 40). Several minutes following patch excision the currents decrease (FIG. 6C, trace labeled (A)). This 'run-down' reflects altered channel regulation mediated by kinases, phosphatases and lipid signaling (34, 36, 41, 42).

Figure 2A:
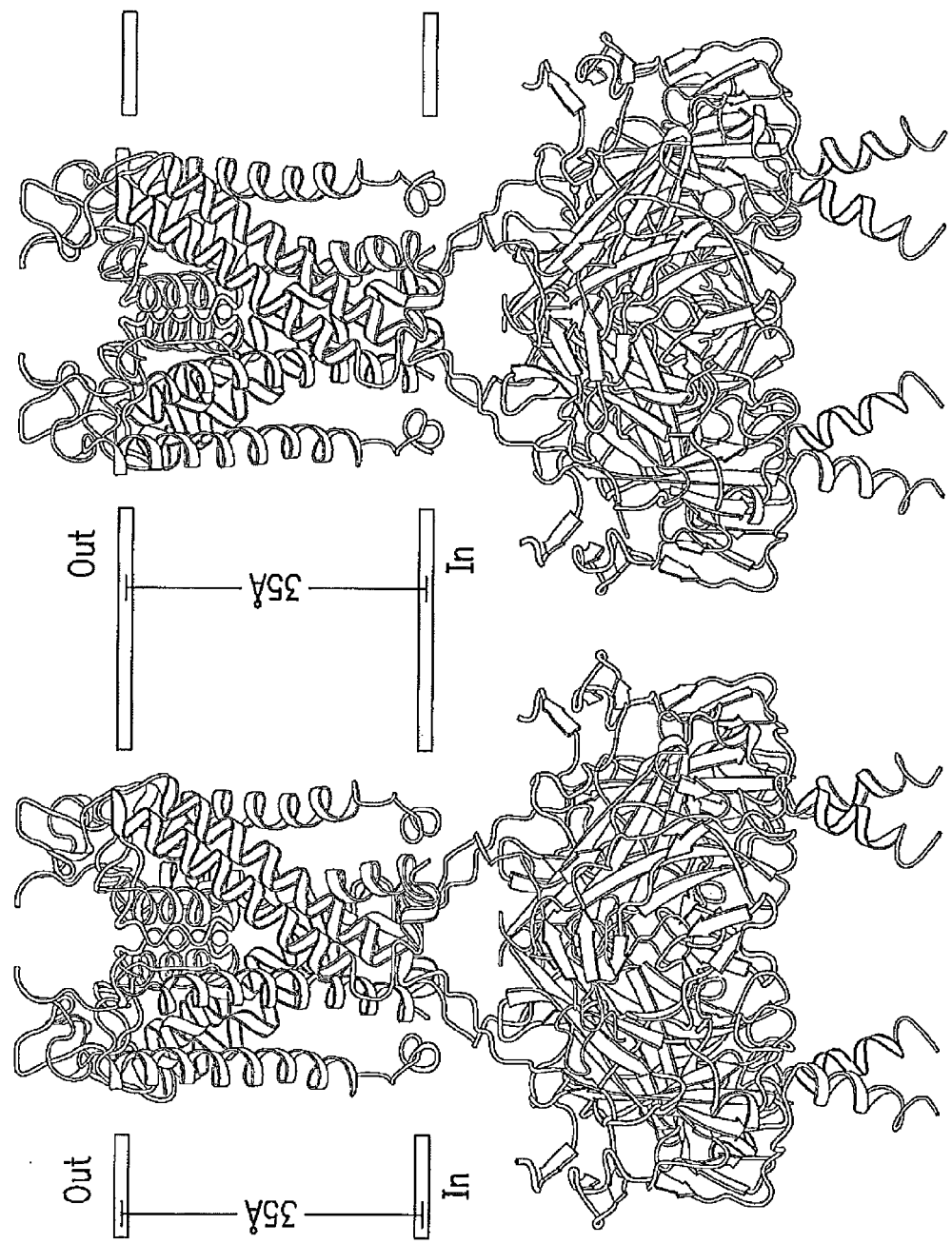
FIG. 2A-2E illustrates a structure of Kir2.2.
Figure 7:
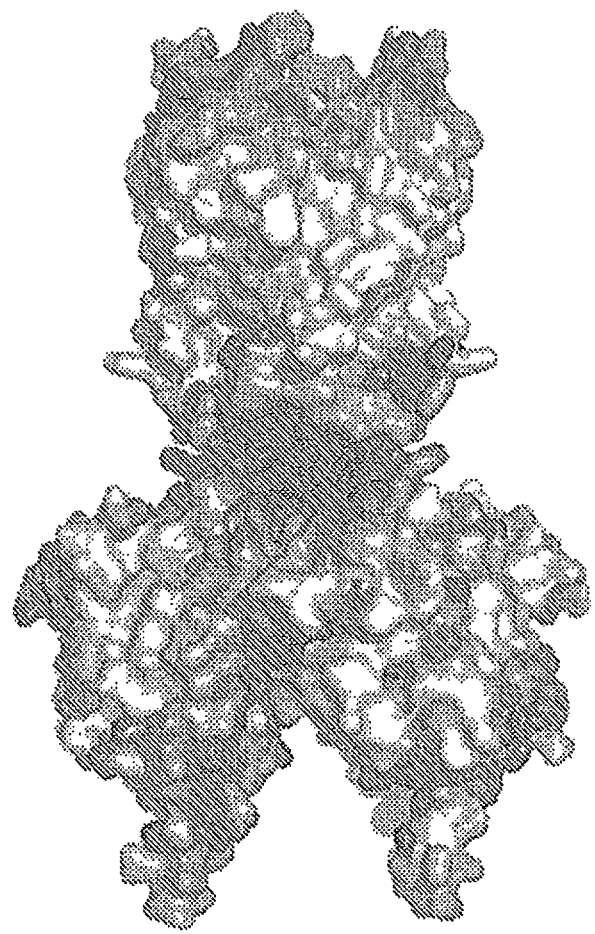
FIG. 7 provides a surface representation of Kir2.2, viewed from the side with the extracellular side above. The surface is shaded for qualitative assessment of the negative and positive electrostatic potential at the surface.

In order to obtain diffracting crystals the intrinsically disordered N- and C-terminal regions were removed. The electrophysiological recordings shown in FIGS. 6A-6D were made using a similar construct with N- and C-terminal truncations, confirming that the crystal structure corresponds to a functional channel unit with strong rectifying properties. The Kir2.2 model, consisting of the cytoplasmic domain and transmembrane channel, was refined at 3.1 Å to a free R-factor of 0.27. A ribbon diagram in stereo shows the transmembrane pore (above) and the cytoplasmic pore (below) (FIG. 2A). Lateral openings between the transmembrane and cytoplasmic pores, at the level of the lipid membrane headgroup layer, contain many arginine and lysine residues. The high density of positive charges makes it unlikely that $K^+$ ions would pass through these openings (FIG. 7). In FIG. 7 the shading at the top of the Figure illustrates a negative electrostatic potential at the surface and the darker shaded region in the center of the Figure illustrates regions of positive electrostatic potential. The structure is therefore consistent with mutagenesis studies, which support the conclusion that the ion pathway extends across the full length of the transmembrane and cytoplasmic pores (9-19). The overall architecture is similar to prokaryotic Kir channels but with a notable difference: the Kir2.2 channel contains prominent, highly structured turrets on the extracellular face of the channel. These surround as if to protect the pore entryway.

The Selectivity Filter

Figure 2B:
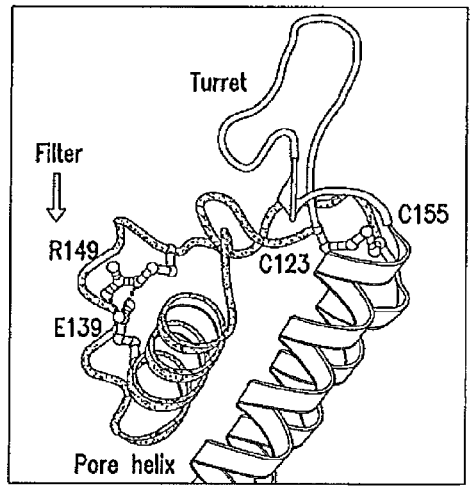

At a detailed structural level Kir2.2 is quite different from prokaryotic Kir channels owing to minimal (<20%) sequence conservation. The cysteine pair that is absolutely conserved among eukaryotic Kir channels creates a circularized pore region through covalent linkage of the segment preceding the pore helix (C123) to the segment following the selectivity filter (C155) (FIG. 2B). The existence of a disulfide bond was correctly predicted on the basis of mutagenesis studies: mutation of the corresponding cysteines in Kir2.1 led to the absence of currents even though expressed protein was detectable by Western Blot analysis (43, 44), Application of 10 mM DTT or reduced glutathione to the outside of cells expressing the wild-type channels did not affect currents. From these two observations it was concluded that a disulfide bridge must be essential for proper folding, but apparently not for function (43, 44). The structure provides an alternative interpretation. The disulfide bridge is buried beneath the protein surface at the level of the membrane interface. Furthermore, the Kir2.2 channel was purified and crystallized in the presence of 20 mM DTT and 3 mM TCEP, and yet the disulfide bridge remained intact. It is therefore possible that the disulfide bridge remains intact upon exposure to moderate concentrations of DTT, and that the bridge may be important for channel function.

Figure 2C:
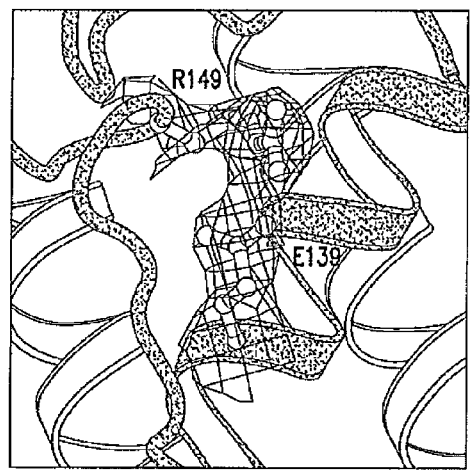

The pore region is further stapled together by an ionized hydrogen bond between R149 in the filter sequence TXGYGFR and E139 (FIGS. 2B and 2C). The Glu O-ε to Arg N-η distance is 2.4 Å, compatible with an energetically strong interaction. Mutations altering this interaction are known to alter channel function (45, 46). On the basis of studies with concatenated subunits the salt bridge was thought to be inter-subunit, but the crystal structure shows that this interaction ties together two segments of the pore-region within a single subunit (46).

Figure 2D:
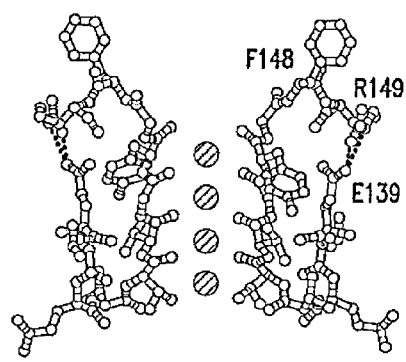
Figure 2E:
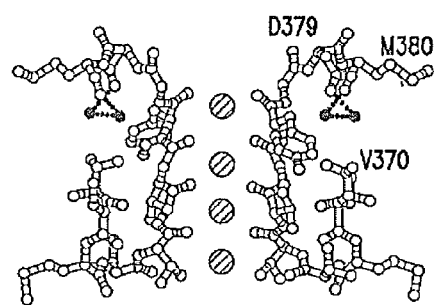

Despite the presence of substantially different protein contacts surrounding the selectivity filter, the main-chain structure of the filter in Kir2.2 is the same as in other $K^+$ channels (47). For example, the main chain RMSD between Kv1.2 and Kir2.2 is 0.4 Å, which is within the margin of certainty to discriminate atomic positions with 3.1 Å diffraction data (FIGS. 2D and 2E) (20, 48, 49). One structural difference near the filter could possibly account for important pharmacological differences between Kir and other $K^+$ channels. In the canonical filter sequence the Asp (D) residue in the filter sequence is buried, creating a flat surface surrounding the filter opening. By contrast, in Kir channels the Phe (F) residue at the corresponding position projects directly into aqueous solution, creating four protrusions on the perimeter where the filter opens to the extracellular solution.

The Cavity and Gates

The pore lining on the intracellular side of the selectivity filter is mainly hydrophobic in nearly all $K^+$ channels. Eukaryotic Kir channels are an exception in which the central region of the pore—known as the central cavity—contains four polar amino acids (one from each subunit) projecting toward the ion pathway (FIG. 3A). In Kir2.2 and other strong rectifiers these polar amino acids are Asp (D173), whereas in weak rectifiers such as Kir1.1 and Kir6.1 they are Asn (FIG. 1A-1C). On the basis of electrophysiological studies, Asp residues in the central cavity of strong rectifiers are hypothesized to influence the affinity of $Mg^{2+}$ and polyamines by an electrostatic mechanism (12, 18).

Beneath the central cavity, residues I177 and M181 on the inner helices form two hydrophobic seals that close off the pore leading to the cytoplasm (FIG. 3C). Kir2.2 is therefore physically shut at the 'activation gate' (50). Amino acids corresponding to positions 177 and 181 are also large and hydrophobic in most other eukaryotic Kir channels, but not in many other $K^+$ channels (FIGS. 1A-1C). For example, in KcsA, Kv channels and prokaryotic Kir channels, the position corresponding to 177 usually contains a small and sometimes polar amino acid, typically Ala or Thr. In KcsA both seal positions contain small amino acids (FIG. 3D). Because of the large hydrophobic residues at positions 177 and 181, the inner helices of Kir2.2 do not come as close together in the closed conformation as in KcsA (FIGS. 3C and 3D).

FIG. 3E shows the cytoplasmic domain tetramer from the Kir2.2 channel superimposed onto the domain from Kir2.1, which was solved by crystallography in the absence of a transmembrane channel (11). Over most of the domain these structures are nearly identical. This observation supports the expectation (based on 80% sequence identity) that Kir2.2 should represent an excellent model for the complete Kir2.1 channel. In addition to the activation gate formed by the transmembrane inner helices, Kir channels have been proposed to have a second gate (G-loop) at the apex of the cytoplasmic domain tetramer (11, 51). The G-loop is physically open in Kir2.2 and closed in the Kir2.1 domain (FIGS. 3F and 3G). The differences in conformation are due to local movements of the G-loop rather than rigid body motions of the cytoplasmic domains. Local G-loop movements contrast observations on the cytoplasmic domain of Kir3.1, in which G-loop opening appears associated with rigid body movements of domains in the tetramer (20).

Ion Binding Sites for Conduction and Inward Rectification

Figure 4A:
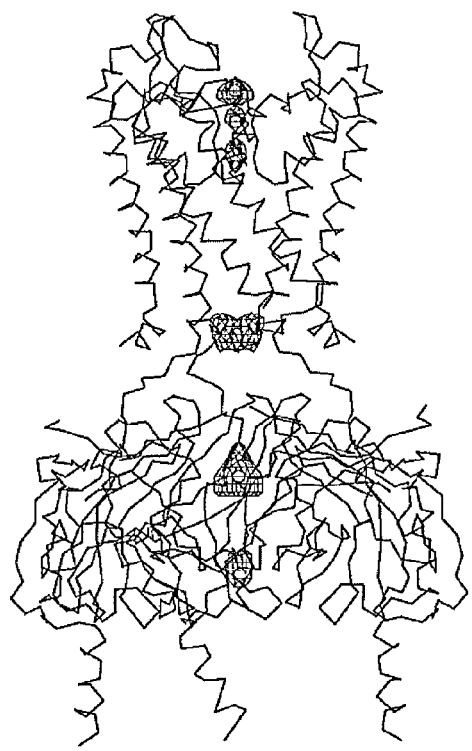
FIG. 4A-4F illustration of ion binding sites.
Figure 8:
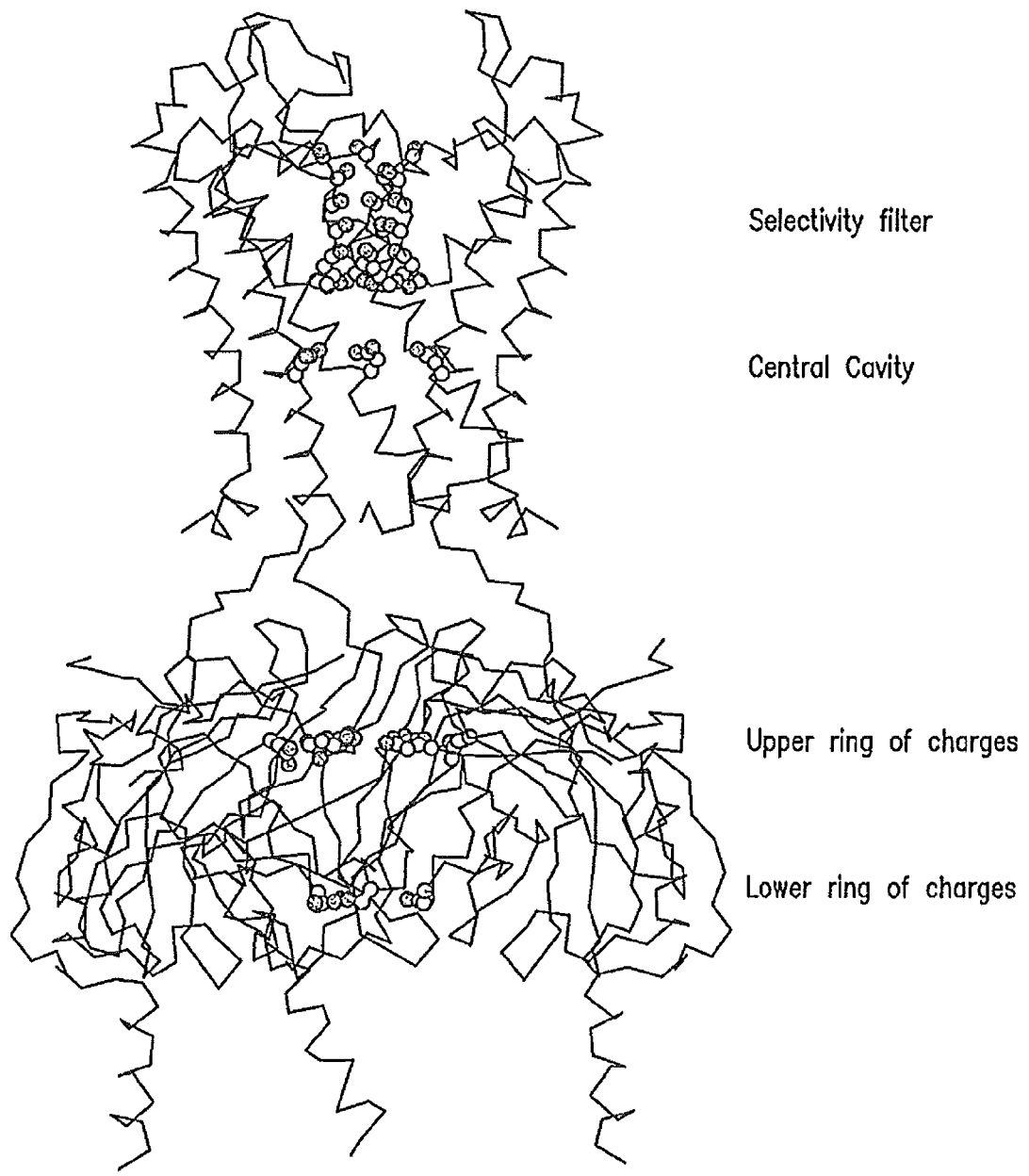
FIG. 8 illustrates ion binding sites of Kir2.2 in the slectivity filter, central cavity, upper and lower rings of charges are shown as sticks (oxygens and stippled). The channel is represented as a α-carbon trace with the transmembrane domain and cytoplasmic domain closest to viewer removed for clarity.
Figure 9:
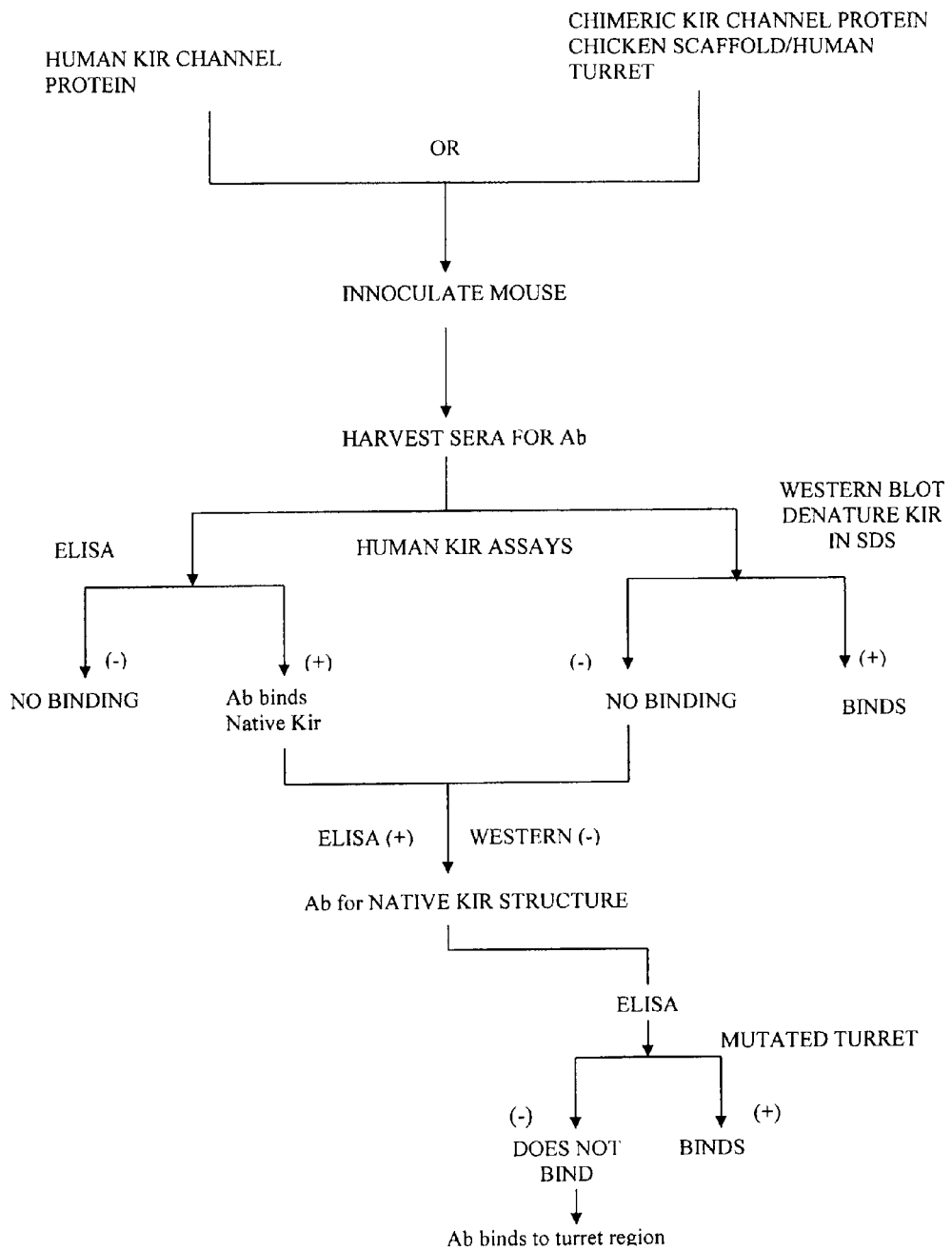
FIG. 9 depicts FLOWCHART 1, which illustrates a first ELISA assay is performed to identify antibodies that bind to the Kir channel protein.

FIG. 4A-F shows the locations of ions in difference Fourier maps from crystals containing $Rb^+$, $Sr^{2+}$, and $Eu^{3+}$. $Rb^+$ is a $K^+$ analog that conducts. Density for this ion is observed at multiple sites in the selectivity filter and at three positions within the pore on the intracellular side of the selectivity filter, but is absent in the central cavity (FIG. 4A). The three occupied intracellular positions are: immediately internal to the activation gate in the transmembrane pore, in the cytoplasmic pore internal to the G-loop, and at the entryway to the cytoplasmic pore. We refer to the two sites in the cytoplasmic pore as the upper and lower rings of charges, respectively (FIG. 8). The presence of multiple sites along the pore occupied by conducting ions area prerequisite for strong voltage-dependent block by intracellular cations that cannot pass through the selectivity filter (12, 52-57).

Crystals of Kir2.2 were grown in the presence of 650 mM $Rb^+$ and yet electron density for $Rb^+$ is not observed in the cavity (FIG. 4A). This finding is noteworthy because under similar conditions a strong monovalent cation peak is observed in the cavity of KcsA (47, 58). Native crystals of Kir2.2, grown in the presence of 150 mM $K^+$ and 500 mM $Na^+$, show a weak electron density peak at the cavity center with additional peaks on the perimeter, apparently bridging toward the D173 side-chain (FIG. 3A). We can not discern whether these peaks represent a disordered ion, multiple ions, or a low occupancy $K^+$ (or $Na^+$) in the center, perhaps surrounded by water molecules hydrogen bonded to the Asp carboxylate. We can conclude, however, that the central cavity in Kir2.2, at least in the closed conformation, has cation attractive properties that are different from KcsA.

Figure 4B:
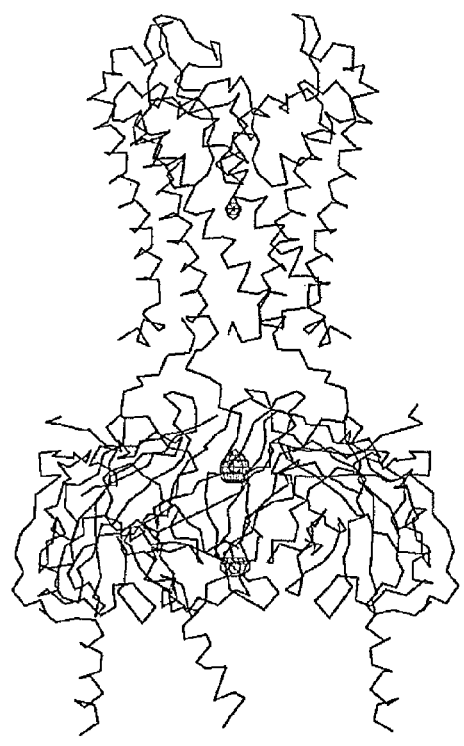
Figure 4C:
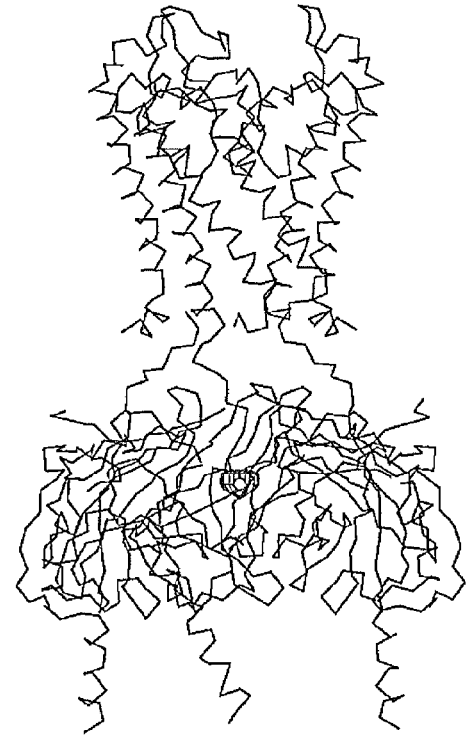
Figure 4D:
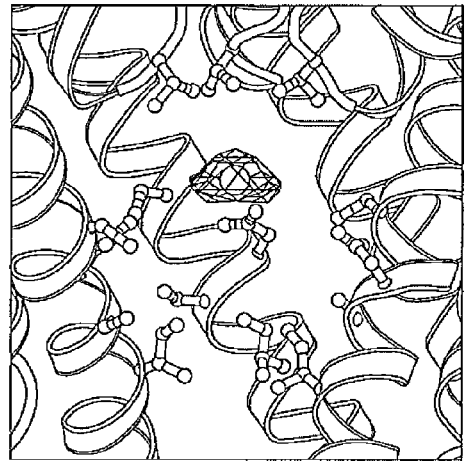
Figure 4E:
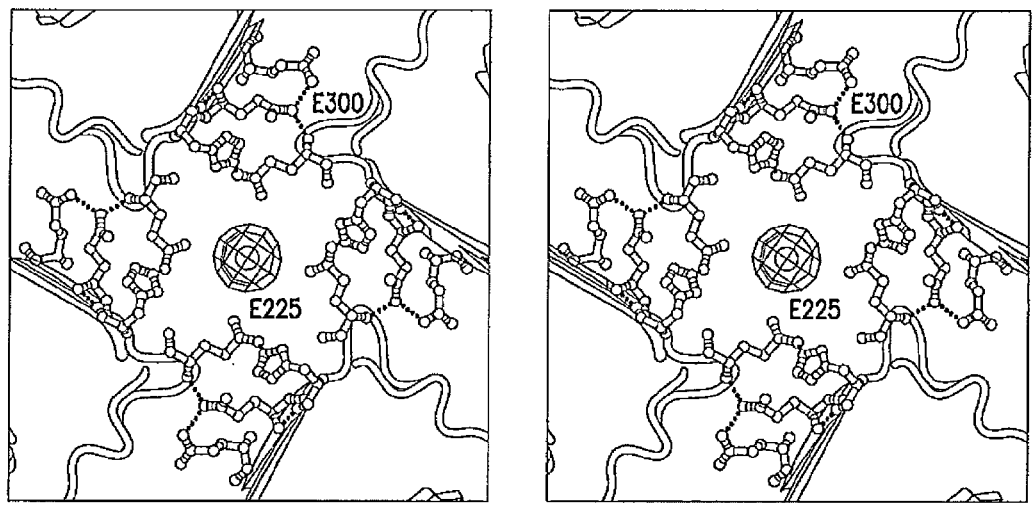
Figure 4F:
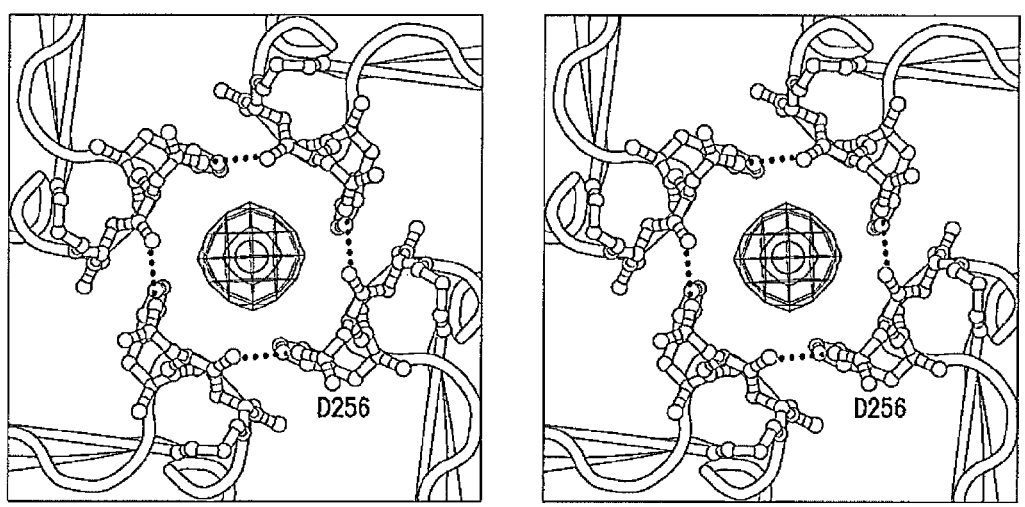

The divalent cation $Sr^{2+}$ should behave as an electron dense mimic of $Mg^{2+}$, a biologically important metal ion inhibitor of eukaryotic Kir channels (7, 8). In $F_o$-$F_c$ Fourier maps from crystals with 10 mM $Sr^{2+}$, 500 mM $Na^+$ and 150 mM $K^+$, density peaks due to $Sr^{2+}$ are observed at three sites inside the pore intracellular to the selectivity filter: in the cavity, at the upper ring and at the lower ring of charges (FIGS. 8 and 4B). The magnitude of the $Sr^{2+}$ peak is small in the cavity (3,4σ) compared to the peaks at the upper (9.6σ) and lower (7.2σ) rings of charges. Separate experiments with crystals containing 200 mM $Sr^{2+}$ support that the weak cavity peak is indeed due to $Sr^{2+}$, which is present apparently at relatively low occupancy. Detailed views of these sites are shown (FIGS. 4D-F). They each consist of planar rings of acidic amino acids arranged on the pore's perimeter. All three sites exhibit a preference for $Sr^{2+}$: 10 mM $Sr^{2+}$ out competes 150 mM $K^+$. This selectivity is likely to be electrostatic in origin. The sites are too wide (10.5 Å, 8.9 Å and 9.3 Å diameter for the cavity, upper and lower ring of charges) to mediate direct coordination of an ion at the center. Presumably ions at the center of these sites interact through bridging water molecules. Since each site has the potential to contain multiple negatively charged carboxyl groups, the resulting strong electric field is expected to create a good match for a multivalent cation. Crystals containing the lanthanide $Eu^{3+}$, which we assume to be trivalent (59), provide support for this hypothesis. An anomalous difference Fourier map shows that $Eu^{3+}$ binds at only one site, the upper ring of charges. This site appears to be more electronegative than the others because it contains two concentric rings of acidic amino acids, E225 and E300.

Mutagenesis studies have identified several amino acids that, when mutated, affect the affinity of $Mg^{2+}$ and polyamines in strong rectifiers. D173 in the cavity, E225 and E300 forming the upper ring of charges, and D256 forming the lower ring of charges are among those known to be important (9-19). The weak $Sr^{2+}$ peak in the cavity might seem incompatible with the large influence that mutations of the cavity Asp (D173) have on $Mg^{2+}$ affinity. However, the channel in the crystal is not in an applied electric field: in an electric field imposed by a depolarized (positive inside) membrane we expect that the distribution of blocker occupancies among the multiple sites will change. Specifically, we expect the blocking cations to be driven deeper into the pore toward the cavity. In correlating the crystallographic with electrophysiological data, it is most significant that the amino acids forming the $Sr^{2+}$ sites in the crystal are the same amino acids that are known to affect blockage and rectification in electrophysiology experiments (36). Beyond providing a structural basis with which to explain past electrophysiological studies, the Kir2.2 structure also suggests many new experiments. For example, most studies on the mechanism of rectification have focused on electrostatic interactions between the positively charged blocker and negatively charged groups on the protein. But hydrophobic interactions between methylene groups of polyamine molecules and hydrophobic residues in the channel may be important. In particular, we might anticipate that when the pore opens polyamines could interact strongly with the large hydrophobic amino acids at positions 177 and 181 when the leading amino group of the polyamine reaches into the central cavity (FIG. 3C) (54).

Since the earliest investigations of strong inward rectifiers two important properties have been noted: a sharp transition from a conductive state to a non-conductive (blocked) state over a very narrow voltage range, and a dependence of the transition on the extracellular $K^+$ concentration (60-63). Specifically, the voltage at which the transition occurs shifts to more depolarizing values as extracellular $K^+$ concentration is increased. Both properties, the sharp transition (i.e. strong voltage dependence) and its dependence on extracellular $K^+$, have been attributed to the simple notion that conducting ions and blocking ions compete for sites in the pore (12, 52-57, 64-66). The crystallographic data presented here support this conclusion. We observe in the crystal $Rb^+$ binding at the same sites that can bind multivalent blocking ions. Therefore a high extracellular $K^+$ (or $Rb^+$) concentration should favor occupation of the sites by conducting ions, and a more depolarizing voltage should be required to drive blocking ions into the pore from the cytoplasm to replace the conducting ions. Moreover, as blocking ions enter the pore from the intracellular side, the displaced conducting ions must move through the selectivity filter to the extracellular side. This is to say that movements of blocking and conducting ions must be coupled. Such coupling would have energetic consequences because movement of an ion across the membrane voltage difference constitutes work. In other words a blocking ion entering the pore will exhibit a voltage dependence that results from a combination of its own charge and the charge of the displaced ions. This can be the origin of strong voltage dependent block, which can be the origin of a biologically important property of strong rectifiers—their diode property of a sharp transition from a conductive to a non-conductive state as a function of membrane voltage (12, 52-55, 64).

The Extracellular Pore Entryway and Pharmacology of Kir Channels

Figure 5A:
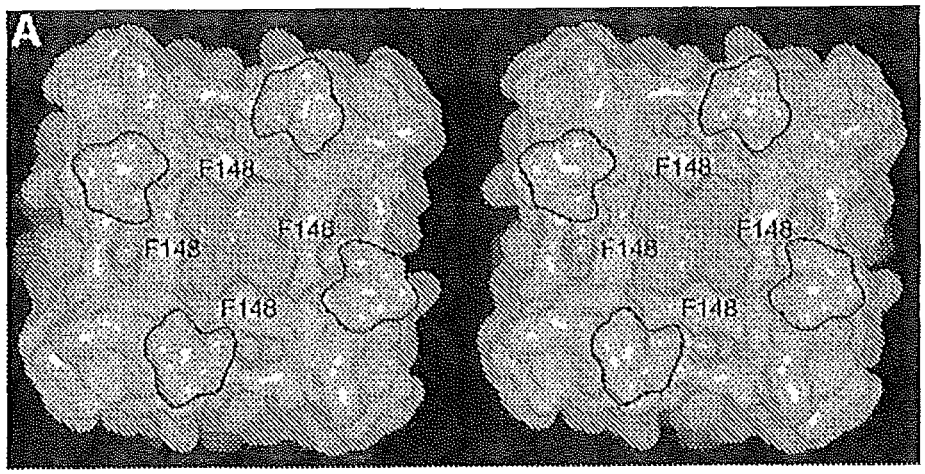
FIG. 5A-5D illustrates the unique structure of the extracellular entryway.
Figure 5B:
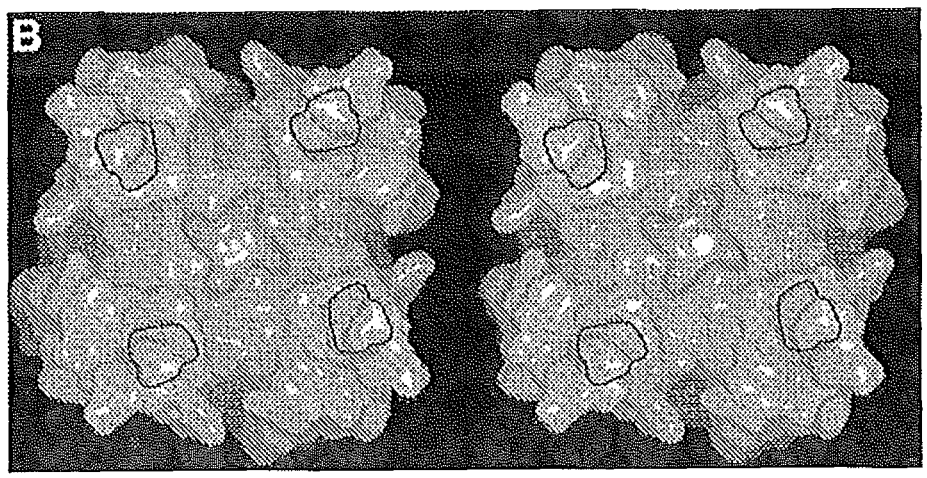

Two aspects of the structure may account for the fact that eukaryotic Kir channels, especially members of the Kir2 subfamily, are relatively insensitive to $K^+$ channel toxins (22-24). The turrets in Kir2.2 are larger and come closer together, constricting the pore entryway compared to Kv1.2; and F148 in the sequence TXGYGFR creates four protrusions on the surface at the pore opening (FIGS. 5A and 5B). Thus, in Kv channels the entryway is wider and the pore opens onto intersecting grooves with a flat base, which form the docking surface for pore-blocking scorpion toxins (FIG. 5B). In Kir2.2 the entryway is constricted and the grooves are absent (FIG. 5A).

Though the shape of the eukaryotic Kir channel pore entryway might offer fewer opportunities for inhibitory protein-protein interactions, inhibition might occur by a somewhat different strategy. Inhibitors of Kir1.1 and Kir3.4 channels have been identified. A bee venom toxin, tertiapin, inhibits both of these channels (22). At 21 amino acids tertiapin is smaller than most other venom toxins so it might fit between the turrets more effectively. Alternatively, the turrets themselves might form the binding site for tertiapin (67-69). At 57 amino acids δ-dendrotoxin from the green mamba snake is rather large and yet it inhibits Kir1.1 channels (23). Compared to tertiapin less is known about the binding site on the channel for δ-dendrotoxin, but one aspect of its inhibition is intriguing: the blocked state reduces single channel conductance to about 10% rather than inhibiting all the way. δ-dendrotoxin most likely binds to the turrets but is too large to fit tightly over the pore, which would imply that binding to the turret may be sufficient to alter the channel's function.

Figure 5C:
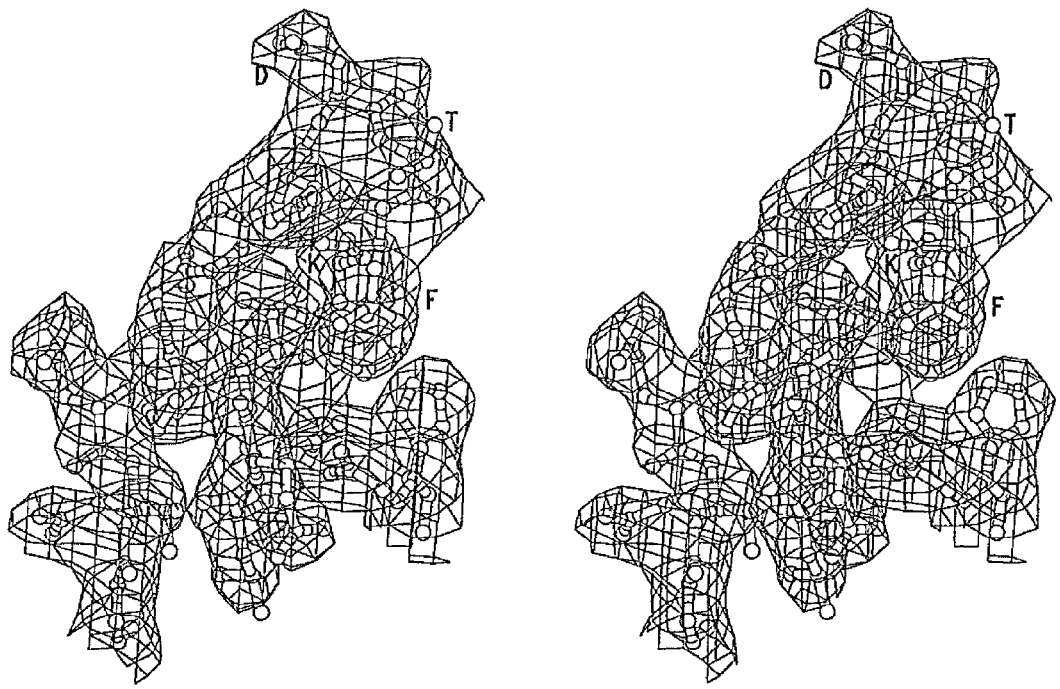
Figure 5D:
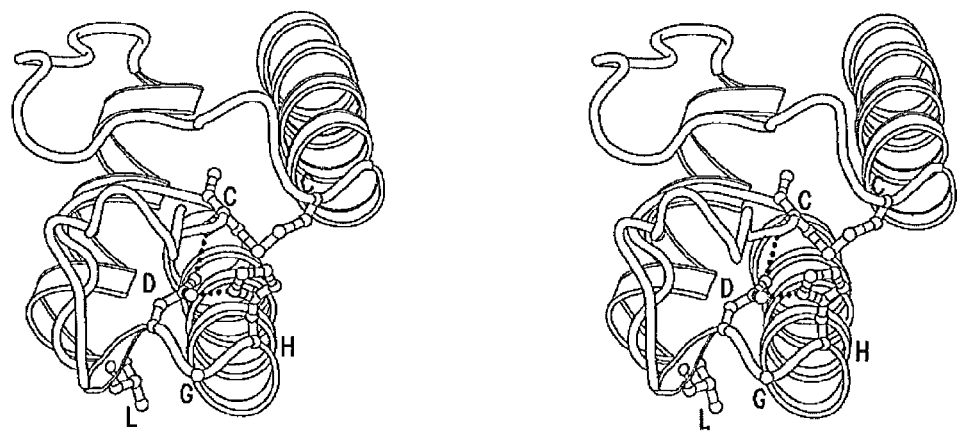

The idea that binding to the turrets could alter function is not surprising when one considers that the turret in Kir2.2 is not a loop, but forms a highly ordered structure (FIG. 5C). The base of the turret is formed and pinned together by the HGDL sequence, which with only minor variation is found in all eukaryotic Kir channels (FIGS. 1A-1C and FIG. 5D.) H108 stabilizes D110 through a hydrogen bond. The Asp (D) itself is hydrogen bonded to the amide nitrogen of C123, which effectively holds the two ends of the turret together. L111 projects from the surface of a short $3_{10}$ helix into the protein interior to make stabilizing hydrophobic interactions. Thus, the turrets are structurally important elements of the channel. Between the sequence HGDL and the first Cys of the disulfide bridge the turret sequence is highly variable among Kir channel subtypes. The Kir2.1 channel becomes sensitive to tertiapin if the variable sequence is mutated to be Kir3.4-like (68). Therefore, the turrets appear to be structures through which specific inhibition of Kir channel subtypes might be achievable through directed evolution of specific protein binding partners.

SUMMARY

This presents the atomic structure of a eukaryotic Kir channel, Kir2.2, a strong inward rectifier. The sequence TXGYGFR gives rise to a $K^+$ selectivity filter stabilized by disulfide bridges and salt bridges that distinguish eukaryotic Kir channels. Multiple ion binding sites on the intracellular side of the selectivity filter can be occupied by conducting ions but exhibit higher affinity for multivalent blocking ions. Thus, blocking ions entering from the cytoplasm must displace conducting ions through the pore. This situation is expected to give rise to strong voltage-dependent block and diode-like conduction properties. Structural features of the extracellular pore entryway offer an explanation for the relative insensitivity of Kir channels to venomous toxins and a possible approach to the development of selective Kir channel inhibitors.

REFERENCES AND NOTES

1. H. A. Hodgkin A L, Katz B, *Archives des Sciences Physiologiques* 3, 129 (1949).
2. B. Katz, *Arch. Sci. Physiol.* (Paris) 3, 285 (1949).
3. B. Hille *Ion Channels of Excitable Membranes*. (Sinauer Associates, Inc., Sunderland, M A, 2001).
4. B. Fakler et al., *Cell* 80, 149 (Jan. 13, 1995).
5. A. N. Lopatin, E. N. Makhina, C. G. Nichols, *Nature* 372, 366 (Nov. 24, 1994).
6. M. Horie, H. Irisawa, A. Noma, *J Physiol* 387, 251 (June, 1987).
7. H. Matsuda, A. Saigusa, H. Irisawa, *Nature* 325, 156 (Jan. 8-14, 1987).
8. C. A. Vandenberg, *Proc Natl Acad Sci USA* 84, 2560 (April, 1987).
9. H. T. Kurala, W. W. Cheng, C. Arrabit, P. A. Slesinger, C. G. Nichols, *J Gen Physiol* 130, 145 (August, 2007).
10. Y. Fujiwara, Y. Kubo, *J Gen Physiol* 127, 401 (April, 2006).
11. S. Pegan et al., *Nat Neurosci* 8, 279 (March, 2005).
12. D. Guo, Z. Lu, *J Gen Physiol* 122, 485 (November, 2003).
13. Y. Kubo, Y. Murata, *J Physiol* 531, 645 (Mar. 15, 2001).
14. J. Yang, Y. N. Jan, L. Y. Jan, *Neuron* 14, 1047 (May, 1995).
15. M. Taglialatela, E. Ficker, B. A. Wible, A. M. Brown, *EMBO J* 14, 5532 (Nov. 15, 1995).
16. B. A. Wible, M. Taglialatela, E. Ficker, A. M. Brown, *Nature* 371, 246 (Sep. 15, 1994).
17. P. R. Stanfield et al., *J Physiol* 478 (Pt 1), 1 (Jul. 1, 1994).
18. Z. Lu, R. MacKinnon, *Nature* 371, 243 (Sep. 15, 1994).
19. B. Fakler et al., *FEBS Lett* 356, 199 (Dec. 19, 1994),
20. M. Nishida, M. Cadene, B. T. Chait, R. MacKinnon, *EMBO J* 26, 4005 (Sep. 5, 2007).
21. A. Kuo et al., *Science* 300, 1922 (Jun. 20, 2003),
22. W. Jin, Z. Lu, *Biochemistry* 37, 13291 (Sep. 22, 1998).
23. J. P. Imredy, C. Chen, R. MacKinnon, *Biochemistry* 37, 14867 (Oct. 20, 1998).
24. Z. Lu, R. MacKinnon, *Biochemistry* 36, 6936 (Jun. 10, 1997).
25. A. L. Harvey, B. Robertson, *Curr Med Chem* 11, 3065 (December, 2004).
26. K. J. Swartz, R. MacKinnon, *Neuron* 15, 941 (October, 1995).
27. M. L. Garcia, M. Hanner, H. G. Knaus, R. Slaughter, G. J. Kaczorowski, *Methods Enzymol* 294, 624 (1999).
28. D. Schulze, T. Krauter, H. Fritzenschaft, M. Soom, T. Baukrowitz, *J Biol Chem* 278, 10500 (Mar. 21, 2003).
29. W. Z. Zeng, H. H. Lieu, U. M. Krishna, J, R, Faick, C. L. Huang, *Am J Physiol Renal Physiol* 282, F826 (May, 2002).
30. C. M. Lopes et al., *Neuron* 34, 933 (Jun. 13, 2002).
31. M. Soom et al., *FEBS Lett* 490, 49 (Feb. 9, 2001).
32. S. L. Shyng, C. A. Cukras, J. Harwood, C. G. Nichols, *J Gen Physiol* 116, 599 (November, 2000).
33. H. Zhang, C. He, X. Yan, T. Mirshahi, D. E. Logothetis, *Nat Cell Biol* 1, 183 (July, 1999).
34. C. L. Huang, S. Feng, D. W. Hilgemann, *Nature* 391, 803 (Feb. 19, 1998).
35. Z. Fan, J. C. Makielski, *J Biol Chein* 272, 5388 (Feb. 28, 1997).
36. P. R. Stanfield, S. Nakajima, Y. Nakajima, *Rev. Physiol Biochem. Pharmacol.* 145, 47 (2002).
37. N, Takahashi et al., *J Biol Chem* 269, 23274 (Sep. 16, 1994).
38. G. X. Liu et al., *J Physiol* 532, 115 (Apr. 1, 2001).
39. Z. Lu, *Annu Rev Physiol* 66, 103 (2004).
40. C. G. Nichols, A. N. Lopatin, *Annu Rev Physiol* 59, 171 (1997).
41. P. Henry, W. L. Pearson, C. G. Nichols, *J Physiol* 495 (Pt 3), 681 (Sep. 15, 1996).
42. B. Fakler, U. Brandle, E. Glowatzki, H. P. Zenner, J. P. Ruppersberg, *Neuron* 13, 1413 (December, 1994).
43. H. C, Cho, R, G. Tsushima, T. T. Nguyen, H. R. Guy, P. H. Backx, *Biochemistry* 39, 4649 (Apr. 25, 2000).

44. M. L. Leyland, C. Dart, P. J. Spencer, M. J. Sutcliffe, P. R. Stanfield, *Pflugers Arch* 438, 778 (November, 1999).
45. K. M. Dibb et al., *J Biol Chem* 278, 49537 (Dec. 5, 2003).
46. J. Yang, M. Yu, Y. N. Jan, L. Y. Jan, *Proc Natl Acad Sci USA* 94, 1568 (Feb. 18, 1997).
47. Y. Zhou, J. H. Morais-Cabral, A. Kaufman, R. MacKinnon, *Nature* 414, 43 (Nov. 1, 2001).
48. S. B. Long, X. Tao, E. B. Campbell, R. MacKinnon, *Nature* 450, 376 (Nov. 15, 2007).
49. S. B. Long, E, B. Campbell, R. Mackinnon, *Science* 309, 897 (Aug. 5, 2005).
50. Y. Jiang et al., *Nature* 417, 523 (May 30, 2002).
51. S. Pegan, C. Arrabit, P. A. Slesinger, S. Choe, *Biochemistry* 45, 8599 (Jul. 18, 2006).
52. H. G. Shin, Z. Lu, *J Gen Physiol* 125, 413 (April, 2005).
53. H. G. Shin, Y. Xu, Z. Lu, *J Gen Physiol* 126, 123 (August, 2005).
54. D. Guo, Y. Ramu, A. M. Klem, Z. Lu, *J Gen Physiol* 121, 261 (April, 2003).
55. D. Guo, Z. Lu, *J Gen Physiol* 115, 799 (June, 2000).
56. M. Spassova, Z. Lu, *J Gen Physiol* 112, 211 (August, 1998).
57. W. L. Pearson, C. G. Nichols, *J Gen Physiol* 112, 351 (September, 1998).
58. Y. Thou, R. MacKinnon, *Biochemistry* 43, 4978 (May 4, 2004).
59. A. Cotton, G. Wilkinson, *Wiley interscience*.
60. D. Noble, R. W. Tsien, *J Physiol* 195, 185 (March, 1968).
61. C. A. Leech, P. R. Stanfield, *J Physiol* 319, 295 (1981).
62. S. Hagiwara, M. Yoshii, *J Physiol* 292, 251 (July, 1979).
63. A. L, Hodgkin, P. Horowicz, *J Physiol* 148, 127 (October, 1959).
64. D. Guo, Z. Lu, *J Physiol* 117, 395 (May, 2001).
65. D. Oliver, H. Hahn, C. Antz, J. P. Ruppersberg, B. Fakler, *Biophys J* 74, 2318 (May, 1998).
66. M. Spassova, Z. Lu, *J Gen Physiol* 114, 415 (September, 1999).
67. J. P. Felix et al., *Biochemistry* 45, 10129 (Aug. 22, 2006),
68. Y. Ram, A. M. Klem, Z. Lu, *Biochemistry* 43, 10701 (Aug. 24, 2004).
69. W. Jin, A. M. Klem, J. H. Lewis, Z. Lu, *Biochemistry* 38, 14294 (Oct. 26, 1999).
70. The X-ray crystallographic coordinates and structure factor files have been deposited in the Protein Data Bank with accession ID 3JYC.

MATERIALS AND METHODS

Cloning, Expression and Purification

A synthetic gene fragment (Bio Basic, Inc.) encoding residues 38 to 369 of chicken Kir2.2 channel (GI:118097849) was ligated into the XhoI/EcoRI cloning sites of a modified pPICZ-B vector (Invitrogen). The resulting protein has green fluorescent protein (GFP) and a 1D4 antibody recognition sequence (TETSQVAPA) on the C-terminus (I), separated by a PreScission protease cleavage site (SNSLEVLFO/GP).

The construct was linearized using PmeI and transformed into a HIS+ strain of SMD1163 of *Pichia pastoris* (Invitrogen) by electroporation (BioRad Micropulser). Transformants were selected on YPDS plates containing 400-1200 μg/ml Zeocin (Invitrogen). Resistant colonies were tested for expression by anti-1D4 tag Western Blot. For large-scale expression, small cultures grown from the best expressing colony were diluted into BMGY media (Invitrogen) and inoculated at 29° C. overnight, until $OD_{600}$ reached between 20-30. Cells were then pelleted, resuspended in BMM media (Invitrogen) and expressed overnight at 24° C. Cells were harvested, flash-frozen in liquid $N_2$, and stored at −80° C. until needed.

Cells were lysed in a Retsch, Inc. Model MM301 mixer mill (5×3.0 minutes at 25 cps). The lysis buffer contained 150 mM KCl, 50 mM TRIS-HCl pH 8.0, 0.1 mg/ml deoxyribonuclease 1, 0.1 μg/ml pepstatin, 1 μg/ml leupeptin, 1 μg/ml aprotinin, 0.1 mg/ml soy trypsin inhibitor, 1 mM benzamidine, 0.1 mg/ml AEBSF, with 1 mM phenylmethysulfonyl fluoride added just before lysis (3.0 ml lysis buffer/g cells). pH of the lysate was adjusted to 8.0 with KOH. The lysate was extracted with 100 mDM (n-decyl-β-D-maltopyranoside, Anatrace, soigrade) at room temperature for 1 hour with stirring, and then centrifuged for 40 minutes at 30,000 g, 10° C. Supernatant was added to 1D4-affinity resin pre-equilibrated with 150 mM KCl, 50 mM TRIS-HCl pH 8.0, and 4 mM DM. Suspension was layered with Argon and mixed by inversion for 2 hours at room temperature. Beads were collected on a column by gravity, washed with 2 column volumes of buffer (150 mM KCl, 50 mM TRIS-HCl pH 8.0, 1 mM EDTA pH 8.0, and 4 mM DM), and eluted with buffer plus 1 mg/ml 1D4 peptide (AnaSpec, Inc.) over 1 hour at room temperature. 20 mM DTT (Dithiothreitol) and 3 mM TECP were added to eluted protein. The protein was then digested with PreScission protease (20:1 w/w ratio) overnight at 4° C. Concentrated protein was further purified on a Superdex-200 gel filtration column in 150 mM KCl, 20 mM TRIS-HCl pH 8.0, 4 mM DM (anagrade), 3 mM TCEP, 20 mM DTT and 1 mM EDTA at 4° C.

The fraction corresponding to the tetramer peak was concentrated to about 8 mg/ml, mixed 1:1 with crystallization solution and set up as hanging drops over reservoirs containing 0.1 ml crystallization solution, Crystals appeared in 7-20% PEG400 or 2-10% PEG4000, with 500 mM KCl or NaCl, and 50 mM buffer pH 6.0-9.5 at 4° C. overnight and grew to full size within 2-3 days.

For studies with RbCl, the protein was purified in a similar fashion except that KCl was replaced with RbCl in all buffer solutions and crystals were grown in 10-20% PEG400, 500 mM RbCl, and 50 mM MES pH 6.5. For studies with 10 mM $EuCl_3$, crystals were grown in 7-20% PEG400, 1 M ammonium formate, 50 mM TRIS-HCl pH 8.5, and 10 mM $EuCl_3$. For studies with 10 mM $SrCl_2$, crystals were grown in 10-20% PEG400, 500 mM NaCl, 50 mM HEPES pH 7.5, and 10 mM $SrCl_2$. For studies with 200 mM $SrCl_2$, crystals were grown in 3-7% PEG4000, 200 mM $SrCl_2$, and 50 mM Na Citrate pH 5.6.

Structure Determination

Crystals were cryo-protected in reservoir plus 25% glycerol (v/v), 4 mM DM, 20 mM DTT, 3 mM TCEP, and 1 mM EDTA in a step-wise manner (5% glycerol increase each step) and flash-frozen in liquid nitrogen. Diffraction data from native crystals were collected to 3.1 Å at beamline 24ID-C (APS) and for crystals in various metal ions ($Rb^+$, $Sr^+$, and $Eu^{3+}$) at beamline X29 (Brookhaven NSLS). Images were processed with DENZO and intensities merged with SCALEPACK (2). Data were further processed using the CCP4 suite (3). The crystals belong to the I4 space group. The structure was solved by molecular replacement using the program MOLREP (4), with the 2.4 Å resolution structure of the cytoplasmic domain of mouse Kir2.1 (PDB 1U4F) as a search model. There is one copy of the subunit in the asymmetric unit. The model was built using O (5) and refined with CNS (50-3.1 Å) to $R_{free}$=27.2% (6). The final model contains residues 43-60 and 70-369 (residues 70 to 78 are modeled as alanines) of chicken Kir2.2, three additional residues SNS on the C-terminus corresponding to the PreScission cleavage site, and five K$^+$ ions. During the final minimization refinement step in CNS, occupancies of the K$^+$ ions were set to 0.5 (which gave rise to a lower R$_{free}$ compared to occupancy of 1.0) and B-factors of the K$^+$ ions were set to 85 (roughly the average B-factor of surrounding protein atoms). Crystallographic data and refinement statistics are shown in Table S1. Figures were made using PYMOL (www.pymol.org) (7).

Ion binding was assessed by calculating anomalous difference Fourier maps for data with Eu$^{3+}$ and F$_o$-F$_c$ maps for data with Rb$^+$ and Sr$^{2+}$ using fft in the CCP4 suite (3), Sr$^{2+}$ was analyzed at two different concentrations to discern whether the weak cavity peak was due to Sr$^{2+}$. This peak became stronger when Sr$^{2+}$ was increased from 10 mM to 200 mM while the monovalent cation concentration was decreased, consistent with Sr$^{2+}$ being present in the cavity but probably at low occupancy. Phases used to calculate F$_o$-F$_c$ omit maps were derived from a channel model devoid of ions in the cavity or cytoplasmic domain throughout refinement.

Electrophysiology

*Xenopus* oocytes were harvested from mature female *Xenopus laevis* and defolliculated by collagenase treatment for 1-2 hours. Oocytes were then rinsed thoroughly and stored in ND96 solution (96 mM NaCl, 2 mM KCl, 1.8 mM CaCl$_2$, 1.0 mM MgCl$_2$, 5 mM HEPES, 50 µg/ml gentamycin, pH 7.6 with NaOH). Defolliculated oocytes were selected 2-4 hours after collagenase treatment and injected with cRNA the next day. The injected oocytes were incubated in ND96 solution for 1-5 days before recording. All oocytes were stored in an incubator at 18° C.

The chicken Kir2.2 (residues 38 to 369) gene was subcloned into the pGEM vector (Promega). cRNA was prepared using T7 RNA polymerase (Promega) from NdeI-linearized plasmid DNA.

All recordings were performed at room temperature. For two-electrode voltage-clamp experiments, oocytes were held at 0 mV and pulsed from –80 mV to +80 mV with 10 mV increment steps. Recording solution contained 98 mM KCl, 0.3 mM CaCl$_2$, 1 mM MgCl$_2$, and 5 mM HEPES pH 7.6. The ionic currents were recorded with an oocyte clamp amplifier (OC-725C, Warner Instrument Corp.). The recorded signal was filtered at 1 kHz and sampled at 10 kHz using an analogue-to-digital converter (Digidata 1440A, Axon Instruments, Inc) interfaced with a computer. pClamp10.1 software (Axon Instruments, Inc) was used for controlling the amplifier and data acquisition. For patch-clamp experiments, each oocyte was incubated in a hypertonic solution containing 200 mM NaCl, 130 mM KCl, 5 mM K$_2$EDTA, 5 mM K$_2$HPO$_4$, 5 mM KH$_2$PO$_4$ pH 7.2 for 5-10 minutes and the vitelline membrane was removed before seal formation. Currents were recorded in either cell-attached or inside-out configuration with an Axopatch 200B amplifier, Digidata 1440A analogue-to-digital converter and pClamp10.1 software to control membrane voltage and record. During the current recordings, the membrane was first held at 0 mV followed by a 10-second voltage ramp from +80 mV to –80 mV, The pipette solution contained 140 mM KCl, 5 mM K$_2$HPO$_4$, 5 mM KH$_2$PO$_4$, 0.3 mM CaCl$_2$, 1 mM MgCl$_2$, pH 7.2 with KOH. The bath solution contained 130 mM KCl, 5 mM K$_2$EDTA, 5 mM K$_2$HPO$_4$, 5 mM KH$_2$PO$_4$, pH 7.2 with KOH.

For the single channel I-V curve shown in Figure S1D inset, each data point represents the current difference at a given voltage associated with the opening of a single channel.

REFERENCES

1. J. P. Wong, E. Reboul, R. S. Molday, J. Kast, *J Proteome Res* 8, 2388 (May, 2009).
2. Z. Otwinowski, W. Minor, *Methods Enzymol.* 276, 307 (1997).
3. N. Collaborative Computational Project, *Acta Cryst.* D50, 760 (1994).
4. A. Vagin, A. Teplyakov, *Acta Crystallogr. D. Biol. Crystallogr.* 56 Pt 12:1622-4, 1622 (2000).
5. T. A. Jones, J. Y. Zou, S. W. Cowan, M. Kjeldgaard, *Acta Cryst.* A47, 110 (1991).
6. A. T. Brunger et al., *Acta Cryst.* D54, 905 (1998).
7. W. L. DeLano, *DeLano Scientific*, Palo Alto, Calif., USA. http://www.pymol.org. (2002).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all values are approximate, and are provided for description.

All patents, applications, publications, test methods, literature, and other materials cited herein are hereby incorporated by reference.

TABLE S1

| Crystallographic data and refinement statistics | | | | | |
|---|---|---|---|---|---|
| Data Collection | | | | | |
| Data set | Native | Rb$^+$ (650 mM) | Sr$^{2+}$ (10 mM) | Sr$^{2+}$ (200 mM) | Eu$^{3+}$ (10 mM) |
| Space group | I4 | I4 | I4 | I4 | I4 |
| Lattice constants (Å) | a = b = 84.018, c = 196.121 $\alpha = \beta = \gamma = 90°$ | a = b = 82.714, c = 196.142 $\alpha = \beta = \gamma = 90°$. | a = b = 82.806, c = 195.605 $\alpha = \beta = \gamma = 90°$ | a = b = 83.268, c = 197.143 $\alpha = \beta = \gamma = 90°$ | a = b = 84.221, c = 195.915 $\alpha = \beta = \gamma = 90°$ |
| Source | APS 24ID-C | BNL X29 | BNL X29 | BNL X29 | BNL X29 |
| Wavelength (Å) | 0.97949 | 1.0809 | 1.0809 | 1.0809 | 1.5222 |
| Resolution (Å) | 50-3.1 | 50-4.0 | 50-3.3 | 50-3.8 | 50-6.0 |
| Total/unique observations | 65,452/12,153 | 25,333/5,231 | 60,844/9,910 | 31,462/6,571 | 5,649/1,517 |
| I sigma (I) [a] | 33.1 (2.3) | 20.0 (1.8) | 24.3 (2.4) | 20.8 (2.7) | 24.7 (1.6) |
| Redundancy [a] | 5.4 (4.6) | 4.8 (4.3) | 6.1 (5.9) | 4.8 (4.7) | 3.7 (1.4) |
| Completeness (%) [a] | 99.7 (99.9) | 93.3 (83.8) | 99.8 (100.0) | 99.7 (100.0) | 87.9 (49.4) |
| R$_{sym}$ (%) [a,b] | 6.8 (73.6) | 10.1 (78.3) | 11.5 (89.4) | 9.6 (69.3) | 7.0 (35.7) |
| Model refinement | | | | | |
| Resolution (Å) | 50-3.1 | 50-4.0 | 50-3.3 | 50-3.8 | 50-6.0 |
| Number of reflections | 12,122 (609) | 5,221 (272) | 9,895 (504) | 6,569 (346) | 1,517 (76) |

TABLE S1-continued

Crystallographic data and refinement statistics

| $R_{work}/R_{free}$ | 24.4/27.2 | 29.6/35.0 | 24.9/28.6 | 25.8/30.4 | 36.5/39.9 |
|---|---|---|---|---|---|
| R.m.s. deviation of bond length (Å) | 0.010 | | | | |
| R.m.s. deviation of bond angles (°) | 1.59 | | | | |
| Protein atoms / K$^+$ ions | 2,530/5 | | | | |
| Mean B value | 112.1 | | | | |
| Ramachandran plot [c] | 76.0/21.9/2.1 | | | | |

R.m.s., root mean-squared.

[a] Number in the parentheses represents statistics for data in the highest resolution shell.

[b] $R_{sym} = \Sigma |I_i - \langle I_i \rangle| / \Sigma |I_i|$, where $\langle I_i \rangle$ is the average intensity of symmetry equivalent reflections.

[c] The three numbers represent the percentage of residues in most favored/additionally allowed/generously allowed regions.

SEQUENCES:

1. human Kir 1.1 - variable portion of turret region
PEFHPSANHTP 2. human Kir 1.2 - variable portion of turret region
LELDPPANHTP 3. human Kir 2.1 - variable portion of turret region
DASKEGKA 4. human Kir 2.2 - variable portion of turret region
EPAEGRGRTP 5. human Kir 2.3 - variable portion of turret region
EASPGVPAAGGPAAGGGGAAPVAPKP 6. human Kir 2.4 - variable portion of turret region
AAPPPPAP 7. human Kir 3.1 - variable portion of turret region
NKAHVGNYTP 8. human Kir 3.4 - variable portion of turret region
DHVGDQEWIP 9. human Kir 6.1 - variable portion of turret region
YAYMEKSGMEKSGLESTV 10. human Kir 6.2 - variable portion of turret region
APSEGTAEP 11. human Kir 7.1 - variable portion of turret region
ELDHDAPPENHTI 12. chicken Kir 2.1 - variable portion of turret region
ENQENNKP 13. chicken Kir 2.2 - variable portion of turret region
ENPGGDDTFKP 14. human Kir 1.1 - amino acid sequence
```
  1 MNASSRNVFD TLIRVLTESM FKHLRKWVVT REFGHSRQRA RLVSKDGRCN IEFGNVEAQS
 61 RFIFFVDIWT TVLDLKWRYK MTIFITAFLG SWFFFGLLWY AVAYIHKDLP EFHPSANHTP
121 CVENINGLTS AFLFSLETQV TIGYGFRCVT EQCATAIFLL IFQSILGVII NSFMCGAILA
181 KISRPKKRAK TITFSKNAVI SKRGGKLCLL IRVANLRKSL LIGSHIYGKL LKTTVTPEGE
241 TIILDQININ FVVDAGNENL FFISPLTIYH VIDHNSPFFH MAAETLLQQD FELVVFLDGT
301 VESTSATCQV RTSYVPEEVL WGYRFAPIVS KTKEGKYRVD FHNFSKTVEV ETPHCAMCLY
361 NEKDVRARMK RGYDNPNFIL SEVNETDDTK M
```

15. human Kir 1.2 - amino acid sequence
```
  1 MTSVAKVYYS QTTQTESRPL MGPGIRRRRV LTKDGRSNVR MEHIADKRFL YLKDLWTTFI
 61 DMQWRYKLLL FSATFAGTWF LFGVVWYLVA VAHGDLLELD PPANHTPCVV QVHTLTGAFL
```

```
SEQUENCES:

121 FSLESQTTIG YGFRYISEEC PLAIVLLIAQ LVLTTILEIF ITGTFLAKIA RPKKRAETIR

181 FSQHAVVASH NGKPCLMIRV ANMRKSLLIG CQVTGKLLQT HQTKEGENIR LNQVNVTFQV

241 DTASDSPFLI LPLTFYHVVD ETSPLKDLPL RSGEGDFELV LILSGTVEST SATCQVRTSY

301 LPEEILWGYE FTPAISLSAS GKYIADFSLF DQVVKVASPS GLRDSTVRYG DPEKLKLEES

361 LREQAEKEGS ALSVRISNV 16. human Kir 2.1 - amino acid sequence
    1 MGSVRTNRYS IVSSEEDGMK LATMAVANGF GNGKSVHTR QQCRSRFVKK DGHCNVQFIN

61 VGEKGQRYLA DIFTTCVDIR WRWMLVIFCL AFVLSWLFFG CVFWLIALLH GDLDASKEGK

121 ACVSEVNSFT AAFLFSIETQ TTIGYGFRCV TDECPIAVFM VVFQSIVGCI IDAFIIGAVM

181 AKMAKPKKRN ETLVFSHNAV IAMRDGKLCL MWRVGNLRKS HLVEAHVRAQ LLKSRITSEG

241 EYIPLDQIDI NVGFDSGIDR IFLVSPITIV HEIDEDSPLY DLSKQDIDNA DFEIVVILEG

301 MVEATAMTTQ CRSSYLANEI LWGHRYEPVL FEEKHYYKVD YSRFHKTYEV PNTPLCSARD

361 LAEKKYILSN ANSFCYENEV ALTSKEEDDS ENGVPESTST DTPPDIDLHN QASVPLEPRP

421 LRRESEI 17. human Kir 2.2 - amino acid sequence
    1 MTAASRANPY SIVSSEEDGL HLVTMSGANG FGNGKVHTRR RCRNRFVKKN GQCNIEFANM

61 DEKSQRYLAD MFTTCVDIRW RYMLLIFSLA FLASWLLFGI IFWVIAVAHG DLEPAEGRGR

121 TPCVMQVHGF MAAFLPSIET QTTIGYGLRC VTEECPVAVF MVVAQSIVGC IIDSFMIGAI

181 MAKMARPKKR AQTLLFSHNA VVALRDGKLC LMWRVGNLRK SHIVEAHVRA QLIKPRVTEE

241 GEYIPLDQID IDVGFDKGLD RIFLVSPITI LHEIDEASPL FGISRQDLET DDFEIVVILE

301 GMVEATAMTT QARSSYLANE ILWGHRFEPV LFEEKNQYKI DYSHFHKTYE VPSTPRCSAK

361 DLVENKFLLP SANSFCYENE LAFLSRDEED EADGDQDGRS RDGLSPQARH DFDRLQAGGG

421 VLEQRPYRRE SEI 18. human Kir 2.3 - amino acid sequence
    1 MHGHSRNGQA HVPRRKRRNR FVKKNGQCNV YFANLSNKSQ RYMADIFTTC VDTRWRYMLM

61 IFSAAFLVSW LFFGLLFWCI AFFHGDLEAS PGVPAAGGPA AGGGGAAPVA PKPCIMHVNG

121 FLGAFLFSVE TQTTIGYGFR CVTEECPLAV IAVVVQSIVG CVIDSFMIGT IMAKMARPKK

181 RAQTLLFSHH AVISVRDGKL CLMWRVGNLR KSHIVEAHVR AQLIKPYMTQ EGEYLPLDQR

241 DLNVGYDIGL DRIFLVSPII IVHEIDEDSP LYGMGKEELE SEDFEIVVIL EGMVEATAMT

301 TQARSSYLAS EILWGHRFEP VVFEEKSHYK VDYSRFHKTY EVAGTPCCSA RELQESKITV

361 LPAPPPPPSA FCYENELALM SQEEEEMEEE AAAAAVAAG LGLEAGSKEE AGIIRMLEFG

421 SHLDLERMQA SLPLDNISYR RESAI 19. human Kir 2.4 - sequence
    1 MGLARALRRL SGALDSGDSR AGDEEEAGPG LCRNGWAPAP VQSPVGRRRG RFVKKDGHCN

61 VRFVNLGGQG ARYLSDLFTT CVDVRWRWMC LLFSCSFLAS WLLFGLAFWL IASLHGDLAA

121 PPPPAPCFSH VASFLAAFLF ALETQTSIGY GVRSVTEECP AAVAAVVLQC IAGCVLDAFV

181 VGAVMAKMAK PKKRNETLVF SENAVVALRD HRLCLMWRVG NLRRSHLVEA HVRAQLLQPR

241 VTPEGEYIPL DHQDVDVGFD GGTDRIFLVS PITIVHEIDS ASPLYELGRA ELARADFELV

301 VILEGMVEAT AMTTQCRSSY LPGELLWGHR FEPVLFQRGS QYEVDYRHFH RTYEVPGTPV

361 CSAKELDERA EQASHSLKSS FPGSLTAFCY ENELALSCCQ EEDEDDETEE GNGVETEDGA

421 ASPRVLTPTL ALTLPP
```

SEQUENCES:

20. human Kir 3.1 - amino acid sequence
    1 MSALRRKFGD DYQVVTTSSS GSGLQPQGPG QDPQQQLVPK KKRQRFVDKN GRCNVQHGNL
   61 GSETSRYLSD LFTTLVDLKW RWNLFIFILT YTVAWLFMAS MWWVIAYTRG DLNKAHVGNY
  121 TPCVANVYNF PSAFLEFIET EATIGYGYRY ITDKCPEGII LFLFQSILGS IVDAFLIGCM
  181 FIKMSQPKKR AETLMFSEHA VISMRDGKLT LMFRVGNLRN SHMVSAQIRC KLLKSRQTPE
  241 GEFLPLDQLE LDVGFSTGAD QLFLVSPLTI CHVIDAKSPF YDLSQRSMQT EQFEIVVILE
  301 GIVETTGMTC QARTSYTEDE VLWGHRFFPV ISLEEGFFKV DYSQFHATFE VPTPPYSVKE
  361 QEEMLLMSSP LIAPAITNSK ERHNSVECLD GLDDITTKLP SKLQKITGRE DFPKKLLRMS
  421 STTSEKAYSL GDLPMKLQRI SSVPGNSEEK LVSKTTKMLS DPMSQSVADL PPKLQKMAGG
  481 AARMEGNLPA KLRKMNSDRF T 21. human Kir 3.4 - amino acid sequence
    1 MAGDSRNAMN QDMEIGVTPW DPKKIPKQAR DYVPIATDRT RLLAEGKKPR QRYNEKSGKC
   61 NVHHGNVQET YRYLSDLFTT LVDLKWRFNL LVFTMVYTVT WLFFGFIWWL IAYIRGDLDH
  121 VGDQEWIPCV ENLSGFVSAF LFSIETETTI GYGFRVITEK CPEGIILLLV QAILGSIVNA
  181 FMVGCMFVKI SQPKKRAETL MESNNAVISM RDEKLCLMFR VGDLRNSHIV EASIRAKLIK
  241 SRQTKEGEFI PLNQTDINVG FDTGDDRLFL VSPLIISHEI NQKSPFWEMS QAQLHQEEFE
  301 VVVILEGMVE ATGMTCQARS SYMDTEVLWG HRFTPVLTLE KGFYEVDYNT FHDTYETNTP
  361 SCCAKELAEM KREGRLLQYL PSPPLLGGCA EAGLDAEAEQ NEEDEPKGLG GSREARGSV 22. human Kir 4.1 - amino acid sequence
    1 MTSVARVYYS QTTQTESRPL MGPGIRRRRV LTKDGRSNVR MEHIADKRFL YLKDLWTTFI
   61 DMQWRYKLLL FSATFAGTWF LFGVVWYLVA VAHGDLLELD PPANHTPCVV QVHTLTGAFL
  121 FSLESQTTIG YGFRYISEEC PLAIVLLIAQ LVLTTILEIF ITGTFLAKIA RPKKRAETIR
  181 FSQHAVVASH NGKPCLMIRV ANMRKSLLIG CQVTGKLLQT HQTKEGENIR LNQVNVTFQV
  241 DTASDSPFLI LPLTFYHVVD ETSPLKDLPL RSGEGDFELV LILSGTVEST SATCQVRTSY
  301 LPEEILWGYE FTPAISLSAS GKYIADFSLF DQVVKVASPS GLRDSTVRYG DPEKLKLEES
  361 LREQAEKEGS ALSVRISNV 23. human Kir 4.2 - amino acid sequence
    1 MDAIHIGMSS TPLVKHTAGA GLKANRPRVM SKSGHSNVRI DKVDGIYLLY LQDLWTTVID
   61 NKWRYKLTLF AATFVMTWFL FGVIYYAIAF IHGDLEPGEP ISNHTPCIMK VDSLTGAFLF
  121 SLESQTTIGY GVRSITEECP HAIFILVAQL VITTLIEIFI TGTFLAKIAR PKKRAETIKF
  181 SHCAVITKQN GKLCLVIQVA NMRKSLLIQC QLSGKLLQTH VTKEGERILL NQATVKFHVD
  241 SSSESPFLIL PMTFYHVLDE TSPLRDLTPQ NLKEKEFELV VLLNATVEST SAVCQSRTSY
  301 IPEEIYWGFE FVPVVSLSKN GKYVADFSQF EQIRKSPDCT FYCADSEKQQ LEEKYRQEDQ
  361 RERELRTLLL QQSNV 24. human Kir 5.1 - amino acid sequence
    1 MSYYGSSYHI INADAKYPGY PPEHIIAEKR RARRRLLHKD GSCNVYFKHI FGEWGSYVVD
   61 IFTTLVDTKW RHMFVIFSLS YILSWLIFGS VFWLIAFHHG DLLNDPDITP CVDNVHSFTG
  121 AFLFSLETQT TIGYGYRCVT EECSVAVLMV ILQSILSCII NTFIIGAALA KMATARKRAQ
  181 TIRFSYFALI GMRDGKLCLM WRIGDFRPNH VVEGTVRAQL LRYTEDSEGR MTMAFKDLKL
  241 VNDQIILVTP VTIVHEIDHE SPLYALDRKA VAKDNFEILV TFIYTGDSTG TSHQSRSSYV

```
    301 PREILWGHRF NDVLEVKRKY YKVNCLQFEG SVEVYAPFCS AKQLDWKDQQ LHIEKAPPVR

361 ESCTSDTKAR RRSFSAVAIV SSCENPEETT TSATHEYRET PYQKALLTLN RISVESQM 25. human Kir 6.1 - amino acid sequence
      1 MLARKSIIPE EYVLARIAAE NLRKPRIRDR LPKARFIAKS GACNLAHKNI REQGRFLQDI

61 FTTLVDLKWR HTLVIFTMSF LCSWLLFAIM WWLVAFAHGD IYAYMEKSGM EKSGLESTVC

121 VTNVRSFTSA FLFSIEVQVT IGFGGRMMTE ECPLAITVLI LQNIVGLIIN AVMLGCIFMK

181 TAQAHRRAET LIFSRHAVIA VRNGKLCFMF RVGDLRKSMI ISASVRIQVV KKTTTPEGEV

241 VPIHQLDIPV DNPIESNNIF LVAPLIICHV IDKRSPLYDI SATDLANQDL EVIVILEGVV

301 ETTGITTQAR TSYIAEEIQW GHRFVSIVTE EEGVYSVDYS KFGNTVKVAA PRCSARELDE

361 KPSILIQTLQ KSELSHQNSL RKRNSMRRNN SMRRNNSIRR NNSSLMVPKV QFMTPEGNQN

421 TSES 26. human Kir 6.2 - amino acid sequence
      1 MLSRKGIIPE EYVLTRLAED PAKPRYRARQ RRARFVSKKG NCNVAHKNIR EQGRFLQDVF

61 TTLVDLKWPH TLLIFTMSFL CSWLLFAMAW WLIAFAHGDL APSEGTAEPC VTSIHSFSSA

121 FLFSIEVQVT IGFGGRMVTE ECPLAILILI VQNIVGLMIN AIMLGCIFMK TAQAHRRAET

181 LIFSKHAVIA LRHGRLCFML RVGDLRKSMI ISATIHMQVV RKTTSPEGEV VPLHQVDIPM

241 ENGVGGNSIF LVAPLIIYHV IDANSPLYDL APSDLHHHQD LEIIVILEGV VETTGITTQA

301 RTSYLADEIL WGQRFVPIVA EEDGRYSVDY SKFGNTVKVP TPLCTARQLD EDHSLLEALT

361 LASARGPLRK RSVPMAKAKP KFSISPDSLS 27. human Kir 7.1 - amino acid sequence
      1 mdssnckvia pllsqryrrm vtkdghstlq mdgaqrglay lrdawgilmd mrwrwmmlvf 61 sasfvvhwlv favlwyvlae mngdleldhd appenhticv kyitsftaaf sfsletqlti 121 gygtmfpsgd cpsaiallai qmllglmlea fitgafvaki arpknrafsi rftdtavvah 181 mdgkpnlifq vantrpsplt svrvsavlyq erengklyqt svdfhldgis sdecpffifp 241 ltyyhsitps splatllqhe npshfelvvf lsamqegtge icqrrtsylp seimlhhcfa 301 slltrgskge ygikmenfdk typefptplv skspnrtdld ihingqsidn fqisetglte 28. chicken Kir 2.1 - amino acid sequence
      1 MGSVRTNRYS IVSSEEDGMK LATMAVANGF GNGKSKVHTR QQCRSRFVKK DGHCNVQFIN

61 VGEKGQRYLA DIFTTCVDIR WRWMLVIFCL TFILSWLFFG CVFWLIALLH GDLENQENNK

121 PCVSQVSSFT AAFLFSIETQ TTIGYGFRCV TDECPIAVFM VVFQSIVGCI IDAFIIGAVM

181 AKMAKPKKRN ETLVFSHNAV VAMRDGKLCL MWRVGNLRKS HLVEAHVRAQ LLKSRITSEG

241 EYIPLDEIDI NVGFDSGIDR IFLVSPITIV HEIDEDSPLY DLSKQDMDNA DFEIVVILEG

301 MVEATAMTTQ CRSSYLANEI LWGHRYEPVL FEEKNYYKVD YSRFHKTYEV PNTPICSARD

361 LAEKKYILSN ANSFCYENEV ALTSKEEDEI DTGVPESTST DTHPDMDHHN QAGVPLEPRP

421 LRRESEI 29. chicken Kir 2.2 - amino acid sequence
      1 mtagrvnpys ivsseedglr lttmpgingf gngkihtrrk crnrfvkkng qcnveftnmd 61 dkpqryiadm fttcvdirwr ymlllfslaf lvswllfgli fwlialihgd lenpggddtf 121 kpcvlqvngf vaaflfsiet qttigygfrc vteecplavf mvvvqsivgc iidsfmigai 181 makmarpkkr aqtllfshna vvamrdgklc lmwrvgnlrk shiveahvra qlikpritee 241 geyipldqid idvgfdkgld riflvspiti lheinedspl fgisrqdlet ddfeivvile
```

SEQUENCES:

301 gmveatamtt qarssylase ilwghrfepv lfeeknqykv dyshfhktye vpstprcsak 361 dlvenkfllp stnsfcyene lafmsrdede edddsrgldd lspdnrhefd rlqatialdq 421 rsyrresei 30. human Kir 1.1 - cDNA
  1 atgaatgctt ccagtcggaa tgtgtttgac acgttgatca gggtgttgac agaaagtatg 61 ttcaaacatc ttcggaaatg ggtcgtcact cgcttttttg ggcattctcg caaagagca 121 aggctagtct ccaaagatgg aaggtgcaac atagaatttg caatgtgga ggcacagtca 181 aggtttatat tctttgtgga catctggaca acggtacttg acctcaagtg gagatacaaa 241 atgaccattt tcatcacagc cttcttgggg agttggtttt tctttggtct cctgtggtat 301 gcagtagcgt acattcacaa agacctcccg gaattccatc cttctgccaa tcacactccc 361 tgtgtggaga atattaatgg cttgacctca gcttttctgt tttctctgga gactcaagtg 421 accattggat atggattcag gtgtgtgaca gaacagtgtg ccactgccat ttttctgctt 481 atctttcagt ctatacttgg agttataatc aattctttca tgtgtggggc catcttagcc 541 aagatctcca ggcccaaaaa acgtgccaag accattacgt tcagcaagaa cgcagtgatc 601 agcaaacggg agggaagct tgcctccta atccgagtgg ctaatctcag aagagcctt 661 cttattggca gtcacattta tggaaagctt ctgaagacca cagtcactcc tgaaggagag 721 accattattt tggaccagat caatatcaac tttgtagttg acgctgggaa tgaaaattta 781 ttcttcatct ccccattgac aatttaccat gtcattgatc acaacagccc tttcttccac 841 atggcagcgg agacccttct ccagcaggac tttgaattag tggtgttttt agatggcaca 901 gtggagtcca ccagtgctac ctgccaagtc cggacatcct atgtcccaga ggaggtgctt 961 tggggctacc gttttgctcc catagtatcc aagacaaagg aagggaaata ccgagtggat 1021 ttccataact ttagcaagac agtggaagtg gagacccctc actgtgccat gtgcctttat 1081 aatgagaaag atgttagagc caggatgaag agaggctatg acaaccccaa cttcatcttg 1141 tcagaagtca atgaaacaga tgacaccaaa atgtaa 31. human Kir 1.2 - cDNA
  1 cttttctgat cccagctccg ggtttaagag tcctggcacg gcccgtcgca cagctctgct 61 cctaactcct gcccgccccg tccgtccatc tgtcccgctg ccccgcggcc catccaaggg 121 gccactccac ctcggaccca agatgacgtc agttgccaag gtgtattaca gtcagaccac 181 tcagacagaa agccggcccc taatgggccc agggatacga cggcggagag tcctgacaaa 241 agatggtcgc agcaacgtga aatggagca cattgccgac aagcgcttcc tctacctcaa 301 ggacctgtgg acaaccttca ttgacatgca gtggcgctac aagcttctgc tcttctctgc 361 gacctttgca ggcacatggt tcctctttgt cgtggtgtgg tatctggtag ctgtggcaca 421 tgggacctg ctggagctgg acccccggc caaccacacc ccctgtgtgg tacaggtgca 481 cacactcact ggagccttcc tcttctccct tgaatcccaa accaccattg ctatggcttt 541 ccgctacatc agtgaggaat gtccactagc cattgtgctt cttattgccc agctggtgct 601 caccaccatc ctggaaatct tcatcacagg taccttcctg cgaagattg cccggcccaa 661 gaagcgggct gagaccattc gtttcagcca gcatgcagtt gtggcctccc acaatggcaa 721 gccctgcctc atgatccgag ttgccaatat gcgcaaaagc ctcctcattg gctgccaggt 781 gacaggaaaa ctgcttcaga cccaccaaac caaggaaggg gagaacatcc ggctcaacca 841 ggtcaatgtg acttttccaag tagacacagc ctctgacagc cccttcctta ttctacccct

| SEQUENCES: |
|---|

```
 901 taccttctat catgtggtag atgagaccag tcccttgaaa gatctccctc ttcgcagtgg
 961 tgagggtgac tttgagctgg tgctgatcct aagtgggaca gtggagtcca ccagtgccac
1021 ctgtcaggtg cgcacttcct acctgccaga ggagatcctt tggggctacg agttcacacc
1081 tgccatctca ctgtcagcca gtggtaaata catagctgac tttagccttt ttgaccaagt
1141 tgtgaaagtg gcctctccta gtggcctccg tgacagcact gtacgctacg agaccctga
1201 aaagctcaag ttggaggagt cattaaggga gcaagctgag aaggagggca gtgcccttag
1261 tgtgcgcatc agcaatgtct ga
```

32. human Kir 2.1 - cDNA
```
   1 atgggcagtg tgcgaaccaa ccgctacagc atcgtctctt cagaagaaga cggtatgaag
  61 ttggccacca tggcagttgc aaatggcttt gggaacggga gagtaaagt ccacacccga
 121 caacagtgca ggagccgctt tgtgaagaaa gatggccact gtaatgttca gttcatcaat
 181 gtgggtgaga aggggcaacg gtacctcgca gacatcttca ccacgtgtgt ggacattcgc
 241 tggcggtgga tgctggttat cttctgcctg gcttttcgtc tgtcatggct gttttttggc
 301 tgtgtgtttt ggttgatagc tctgctccat ggggacctgg atgcatccaa agagggcaaa
 361 gcttgtgtgt ccgaggtcaa cagcttcacg gctgccttcc tcttctccat tgagacccag
 421 acaaccatag gctatggttt cagatgtgtc acggatgaat gcccaattgc tgttttcatg
 481 gtggtgttcc agtcaatcgt gggctgcatc atcgatgctt tcatcattgg cgcagtcatg
 541 gccaagatgg caaagccaaa gaagagaaac gagactcttg tcttcagtca atgccgtg
 601 attgccatga gagacggcaa gctgtgtttg atgtggcgag tgggcaatct tcggaaaagc
 661 cacttggtgg aagctcatgt tcgagcacag ctcctcaaat ccagaattac ttctgaaggg
 721 gagtatatcc ctctggatca aatagacatc aatgttgggt ttgacagtgg aatcgatcgt
 781 atatttctgt gtccccaat cactatagtc catgaaatag atgaagacag tcctttatat
 841 gatttgagta acaggacat tgacaacgca gactttgaaa tcgtggtcat actggaaggc
 901 atggtggaag ccactgccat gacgacacag tgccgtagct cttatctagc aaatgaaatc
 961 ctgtggggcc accgctatga gcctgtgctc tttgaagaga agcactacta caaagtggac
1021 tattccaggt tccacaaaac ttacgaagtc cccaacactc cctttgtag tgccagagac
1081 ttagcagaaa agaaatatat cctctcaaat gcaaattcat tttgctatga aaatgaagtt
1141 gccctcacaa gcaaagagga agacgacagt gaaaatggag ttccagaaag cactagtacg
1201 gacacgcccc ctgacataga ccttcacaac caggcaagtg tacctctaga gcccaggccc
1261 ttacggcgag agtcggagat atga
```

33. human Kir 2.2 - cDNA
```
   1 atgaccgcgg ccagccgggc caaccctac agcatcgtgt catcggagga ggacgggctg
  61 cacctggtca ccatgtcggg cgccaacggc ttcggcaacg gcaaggtgca cacgcgccgc
 121 aggtgccgca accgcttcgt caagaagaat ggccagtgca cattgagtt cgccaacatg
 181 gacgagaagt cacagcgcta cctggctgac atgttcacca cctgtgtgga catccgctgg
 241 cggtacatgc tgctcatctt ctcgctggcc ttccttgcct cctggctgct gttcggcatc
 301 atcttctggg tcatcgcggt ggcacacggt gacctggagc cggctgaggg ccggggccgc
 361 acaccctgtg tgatgcaggt gcacggcttc atggcggcct tcctcttctc catcgagacg
 421 cagaccacca tcggctacgg gctgcgctgt gtgacggagg agtgcccggt ggccgtcttc
```

| SEQUENCES: |
| --- |
| 481 atggtggtgg cccagtccat cgtgggctgc atcatcgact ccttcatgat tggtgccatc |
| 541 atggccaaga tggcaaggcc caagaagcgg gcacagacgc tgctgttgag ccacaacgcc |
| 601 gtggtggccc tgcgtgacgg caagctctgc ctcatgtggc gtgtgggtaa cctgcgcaag |
| 661 agccacattg tggaggccca tgtgcgcgcg cagctcatca agccgcgggt caccgaggag |
| 721 ggcgagtaca tcccgctgga ccagatcgac atcgatgtgg gcttcgacaa gggcctggac |
| 781 cgcatctttc tggtgtcgcc catcaccatc ttgcatgaga ttgacgaggc caggccgctc |
| 841 ttcggcatca gccggcagga cctggagacg gacgactttg agatcgtggt catcctggaa |
| 901 ggcatggtgg aggccacagc catgaccacc caggcccgca gctcctacct ggccaatgag |
| 961 atcttctggg gtcaccgctt tgagcccgtg ctcttcgagg agaagaacca gtacaagatt |
| 1021 gactactcgc acttccacaa gacctatgag gtgccctcta cgccccgctg cagtgcgaag |
| 1081 gatctggtag agaacaagtt cctgctgccc agcgccaact ccttctgcta cgagaacgag |
| 1141 ctggccttcc tgagccgtga cgaggaggat gaggcggacg agaccagga cggccgaagc |
| 1201 cgggacggcc tcagcccca ggccaggcat gactttgaca gactccaggc tggcggcggg |
| 1261 gacctggagc agcggcccta cagacgggag tcagagatct ga |

34. human Kir 2.3 - cDNA

| | |
| --- | --- |
| 1 atgcacggac acagccgcaa cggccaggcc cacgtgcccc ggcggaagcg ccgcaaccgc |
| 61 ttcgtcaaga agaacggcca atgcaacgtg tacttcgcca acctgagcaa caagtcgcag |
| 121 cgctacatgg cggacatctt caccacctgc gtggacacgc gctggcgcta catgctcatg |
| 181 atcttctccg cggccttcct tgtctcctgg ctcttttttcg gcctcctctt ctggtgtatc |
| 241 gccttcttcc acggtgacct ggaggccagc ccaggggtgc ctgcggcggg gggcccggcg |
| 301 gcgggtggtg gcggaggagc cccggtggcc cccaagccct gcatcatgca cgtgaacggc |
| 361 ttcctgggtg ccttcctgtt ctcggtggag acgcagacga ccatcggcta tgggttccgg |
| 421 tgcgtgacag aggagtgccc gctggcagtc atcgctgtgg tggtccagtc catcgtgggc |
| 481 tgcgtcatcg actccttcat gattggcacc atcatggcca agatggcgcg gcccaagaag |
| 541 cgggcgcaga cgttgctgtt cagccaccac gcggtcattt cggtgcgcga cggcaagctc |
| 601 tgcctcatgt ggcgcgtggg caacctgcgc aagagccaca ttgtggaggc ccacgtgcgg |
| 661 gcccagctca tcaagccata catgacccag gagggcgagt acctgccct ggaccagcgg |
| 721 gacctcaacg tgggctatga catcggcctg gaccgcatct tcctggtgtc gcccatcatc |
| 781 attgtccacg agatcgacga ggacagcccg ctttatggca tgggcaagga ggagctggag |
| 841 tcggaggact ttgagatcgt ggtcatcctg gagggcatgg tggaggccac ggccatgacc |
| 901 acccaggccc gcagctccta cctggccagc gagatcctgt ggggccaccg ctttgagcct |
| 961 gtggtcttcg aggagaagag ccactacaag gtggactact cacgttttca caagacctac |
| 1021 gaggtggccg gcacgcctg ctgctcggcc cgggagctgc aggagagtaa gatcaccgtg |
| 1081 ctgcccgccc caccgccccc tcccagtgcc ttctgctacg agaacgagct ggcccttatg |
| 1141 agccaggagg aagaggagat ggaggaggag gcagctgcgg cggccgcggt ggccgcaggc |
| 1201 ctgggcctgg aggcgggttc aaggaggag gcgggcatca tccggatgct ggagttcggc |
| 1261 agccacctgg acctggagcg catgcaggct tccctcccgc tggacaacat ctcctaccgc |
| 1321 agggagtctg ccatctga |

-continued

SEQUENCES:

35. human Kir 2.4 - cDNA
```
   1 atgggcctgg ccagggccct acgccgcctc agcggcgccc tggattcggg agacagccgg
  61 gcgggcgatg aagaggaggc cgggcccggg ttgtgccgca acgggtgggc gccggcaccg
 121 gtgcagtcac ccgtgggccg gcgccgcggt cgcttcgtca agaaagacgg gcactgcaac
 181 gtgcgtttcg taaacctggg tggccagggc gcgcgctacc tgagcgacct gttcaccaca
 241 tgcgtggacg tgcgctggcg ctggatgtgc ctgctcttct cctgctcctt cctcgcctcc
 301 tggctgctct tcggcctggc cttctggctc attgcctcgc tgcacggcga cctggccgcc
 361 ccgccaccgc ccgcgccctg cttctcacac gtggccagct tcctggccgc cttcctcttc
 421 gcgctggaga cgcagacgtc catcggctac ggcgtgcgca gcgtcaccga ggagtgcccg
 481 gccgctgtgg ccgccgtggt gctgcagtgc attgccggct gcgtgctcga cgccttcgtc
 541 gtgggtgctg tcatggccaa gatggccaaa cccaagaagc gcaacgagac gctggtcttc
 601 agcgagaacg ccgtcgtggc gctgcgcgac accgcctct gcctcatgtg gcgcgtcggc
 661 aacctgcgcc gcagccacct ggtcgagacc cacgtgcgtg cccagctgct gcagccccgt
 721 gtgaccccag agggtgagta catcccgctg accaccagg atgtggatgt gggctttgat
 781 ggaggcaccg atcgtatctt cctcgtgtcc cccatcacca tcgtccatga gatcgactct
 841 gccagtcctc tgtatgagct aggacgtgcc gagctggcc gggctgactt tgagctggtg
 901 gtcattctcg aggggatggt tgaggccaca gccatgacca cacagtgtcg ctcgtcctac
 961 ctccctggtg aactgctctg ggccatcgt tttgagccag ttctcttcca gcgtggctcc
1021 cagtatgagg tcgactatcg ccacttccat cgcacttatg aggtcccagg acaccggtc
1081 tgcagtgcta aggagctgga tgaacgggca gagcaggctt cccacagcct caagtctagt
1141 ttccccggct ctctgactgc atttttgttat gagaatgaac ttgctctgag ctgctgccag
1201 gaggaagatg aggacgatga gactgaggaa gggaatgggg tggaaacaga agatggggct
1261 gctagccccc gagttctcac accaaccctg gcgctgaccc tgcctccatg a
```

36. human Kir 3.1 - cDNA
```
   1 atgtctgcac tccgaaggaa atttgggac gattatcagg tagtgaccac atcgtccagc
  61 ggctcgggct gcagccccca ggggccaggc caggaccctc aggaggagct tgtgcccaag
 121 aagaagcggc agcggttcgt ggacaagaac ggccggtgca atgtacagca cggcaacctg
 181 ggcagcgaga caagccgcta cctctcggac ctcttcacca cgctggtgga cctcaagtgg
 241 cgctggaacc tcttcatctt cattctcacc tacaccgtgg cctggctttt catggcgtcc
 301 atgtggtggg tgatcgccta cactcggggc gacctgaaca aagcccacgt cggtaactac
 361 acgccttgcg tggccaatgt ctataacttc ccttctgcct tcctcttctt catcgagacg
 421 gaggccacca tcggctatgg ctaccgatac atcacagaca agtgccccga gggcatcatc
 481 ctcttcctct tccagtccat cctgggctcc atcgtggacg ccttcctcat cggctgcatg
 541 ttcatcaaga tgtcccagcc caagaagcgc gccgagaccc tcatgttcag cgagcacgcg
 601 gtgatctcca tgagggacgg aaaactcacg cttatgttcc gggtgggcaa cctgcgcaac
 661 agccacatgg tctccgcgca gattcgctgc aagctgctca atctcggca gacacctgag
 721 ggtgagttcc ttccccttga ccaacttgaa ctggatgtag gttttagtac aggggcagat
 781 caacttttc ttgtgtcccc cctcacaatt gccacgtga tcgatgccaa aagccccttt
 841 tatgacctat cccagcgaag catgcaaact gaacagttcg agattgtcgt catcctagaa
 901 ggcattgtgg aaacaactgg gatgacttgt caagctcgaa catcatatac tgaagatgaa
```

```
 961 gttctttggg gtcatcgttt ttttcctgta atttccttag aagagggatt ctttaaagtt 1021 gattactccc agttccatgc aacatttgaa gtccccaccc caccttacag tgtgaaagag 1081 caggaggaaa tgcttctcat gtcgtcccct ttaatagcac cagccataac taacagcaaa 1141 gaaagacata attctgtgga atgcttagat ggactagatg atattactac aaaactacca 1201 tctaagctgc agaaaattac tggaagagaa gactttccca aaaaactctt gaggatgagt 1261 tctacaactt cagaaaaagc ctacagcttg ggagacttgc ccatgaaact tcaacgaata 1321 agttcagttc cgggcaactc agaagaaaaa ctggtatcta aaaccaccaa gatgttatct 1381 gatcccatga gccagtctgt ggctgatttg ccaccaaagc ttcaaaagat ggctggagga 1441 gcagctagga tggaagggaa ccttccagcc aaattaagaa aaatgaactc tgatcgcttc 1501 acataa
```

37. human Kir 3.4 - cDNA
```
   1 atggctggcg attctaggaa tgccatgaac caggacatgg agattggagt cactccctgg 61 gaccccaaga agattccaaa acaggcccgc gattatgtcc ccattgccac agaccgtacg 121 cgcctgctgc ccgagggcaa gaagccacgc cagcgctaca tggagaagag tggcaagtgc 181 aacgtgcacc acggcaacgt ccaggagacc taccggtacc tgagtgacct cttccaccac 241 ctggtggacc tcaagtggcg cttcaacttg ctcgtcttca ccatggtttta cactgtcacc 301 tggctgttct tcggcttcat ttggtggctc attgcttata ccggggtga cctggaccat 361 gttggcgacc aagagtggat tccttgtgtt gaaaacctca gtggcttcgt gtccgctttc 421 ctgttctcca ttgagaccga aacaaccatt gggtatggct tccgagtcat cacagagaag 481 tgtccagagg ggattatact cctcttggtc caggccatcc tgggctccat cgtcaatgcc 541 ttcatggtgg ggtgcatgtt tgtcaagatc agccagccca agaagagagc ggagaccctc 601 atgttttcca caacgcagt catctccatg cgggacgaga gctgtgcct catgttccgg 661 gttggcgacc tccgcaactc ccacatcgtg gaggcctcca tccgggccaa gctcatcaag 721 tcccggcaga ccaaagaggg ggagttcatc cccctgaacc agacagacat caacgtgggc 781 tttgacacgg gcgacgaccg cctcttcctt gtgtctcctc tgatcatctc ccatgagatc 841 aaccagaaga gccctttctg ggagatgtct caggctcagc tgcatcagga gagtttgaa 901 gttgtggtca ttctagaagg gatggtggaa gccacaggca tgacctgcca agcccggagc 961 tcctacatgg atacagaggt gctctggggc caccgattca ccaccatcct caccttggaa 1021 aagggcttct atgaggtgga ctacaacacc ttccatgata cctatgagac caacacaccc 1081 agctgctgtg ccaaggagct ggcagaaatg aagagggaag gccggctcct ccagtacctc 1141 cccagccccc cactgctggg gggctgtgct gaggcagggc tggatgcaga ggctgagcag 1201 aatgaagaag atgagcccaa ggggctgggt gggtccaggg aggccagggg ctcggtgtga
```

38. human Kir 4.1 - cDNA
```
   1 atgacgtcag ttgccaaggt gtattacagt cagaccactc agacagaaag ccggccccta 61 atgggcccag ggatacgacg gcggagagtc ctgacaaaag atggtcgcag caacgtgaga 121 atggagcaca ttgccgacaa gcgcttcctc tacctcaagg acctgtggac aaccttcatt 181 gacatgcagt ggcgctacaa gcttctgctc ttctctgcga cctttgcagg cacatggttc 241 ctctttggcg tggtgtggta tctggtagct gtggcacatg gggacctgct ggagctggac 301 ccccggcca accacaccc ctgtgtggta caggtgcaca cactcactgg agccttcctc
```

```
        SEQUENCES:

361 ttctcccttg aatcccaaac caccattggc tatggcttcc gctacatcag tgaggaatgt 421 ccactggcca ttgtgcttct tattgcccag ctggtgctca ccaccatcct ggaaatcttc 481 atcacaggta ccttcctggc gaagattgcc cggcccaaga agcgggctga gaccattcgt 541 ttcagccagc atgcagttgt ggcctccac aatggcaagc cctgcctcat gatccgagtt 601 gccaatatgc gcaaaagcct cctcattggc tgccaggtga caggaaaact gcttcagacc 661 caccaaacca aggaagggga gaacatccgg ctcaaccagg tcaatgtgac tttccaagta 721 gacacagcct ctgacagccc cttccttatt ctacccctta ccttctatca tgtggtagat 781 gagaccagtc ccttgaaaga tctccctctt cgcagtggtg agggtgactt tgagctggtg 841 ctgatcctaa gtgggacagt ggagtccacc agtgccacct gtcaggtgcg cacttcctac 901 ctgccagagg agatcctttg gggctacgag ttcacacctg ccatctcact gtcagccagt 961 ggtaaataca tagctgactt tagccttttt gaccaagttg tgaaagtggc ctctcctagt 1021 ggcctccgtg acagcactgt acgctacgga gaccctgaaa agctcaagtt ggaggagtca 1081 ttaagggagc aagctgagaa ggagggcagt gcccttagtg tgcgcatcag caatgtctga 39. human Kir 4.2 – cDNA
    1 atggatgcca ttcacatcgg catgtccagc acccccctgg tgaagcacac tgctggggct 61 gggctcaagg ccaacagacc ccgcgtcatg tccaagagtg ggcacagcaa cgtgagaatt 121 gacaaagtgg atggcatata cctactctac ctgcaagacc tgtggaccac agttatcgac 181 atgaagtgga gatacaaact caccctgttc gctgccactt ttgtgatgac ctggttcctt 241 tttggagtca tctactatgc catcgcgttt attcatgggg acttagaacc cggtgagccc 301 atttcaaatc ataccccctg catcatgaaa gtggactctc tcactgggc gtttctcttt 361 tccctggaat cccagacaac cattggctat ggagtccgtt ccatcacaga ggaatgtcct 421 catgccatct cctgttggt tgctcagttg gtcatcacga ccttgattga gatcttcatc 481 accggaacct tcctggccaa aatcgccaga cccaaaaagc gggctgagac catcaagttc 541 agccactgtg cagtcatcac caagcagaat gggaagctgt gcttggtgat tcaggtagcc 601 aatatgagga gagcctctt gattcagtgc cagctctctg caagctcct gcagacccac 661 gtcaccaagg aggggagcg gattctcctc aaccaagcca ctgtcaaatt ccacgtggac 721 tcctcctctg agagcccctt cctcattctg cccatgacat tctaccatgt gctggatgag 781 acgagccccc tgagagacct cacacccaa aacctaaagg agaaggagtt tgagcttgtg 841 gtcctcctca atgccactgt ggaatccacc agcgctgtct gccagagccg aacatcttat 901 atcccagagg aaatctactg ggttttgag tttgtgcctg tggtatctct ctccaaaat 961 ggaaatatg tggctgattt cagtcagtt gaacagattc ggaaaagccc agattgcaca 1021 ttttactgtg cagattctga gaaacagcaa ctcgaggaga agtacaggca ggaggatcag 1081 agggaaagag aactgaggac actttatta caacagagca atgtctga 40. human Kir 5.1 – cDNA
    1 atgagctatt acggcagcag ctatcatatt atcaatgcgg acgcaaaata cccaggctac 61 ccgccagagc acattatagc tgagaagaga agagcaagaa gacgattact tcacaaagat 121 ggcagctgta atgtctactt caagcacatt tttggagaat ggggaagcta tgtggttgac 181 atcttcacca ctcttgtgga caccaagtgg cgccatatgt ttgtgatatt ttctttatct 241 tatattctct cgtggttgat atttggctct gtcttttggc tcatagcctt tcatcatggc 301 gatctattaa atgatccaga catcacacct tgtgttgaca acgtccattc tttcacaggg
```

```
 361 gcctttttgt tctccctaga gacccaaacc accataggat atggttatcg ctgtgttact
 421 gaagaatgtt ctgtggccgt gctcatggtg atcctccagt ccatcttaag ttgcatcata
 481 aatacccttta tcattggagc tgccttggcc aaaatggcaa ctgctcgaaa gagagcccaa
 541 accattcgtt tcagctactt tgcacttata ggtatgagag atgggaagct ttgcctcatg
 601 tggcgcattg gtgattttcg ccaaaccac gtggtagaag aacagttag agcccaactt
 661 ctccgctata cagaagacag tgaagggagg atgacgatgg catttaaaga cctcaaatta
 721 gtcaacgacc aaatcatcct ggtcaccccg gtaactattg tccatgaaat tgaccatgag
 781 agccctctgt atgcccttga ccgcaaagca gtagccaaag ataactttga gattttggtg
 841 acatttatct atactggtga ttccactgga acatctcacc aatctagaag ctcctatgtt
 901 ccccgagaaa ttctctgggg ccataggttt aatgatgtct tggaagttaa gaggaagtat
 961 tacaaagtga actgcttaca gtttgaagga agtgtggaag tatatgcccc cttttgcagt
1021 gccaagcaat tggactggaa agaccagcag ctccacatag aaaaagcacc accagttcga
1081 gaatcctgca cgtcggacac caaggcgaga cgaaggtcat ttagtgcagt tgccattgtc
1141 agcagctgtg aaaaccctga ggagaccacc acttccgcca cacatgaata tagggaaaca
1201 ccttatcaga aagctctcct gactttaaac agaatctctg tagaatccca aatgtag
```

41. human Kir 6.1 – cDNA

```
   1 atgttggcca gaaagagtat catcccggag gagaatgtgc tggcgcgcat cgccgcagag
  61 aacctgcgca agccgcgcat ccgagaccgc ctccccaaag cccgcttcat cgccaagagc
 121 ggggcctgca acctggcgca taagaacatc cgtgagcaag gacgctttct acaggacatc
 181 ttcaccacct tggtggacct gaaatggcgc acacgctgg tcatctttac catgtccttc
 241 ctctgcagct ggctgctctt cgctatcatg tggtggctgg tggcctttgc ccatgggac
 301 atctatgctt acatggagaa aagtggaatg agagaaaagtg gtttggagtc cactgtgtgt
 361 gtgactaatg tcaggtctttt cacttctgct tttctcttct ccattgaagt tcaagttacc
 421 attgggtttg gagggaggat gatgacagag gaatgcccct tggccatcac ggttttgatt
 481 ctccagaata ttgtgggttt gatcatcaat gcagtcatgt taggctgcat tttcatgaaa
 541 acagctcagg ctcacagaag ggcagaaact ttgattttca gccgccatgc tgtgattgcc
 601 gtccgaaatg gcaagctgtg cttcatgttc cgagtgggtg acctgaggaa aagcatgatc
 661 attagtgcct ctgtgcgcat ccaggtggtc aagaaaacaa ctacacctga aggggaggtg
 721 gttcctattc accaactgga cattcctgtt gataacccaa tcgagagcaa taacattttt
 781 ctggtggccc ctttgatcat ctgccacgtg attgacaagc gcagtcccct gtatgacatc
 841 tcagcaactg acctggccaa ccaagacttg gaggtcatag ttattctgga aggagtggtt
 901 gaaactactg gcatcaccac acaagcacga acctcctaca ttgctgagga gatccaatgg
 961 ggccaccgct ttgtgtccat tgtgactgag aagaaggag tgtattctgt ggattactcc
1021 aaatttggca acactgttaa agtagctgct ccacggtgca gtgcccgaga gctggatgag
1081 aaaccttcca tccttattca gaccctccaa agagtgaact gtctcatca aaattctctg
1141 aggaagcgca actccatgag aagaaacaat tccatgagga ggaacaattc tatccgaagg
1201 aacaattctt ccctcatggt accaaaggtg caatttatga ctccagaagg aaatcaaaac
1261 acatcggaat catga
```

SEQUENCES:

42. human Kir 6.2 - cDNA
```
   1 atgctgtccc gcaagggcat catccccgag gaatacgtgc tgacacgcct ggcagaggac
  61 cctgccaagc ccaggtaccg tgcccgccag cggagggccc gctttgtgtc caagaaaggc
 121 aactgcaacg tggcccacaa gaacatccgg agcagggcc gcttcctgca ggacgtgttc
 181 accacgctgg tggacctcaa gtggccacac acattgctca tcttcaccat gtccttcctg
 241 tgcagctggc tgctcttcgc catggcctgg tgctcatcg ccttcgccca cggtgacctg
 301 gccccagcg agggcactgc tgagccctgt gtcaccagca tccactcctt ctcgtctgcc
 361 ttcctttct ccattgaggt ccaagtgact attggctttg ggggcgcat ggtgactgag
 421 gagtgcccac tggccatcct gatcctcatc gtgcagaaca tcgtgggct catgatcaac
 481 gccatcatgc ttggctgcat cttcatgaag actgcccaag cccaccgcag ggctgagacc
 541 ctcatcttca gcaagcatgc ggtgatcgcc ctgcgccacg ccgcctctg catcatgcta
 601 cgtgtgggtg acctccgcaa gagcatgatc atcagcgcca ccatccacat gcaggtggta
 661 cgcaagacca ccagccccga gggcgaggtg gtgcccctcc accaggtgga catccccatg
 721 gagaacggcg tgggtggcaa cagcatcttc ctggtggccc cgctgatcat ctaccatgtc
 781 attgatgcca acagcccact ctacgacctg gcacccagcg acctgcacca ccaccaggac
 841 ctcgagatca tcgtcatcct ggaaggcgtg gtggaaacca cggcatcac cacccaggcc
 901 cgcacctcct acctggccga tgagatcctg tggggccagc gctttgtgcc cattgtagct
 961 gaggaggacg gacgttactc tgtggactac tccaagtttg caacaccgt caaagtgccc
1021 acaccactct gcacggcccg ccagcttgat gaggaccaca gcctactgga agctctgacc
1081 ctcgcctcag cccgcgggcc cctgcgcaag cgcagcgtgc ccatggccaa ggccaagccc
1141 aagttcagca tctctccaga ttccctgtcc tga
```

43. human Kir 7.1 - cDNA
```
   1 atggacagca gtaattgcaa agttattgct cctctcctaa gtcaaagata ccggaggatg
  61 gtcaccaagg atggccacag cacacttcaa atggatggcg ctcaaagagg tcttgcatat
 121 cttcgagatg cttggggaat cctaatggac atgcgctggc gttggatgat gttggtcttt
 181 tctgcttctt ttgttgtcca ctggcttgtc tttgcagtgc tctggtatgt tctggctgag
 241 atgaatggtg atctggaact agatcatgat gccccacctg aaaaccacac tatctgtgtc
 301 aagtatatca ccagtttcac agctgcattc tccttctccc tggagacaca actcacaatt
 361 ggttatggta ccatgttccc cagtggtgac tgtccaagtg caatcgcctt acttgccata
 421 caaatgctcc taggcctcat gctagaggct tttatcacag gtgcttttgt ggcgaagatt
 481 gcccggccaa aaaatcgagc ttttttcaatt cgctttactg acacagcagt agtagctcac
 541 atggatggca aacctaatct tatcttccaa gtggccaaca cccgacctag ccctctaacc
 601 agtgtccggg tctcagctgt actctatcag gaaagagaaa atggcaaact ctaccagacc
 661 agtgtggatt ccaccttga tggcatcagt tctgacgaat gtccattctt catctttcca
 721 ctaacgtact atcactccat tacaccatca agtcctctgg ctactctgct ccagcatgaa
 781 aatccttctc acttttgaatt agtagtattc ctttcagcaa tgcaggaggg cactggagaa
 841 atatgccaaa ggaggacatc ctacctaccg tctgaaatca tgttacatca ctgttttgca
 901 tctctgttga cccgaggttc caaaggtgaa tatcaaatca agatggagaa ttttgacaag
 961 actgtccctg aatttccaac tcctctggtt tctaaaagcc caaacaggac tgacctggat
```

```
                              SEQUENCES:
1021 atccacatca atggacaaag cattgacaat tttcagatct ctgaaacagg actgacagaa 1081 taa 44. chicken Kir 2.1 - cDNA
   1 atgggcagcg tgcgaaccaa ccgctacagc atcgtgtctt cggaagagga cggcatgaag 61 ctggcaacca tggccgttgc caatggcttt gggaatggaa aaagtaaggt acacaccagg 121 cagcagtgca ggagccgctt tgtcaaaaaa gatggccact gcaacgtcca gtttattaat 181 gtgggtgaga agggacagcg atacctcgca gacatcttca ccacttgcgt ggacatccgc 241 tggaggtgga tgctggttat cttctgcctg acattcatcc tctcctggct tttctttggc 301 tgtgtgtttt ggttgattgc gctgttgcac ggggatctgg agaaccaaga aaataacaaa 361 ccgtgtgtct cgcaagtgag cagcttcact gcagcctttc tgttctccat gagacccag 421 accacgatcg gctatggctt caggtgcgtc acagacgagt gccccattgc tgttttcatg 481 gtggttttcc agtctatagt aggctgcatc attgacgcct tcatcattgg tgccgtcatg 541 gcaaagatgg ctaagccaaa aaagagaaac gaaactcttg tcttcagcca caatgccgtg 601 gtggccatga gagatgggaa actgtgcctg atgtggcgtg tcggaaacct gaggaaaagc 661 cacttggttg aggcacacgt gcgagcacag ctcctcaagt ccaggatcac gtcagaaggg 721 gagtacatcc ctttggatga aatagacatc aatgtagggt ttgacagcgg gatagaccgc 781 atattcctgg tctccccaat tacaatagta cacgaaatag atgaagatag tcctttgtat 841 gacttgagca acaagacat ggacaatgct gactttgaaa ttgtagtcat tttagagggc 901 atggtggaag ccactgccat gactacccag tgccgcagct catatctggc aaatgaaatc 961 ctctggggcc accgctatga gcccgtactc tttgaagaaa aaaactacta caaagtggac 1021 tattcaaggt tccacaaaac atacgaagtg cccaacacac ccatctgcag tgccagagac 1081 ttagcagaaa agaaatacat tctctcgaac gcaaactcct tttgctacga gaacgaagtg 1141 gccctcacca gcaaggagga ggacgagatc gacacgggg tgcccgagag cacaagcaca 1201 gacacccacc ccgacatgga ccaccacaac caggcaggag tgcccctaga gccacggccg 1261 ctgcggcgtg agtcggaaat atga 45. chicken Kir 2.2 - cDNA
   1 atgactgcag gcagggtcaa cccttacagc atagtgtcct ccgaggaaga cggactgagg 61 ttgaccacca tgccagggat taacggcttt ggcaatggga aaatccacac caggaggaaa 121 tgcaggaaca ggtttgtaaa gaagaacggt cagtgcaatg tggagttcac caacatggat 181 gacaagccac agaggtacat tgcagacatg ttcaccacgt gcgttgacat ccgttggagg 241 tatatgctct tgctcttctc cctggcattt ctggtatcct ggttattgtt tgggctgatt 301 ttctggctaa ttgcactcat tcatggagat ctagaaaacc caggtggaga tgataccttc 361 aagccttgcg ttctgcagga caatggcttt gtggctgctt ttctgttctc catcgagacc 421 caaacgacta ttggttatgg cttccgctgt gtgacagagg agtgcccgct cgcagtcttc 481 atggtggtgg ttcagtccat cgtggggtgt ataatcgact ctttcatgat tggtgcaata 541 atggcaaaga tggccaggcc caaaaaaagg gcccagacat tgcttttcag ccataatgca 601 gtagtggcaa tgagagatgg aaaactctgc ctgatgtgga gagttgggaa tctccggaaa 661 agccacatag tagaagccca cgtacgagct caattaatta gcccagaat cacagaagaa 721 ggggagtaca tcccactcga ccaaatagac atcgacgtgg ggtttgacaa aggcttggac 781 cgaatcttct tggtgtcccc cattaccatt ctccatgaga tcaacgaaga cagcccgctg
```

```
 841 ttcgggatca gccgccagga cttggagacg gatgactttg agattgtggt catcctcgaa 901 ggcatggtag aagccaccgc gatgacgaca caagctcgga gctcctacct ggccagcgag 961 atcctgtggg gccaccgctt cgagcccgtc ttgttcgagg agaaaaacca gtacaaagta 1021 gactattccc acttccacaa aacatacgag gtcccgtcca caccccgctg cagcgccaag 1081 gacttggtgg agaacaaatt cctgctgccc agcaccaact ccttctgcta cgagaatgag 1141 ctggccttca tgagccgcga tgaggatgag gaggatgatg acagcagggg tttggacgac 1201 ctgagcccag acaacaggca cgagttcgac cggcttcagg caacgatagc gttggatcag 1261 aggtcatacc ggagggagtc agaaatatga
```

46. human Kir 1.1 - turret region
HKDLPEFHPSANHTPCVENING 47. human Kir 1.2 - turret region
HGDLLELDPPANHTPCVVQVHT 48. human Kir 2.1 - turret region
HGDLDASKEGKACVSEVNS 49. human Kir 2.2 - turret region
HGDLEPAEGRGRTPCVMQVHG 50. human Kir 2.3 - turret region
HGDLEASPGVPAAGGPAAGGGAAPVAPKPCIMHVNG 51. human Kir 2.4 - turret region
HGDLAAPPPPAPCFSHVAS 52. human Kir 3.1 - turret region
RGDLNKAHVGNYTPCVANVYN 53. human Kir 3.4 - turret region
RGDLDHVGDQEWIPCVENLSG 54. human Kir 6.1 - turret region
HGDIYAYMEKSGMEKSGLESTVCVTNVRS 55. human Kir 6.2 - turret region
HGDLAPSEGTAEPCVTSIHS 56. human Kir 7.1 - turret region
NGDLELDHDAPPENHTICVKYITS 57. chicken Kir 2.1 - turret region
HGDLENQENNKPCVSQVSS 58. chicken Kir 2.2 - turret region
HGDLENPGGDDTFKPCVLQVNG 59. Kir Bac 1.1 - turret region
SPARKPPRGGRRIWSGTREVIAYGMPASVWRDLYYWALKVSWPVFFASLAALF

VVNNTLFALLYQLGDAPIANQSPPGFVGAFFFSVETLATVGYGDMHPQTVYAHA

IATLEIFVGMSGIALSTGLVFARFARPRAKIMFARHAIVRPFNGRMTLMVRAANA

RQNVIAEARAKMRLMRREHSSEGYSLMKIHDLKLVRNEHPIFLLGWNMMHVID

ESSPLFGETPESLAEGRAMLLVMIEGSDETTAQVMQARHAWEHDDIRWHHRYV

DLMSDVDGMTHIDYTRFNDTEPVEPPGAAPDAQAFAAKPGE

60. KcsA - turret region
MAPMLSGLLARLVKLLLGRHGSALHWRAAGAATVLLVIVLLAGSYLAVLAERG

APGAQLITYPRALWWSVETATTVGYGDLYPVTLWGRCVAVVVMVAGITSFGLV

TAALATWFVGREQERRGH

| SEQUENCES: |
|---|
| 61. rKv1.2 - turret region<br>MRELGLLIFFLFIGVILFSSAVYFAEADERDSQFPSIPDAFWWAVVSMTTVGYGD<br><br>MVPTTIGGKIVGSLCAIAGVLTIALPVPVIVSNFNYFYHRETEGE |

I claim:

1. A purified antibody that specifically binds to an epitope in the turret region of a Kir channel selected from the group consisting of Kir 1.1, Kir 1.2, Kir 2.1, Kir 2.2, Kir 2.3, Kir 2.4, Kir 3.1, Kir 3.4, Kir 6.1, Kir 6.2 and Kir 7.1.

2. The purified antibody of claim 1 wherein said antibody is human, chimeric or humanized.

3. The purified antibody of claim 1, wherein the antibody is selected from the group consisting of a polyclonal antibody, a monoclonal antibody, an intact immunoglobulin molecule, an antibody fragment, a scFv, a Fab, a F(ab)2, a Fv, and a disulfide linked Fv.

4. The purified antibody of claim 1, wherein the Kir channel is human.

5. The purified antibody of claim 1, wherein the epitope is within the variable portion of the turret region.

6. The purified antibody of claim 5, wherein the epitope is within the sequence of SEQ ID NOS: 1, 2, 3, 4, 5, 6, 7, 8, 9, 10, or 11.

7. A method of making an antibody that specifically binds to an epitope in the turret region of a human Kir channel, comprising
   providing a chicken/human hybrid Kir channel, wherein the chicken/human hybrid comprises a human Kir channel turret region;
   immunizing a non-human animal with the chicken/human hybrid Kir channel; and
   determining whether the antibody is binding to the human Kir channel turret region,
   wherein the human Kir channel is selected from the group consisting of Kir 1.1, Kir 1.2, Kir 2.1, Kir 2.2, Kir 2.3, Kir 2.4, Kir 3.1, Kir 3.4, Kir 6.1, Kir 6.2 and Kir 7.1.

8. The method of claim 7, wherein the chicken portion of the chicken/human hybrid Kir channel is obtained from a chicken Kir2.2 channel.

9. The method of claim 8, wherein the human Kir channel turret region is the amino acid sequence comprising SEQ ID NOS: 46, 47, 48, 49, 50, 51, 52, 53, 54, 55, or 56.

10. A method of making an antibody that specifically binds to an epitope in the turret region of a human Kir channel, comprising
    providing a human Kir channel
    immunizing a non-human animal with the Kir channel; and
    determining whether the antibody is binding to the human Kir channel turret region,
wherein the human Kir channel is selected from the group consisting of Kir 1.1, Kir 1.2, Kir 2.1, Kir 2.2, Kir 2.3, Kir 2.4, Kir 3.1, Kir 3.4, Kir 6.1, Kir 6.2 and Kir 7.1.

11. The method of claim 10, wherein the human Kir channel turret region is the amino acid sequence comprising SEQ ID NOS: 46, 47, 48, 49, 50, 51, 52, 53, 54, 55, or 56.

\* \* \* \* \*

SEQUENCE LISTING

<160> NUMBER OF SEQ ID NOS: 61

<210> SEQ ID NO 1
<211> LENGTH: 11
<212> TYPE: PRT
<213> ORGANISM: Homo sapiens

<400> SEQUENCE: 1

Pro Glu Phe His Pro Ser Ala Asn His Thr Pro
1               5                   10

<210> SEQ ID NO 2
<211> LENGTH: 11
<212> TYPE: PRT
<213> ORGANISM: Homo sapiens

<400> SEQUENCE: 2

Leu Glu Leu Asp Pro Pro Ala Asn His Thr Pro
1               5                   10

<210> SEQ ID NO 3
<211> LENGTH: 8
<212> TYPE: PRT
<213> ORGANISM: Homo sapiens

<400> SEQUENCE: 3

Asp Ala Ser Lys Glu Gly Lys Ala
1               5

<210> SEQ ID NO 4
<211> LENGTH: 10
<212> TYPE: PRT
<213> ORGANISM: Homo sapiens

<400> SEQUENCE: 4

Glu Pro Ala Glu Gly Arg Gly Arg Thr Pro
1               5                   10

<210> SEQ ID NO 5
<211> LENGTH: 26
<212> TYPE: PRT
<213> ORGANISM: Homo sapiens

<400> SEQUENCE: 5

Glu Ala Ser Pro Gly Val Pro Ala Ala Gly Pro Ala Ala Gly Gly
1               5                   10                  15

Gly Gly Ala Ala Pro Val Ala Pro Lys Pro
            20                  25

<210> SEQ ID NO 6
<211> LENGTH: 8
<212> TYPE: PRT
<213> ORGANISM: Homo sapiens

<400> SEQUENCE: 6

```
Ala Ala Pro Pro Pro Ala Pro
1               5

<210> SEQ ID NO 7
<211> LENGTH: 10
<212> TYPE: PRT
<213> ORGANISM: Homo sapiens

<400> SEQUENCE: 7

Asn Lys Ala His Val Gly Asn Tyr Thr Pro
1               5                   10

<210> SEQ ID NO 8
<211> LENGTH: 10
<212> TYPE: PRT
<213> ORGANISM: Homo sapiens

<400> SEQUENCE: 8

Asp His Val Gly Asp Gln Glu Trp Ile Pro
1               5                   10

<210> SEQ ID NO 9
<211> LENGTH: 18
<212> TYPE: PRT
<213> ORGANISM: Homo sapiens

<400> SEQUENCE: 9

Tyr Ala Tyr Met Glu Lys Ser Gly Met Glu Lys Ser Gly Leu Glu Ser
1               5                   10                  15

Thr Val

<210> SEQ ID NO 10
<211> LENGTH: 9
<212> TYPE: PRT
<213> ORGANISM: Homo sapiens

<400> SEQUENCE: 10

Ala Pro Ser Glu Gly Thr Ala Glu Pro
1               5

<210> SEQ ID NO 11
<211> LENGTH: 13
<212> TYPE: PRT
<213> ORGANISM: Homo sapiens

<400> SEQUENCE: 11

Glu Leu Asp His Asp Ala Pro Pro Glu Asn His Thr Ile
1               5                   10

<210> SEQ ID NO 12
<211> LENGTH: 8
<212> TYPE: PRT
<213> ORGANISM: Gallus gallus

<400> SEQUENCE: 12

Glu Asn Gln Glu Asn Asn Lys Pro
1               5

<210> SEQ ID NO 13
<211> LENGTH: 11
<212> TYPE: PRT
<213> ORGANISM: Gallus gallus

<400> SEQUENCE: 13
```

```
Glu Asn Pro Gly Gly Asp Asp Thr Phe Lys Pro
1               5                   10
```

<210> SEQ ID NO 14
<211> LENGTH: 391
<212> TYPE: PRT
<213> ORGANISM: Homo sapiens

<400> SEQUENCE: 14

```
Met Asn Ala Ser Ser Arg Asn Val Phe Asp Thr Leu Ile Arg Val Leu
1               5                   10                  15

Thr Glu Ser Met Phe Lys His Leu Arg Lys Trp Val Val Thr Arg Phe
            20                  25                  30

Phe Gly His Ser Arg Gln Arg Ala Arg Leu Val Ser Lys Asp Gly Arg
        35                  40                  45

Cys Asn Ile Glu Phe Gly Asn Val Glu Ala Gln Ser Arg Phe Ile Phe
    50                  55                  60

Phe Val Asp Ile Trp Thr Thr Val Leu Asp Leu Lys Trp Arg Tyr Lys
65                  70                  75                  80

Met Thr Ile Phe Ile Thr Ala Phe Leu Gly Ser Trp Phe Phe Gly
                    85                  90                  95

Leu Leu Trp Tyr Ala Val Ala Tyr Ile His Lys Asp Leu Pro Glu Phe
            100                 105                 110

His Pro Ser Ala Asn His Thr Pro Cys Val Glu Asn Ile Asn Gly Leu
        115                 120                 125

Thr Ser Ala Phe Leu Phe Ser Leu Glu Thr Gln Val Thr Ile Gly Tyr
    130                 135                 140

Gly Phe Arg Cys Val Thr Glu Gln Cys Ala Thr Ala Ile Phe Leu Leu
145                 150                 155                 160

Ile Phe Gln Ser Ile Leu Gly Val Ile Ile Asn Ser Phe Met Cys Gly
                    165                 170                 175

Ala Ile Leu Ala Lys Ile Ser Arg Pro Lys Lys Arg Ala Lys Thr Ile
            180                 185                 190

Thr Phe Ser Lys Asn Ala Val Ile Ser Lys Arg Gly Gly Lys Leu Cys
        195                 200                 205

Leu Leu Ile Arg Val Ala Asn Leu Arg Lys Ser Leu Leu Ile Gly Ser
    210                 215                 220

His Ile Tyr Gly Lys Leu Leu Lys Thr Thr Val Thr Pro Glu Gly Glu
225                 230                 235                 240

Thr Ile Ile Leu Asp Gln Ile Asn Ile Asn Phe Val Val Asp Ala Gly
                    245                 250                 255

Asn Glu Asn Leu Phe Phe Ile Ser Pro Leu Thr Ile Tyr His Val Ile
            260                 265                 270

Asp His Asn Ser Pro Phe Phe His Met Ala Ala Glu Thr Leu Leu Gln
        275                 280                 285

Gln Asp Phe Glu Leu Val Val Phe Leu Asp Gly Thr Val Glu Ser Thr
    290                 295                 300

Ser Ala Thr Cys Gln Val Arg Thr Ser Tyr Val Pro Glu Glu Val Leu
305                 310                 315                 320

Trp Gly Tyr Arg Phe Ala Pro Ile Val Ser Lys Thr Lys Glu Gly Lys
                    325                 330                 335

Tyr Arg Val Asp Phe His Asn Phe Ser Lys Thr Val Glu Val Glu Thr
            340                 345                 350

Pro His Cys Ala Met Cys Leu Tyr Asn Glu Lys Asp Val Arg Ala Arg
```

```
                355                 360                 365
Met Lys Arg Gly Tyr Asp Asn Pro Asn Phe Ile Leu Ser Glu Val Asn
        370                 375                 380

Glu Thr Asp Asp Thr Lys Met
385                 390

<210> SEQ ID NO 15
<211> LENGTH: 379
<212> TYPE: PRT
<213> ORGANISM: Homo sapiens

<400> SEQUENCE: 15

Met Thr Ser Val Ala Lys Val Tyr Tyr Ser Gln Thr Thr Gln Thr Glu
1               5                   10                  15

Ser Arg Pro Leu Met Gly Pro Gly Ile Arg Arg Arg Val Leu Thr
            20                  25                  30

Lys Asp Gly Arg Ser Asn Val Arg Met Glu His Ile Ala Asp Lys Arg
            35                  40                  45

Phe Leu Tyr Leu Lys Asp Leu Trp Thr Thr Phe Ile Asp Met Gln Trp
    50                  55                  60

Arg Tyr Lys Leu Leu Phe Ser Ala Thr Phe Ala Gly Thr Trp Phe
65                  70                  75                  80

Leu Phe Gly Val Val Trp Tyr Leu Val Ala Val Ala His Gly Asp Leu
                    85                  90                  95

Leu Glu Leu Asp Pro Pro Ala Asn His Thr Pro Cys Val Val Gln Val
                100                 105                 110

His Thr Leu Thr Gly Ala Phe Leu Phe Ser Leu Glu Ser Gln Thr Thr
            115                 120                 125

Ile Gly Tyr Gly Phe Arg Tyr Ile Ser Glu Glu Cys Pro Leu Ala Ile
            130                 135                 140

Val Leu Leu Ile Ala Gln Leu Val Leu Thr Thr Ile Leu Glu Ile Phe
145                 150                 155                 160

Ile Thr Gly Thr Phe Leu Ala Lys Ile Ala Arg Pro Lys Lys Arg Ala
                    165                 170                 175

Glu Thr Ile Arg Phe Ser Gln His Ala Val Val Ala Ser His Asn Gly
                180                 185                 190

Lys Pro Cys Leu Met Ile Arg Val Ala Asn Met Arg Lys Ser Leu Leu
            195                 200                 205

Ile Gly Cys Gln Val Thr Gly Lys Leu Leu Gln Thr His Gln Thr Lys
            210                 215                 220

Glu Gly Glu Asn Ile Arg Leu Asn Gln Val Asn Val Thr Phe Gln Val
225                 230                 235                 240

Asp Thr Ala Ser Asp Ser Pro Phe Leu Ile Leu Pro Leu Thr Phe Tyr
                    245                 250                 255

His Val Val Asp Glu Thr Ser Pro Leu Lys Asp Leu Pro Leu Arg Ser
                260                 265                 270

Gly Glu Gly Asp Phe Glu Leu Val Leu Ile Leu Ser Gly Thr Val Glu
            275                 280                 285

Ser Thr Ser Ala Thr Cys Gln Val Arg Thr Ser Tyr Leu Pro Glu Glu
            290                 295                 300

Ile Leu Trp Gly Tyr Glu Phe Thr Pro Ala Ile Ser Leu Ser Ala Ser
305                 310                 315                 320

Gly Lys Tyr Ile Ala Asp Phe Ser Leu Phe Asp Gln Val Val Lys Val
                    325                 330                 335
```

```
Ala Ser Pro Ser Gly Leu Arg Asp Ser Thr Val Arg Tyr Gly Asp Pro
            340                 345                 350

Glu Lys Leu Lys Leu Glu Glu Ser Leu Arg Glu Gln Ala Glu Lys Glu
        355                 360                 365

Gly Ser Ala Leu Ser Val Arg Ile Ser Asn Val
    370                 375

<210> SEQ ID NO 16
<211> LENGTH: 427
<212> TYPE: PRT
<213> ORGANISM: Homo sapiens

<400> SEQUENCE: 16

Met Gly Ser Val Arg Thr Asn Arg Tyr Ser Ile Val Ser Ser Glu Glu
1               5                   10                  15

Asp Gly Met Lys Leu Ala Thr Met Ala Val Ala Asn Gly Phe Gly Asn
            20                  25                  30

Gly Lys Ser Lys Val His Thr Arg Gln Gln Cys Arg Ser Arg Phe Val
        35                  40                  45

Lys Lys Asp Gly His Cys Asn Val Gln Phe Ile Asn Val Gly Glu Lys
    50                  55                  60

Gly Gln Arg Tyr Leu Ala Asp Ile Phe Thr Thr Cys Val Asp Ile Arg
65                  70                  75                  80

Trp Arg Trp Met Leu Val Ile Phe Cys Leu Ala Phe Val Leu Ser Trp
                85                  90                  95

Leu Phe Phe Gly Cys Val Phe Trp Leu Ile Ala Leu Leu His Gly Asp
            100                 105                 110

Leu Asp Ala Ser Lys Glu Gly Lys Ala Cys Val Ser Glu Val Asn Ser
        115                 120                 125

Phe Thr Ala Ala Phe Leu Phe Ser Ile Glu Thr Gln Thr Thr Ile Gly
    130                 135                 140

Tyr Gly Phe Arg Cys Val Thr Asp Glu Cys Pro Ile Ala Val Phe Met
145                 150                 155                 160

Val Val Phe Gln Ser Ile Val Gly Cys Ile Ile Asp Ala Phe Ile Ile
                165                 170                 175

Gly Ala Val Met Ala Lys Met Ala Lys Pro Lys Lys Arg Asn Glu Thr
            180                 185                 190

Leu Val Phe Ser His Asn Ala Val Ile Ala Met Arg Asp Gly Lys Leu
        195                 200                 205

Cys Leu Met Trp Arg Val Gly Asn Leu Arg Lys Ser His Leu Val Glu
    210                 215                 220

Ala His Val Arg Ala Gln Leu Leu Lys Ser Arg Ile Thr Ser Glu Gly
225                 230                 235                 240

Glu Tyr Ile Pro Leu Asp Gln Ile Asp Ile Asn Val Gly Phe Asp Ser
                245                 250                 255

Gly Ile Asp Arg Ile Phe Leu Val Ser Pro Ile Thr Ile Val His Glu
            260                 265                 270

Ile Asp Glu Asp Ser Pro Leu Tyr Asp Leu Ser Lys Gln Asp Ile Asp
        275                 280                 285

Asn Ala Asp Phe Glu Ile Val Val Ile Leu Glu Gly Met Val Glu Ala
    290                 295                 300

Thr Ala Met Thr Thr Gln Cys Arg Ser Ser Tyr Leu Ala Asn Glu Ile
305                 310                 315                 320

Leu Trp Gly His Arg Tyr Glu Pro Val Leu Phe Glu Glu Lys His Tyr
                325                 330                 335
```

```
Tyr Lys Val Asp Tyr Ser Arg Phe His Lys Thr Tyr Glu Val Pro Asn
            340                 345                 350

Thr Pro Leu Cys Ser Ala Arg Asp Leu Ala Glu Lys Lys Tyr Ile Leu
            355                 360                 365

Ser Asn Ala Asn Ser Phe Cys Tyr Glu Asn Glu Val Ala Leu Thr Ser
370                 375                 380

Lys Glu Glu Asp Ser Glu Asn Gly Val Pro Glu Ser Thr Ser Thr
385                 390                 395                 400

Asp Thr Pro Pro Asp Ile Asp Leu His Asn Gln Ala Ser Val Pro Leu
                405                 410                 415

Glu Pro Arg Pro Leu Arg Arg Glu Ser Glu Ile
            420                 425

<210> SEQ ID NO 17
<211> LENGTH: 433
<212> TYPE: PRT
<213> ORGANISM: Homo sapiens

<400> SEQUENCE: 17

Met Thr Ala Ala Ser Arg Ala Asn Pro Tyr Ser Ile Val Ser Ser Glu
1               5                   10                  15

Glu Asp Gly Leu His Leu Val Thr Met Ser Gly Ala Asn Gly Phe Gly
            20                  25                  30

Asn Gly Lys Val His Thr Arg Arg Cys Arg Asn Arg Phe Val Lys
            35                  40                  45

Lys Asn Gly Gln Cys Asn Ile Glu Phe Ala Asn Met Asp Glu Lys Ser
50                  55                  60

Gln Arg Tyr Leu Ala Asp Met Phe Thr Thr Cys Val Asp Ile Arg Trp
65                  70                  75                  80

Arg Tyr Met Leu Leu Ile Phe Ser Leu Ala Phe Leu Ala Ser Trp Leu
                85                  90                  95

Leu Phe Gly Ile Ile Phe Trp Val Ile Ala Val Ala His Gly Asp Leu
            100                 105                 110

Glu Pro Ala Glu Gly Arg Gly Arg Thr Pro Cys Val Met Gln Val His
            115                 120                 125

Gly Phe Met Ala Ala Phe Leu Phe Ser Ile Glu Thr Gln Thr Thr Ile
130                 135                 140

Gly Tyr Gly Leu Arg Cys Val Thr Glu Glu Cys Pro Val Ala Val Phe
145                 150                 155                 160

Met Val Val Ala Gln Ser Ile Val Gly Cys Ile Ile Asp Ser Phe Met
                165                 170                 175

Ile Gly Ala Ile Met Ala Lys Met Ala Arg Pro Lys Lys Arg Ala Gln
            180                 185                 190

Thr Leu Leu Phe Ser His Asn Ala Val Val Ala Leu Arg Asp Gly Lys
            195                 200                 205

Leu Cys Leu Met Trp Arg Val Gly Asn Leu Arg Lys Ser His Ile Val
210                 215                 220

Glu Ala His Val Arg Ala Gln Leu Ile Lys Pro Arg Val Thr Glu Glu
225                 230                 235                 240

Gly Glu Tyr Ile Pro Leu Asp Gln Ile Asp Ile Asp Val Gly Phe Asp
                245                 250                 255

Lys Gly Leu Asp Arg Ile Phe Leu Val Ser Pro Ile Thr Ile Leu His
            260                 265                 270

Glu Ile Asp Glu Ala Ser Pro Leu Phe Gly Ile Ser Arg Gln Asp Leu
```

```
              275                 280                 285
Glu Thr Asp Asp Phe Glu Ile Val Val Ile Leu Glu Gly Met Val Glu
        290                 295                 300
Ala Thr Ala Met Thr Thr Gln Ala Arg Ser Ser Tyr Leu Ala Asn Glu
305                 310                 315                 320
Ile Leu Trp Gly His Arg Phe Glu Pro Val Leu Phe Glu Glu Lys Asn
                325                 330                 335
Gln Tyr Lys Ile Asp Tyr Ser His Phe His Lys Thr Tyr Glu Val Pro
            340                 345                 350
Ser Thr Pro Arg Cys Ser Ala Lys Asp Leu Val Glu Asn Lys Phe Leu
        355                 360                 365
Leu Pro Ser Ala Asn Ser Phe Cys Tyr Glu Asn Glu Leu Ala Phe Leu
    370                 375                 380
Ser Arg Asp Glu Glu Asp Glu Ala Asp Gly Asp Gln Asp Gly Arg Ser
385                 390                 395                 400
Arg Asp Gly Leu Ser Pro Gln Ala Arg His Asp Phe Asp Arg Leu Gln
                405                 410                 415
Ala Gly Gly Gly Val Leu Glu Gln Arg Pro Tyr Arg Arg Glu Ser Glu
            420                 425                 430
Ile

<210> SEQ ID NO 18
<211> LENGTH: 445
<212> TYPE: PRT
<213> ORGANISM: Homo sapiens

<400> SEQUENCE: 18

Met His Gly His Ser Arg Asn Gly Gln Ala His Val Pro Arg Arg Lys
1               5                   10                  15
Arg Arg Asn Arg Phe Val Lys Lys Asn Gly Gln Cys Asn Val Tyr Phe
                20                  25                  30
Ala Asn Leu Ser Asn Lys Ser Gln Arg Tyr Met Ala Asp Ile Phe Thr
            35                  40                  45
Thr Cys Val Asp Thr Arg Trp Arg Tyr Met Leu Met Ile Phe Ser Ala
    50                  55                  60
Ala Phe Leu Val Ser Trp Leu Phe Phe Gly Leu Leu Phe Trp Cys Ile
65                  70                  75                  80
Ala Phe Phe His Gly Asp Leu Glu Ala Ser Pro Gly Val Pro Ala Ala
                85                  90                  95
Gly Gly Pro Ala Ala Gly Gly Gly Ala Ala Pro Val Ala Pro Lys
                100                 105                 110
Pro Cys Ile Met His Val Asn Gly Phe Leu Gly Ala Phe Leu Phe Ser
            115                 120                 125
Val Glu Thr Gln Thr Thr Ile Gly Tyr Gly Phe Arg Cys Val Thr Glu
    130                 135                 140
Glu Cys Pro Leu Ala Val Ile Ala Val Val Val Gln Ser Ile Val Gly
145                 150                 155                 160
Cys Val Ile Asp Ser Phe Met Ile Gly Thr Ile Met Ala Lys Met Ala
                165                 170                 175
Arg Pro Lys Lys Arg Ala Gln Thr Leu Leu Phe Ser His His Ala Val
                180                 185                 190
Ile Ser Val Arg Asp Gly Lys Leu Cys Leu Met Trp Arg Val Gly Asn
            195                 200                 205
Leu Arg Lys Ser His Ile Val Glu Ala His Val Arg Ala Gln Leu Ile
```

```
            210                 215                 220
Lys Pro Tyr Met Thr Gln Glu Gly Glu Tyr Leu Pro Leu Asp Gln Arg
225                 230                 235                 240

Asp Leu Asn Val Gly Tyr Asp Ile Gly Leu Asp Arg Ile Phe Leu Val
                245                 250                 255

Ser Pro Ile Ile Ile Val His Glu Ile Asp Glu Asp Ser Pro Leu Tyr
            260                 265                 270

Gly Met Gly Lys Glu Glu Leu Glu Ser Glu Asp Phe Glu Ile Val Val
                275                 280                 285

Ile Leu Glu Gly Met Val Glu Ala Thr Ala Met Thr Thr Gln Ala Arg
            290                 295                 300

Ser Ser Tyr Leu Ala Ser Glu Ile Leu Trp Gly His Arg Phe Glu Pro
305                 310                 315                 320

Val Val Phe Glu Glu Lys Ser His Tyr Lys Val Asp Tyr Ser Arg Phe
                325                 330                 335

His Lys Thr Tyr Glu Val Ala Gly Thr Pro Cys Cys Ser Ala Arg Glu
                340                 345                 350

Leu Gln Glu Ser Lys Ile Thr Val Leu Pro Ala Pro Pro Pro Pro Pro
            355                 360                 365

Ser Ala Phe Cys Tyr Glu Asn Glu Leu Ala Leu Met Ser Gln Glu Glu
            370                 375                 380

Glu Glu Met Glu Glu Gly Ala Ala Ala Ala Ala Val Ala Ala Ala Gly
385                 390                 395                 400

Leu Gly Leu Glu Ala Gly Ser Lys Glu Glu Ala Gly Ile Ile Arg Met
                405                 410                 415

Leu Glu Phe Gly Ser His Leu Asp Leu Glu Arg Met Gln Ala Ser Leu
                420                 425                 430

Pro Leu Asp Asn Ile Ser Tyr Arg Arg Glu Ser Ala Ile
            435                 440                 445

<210> SEQ ID NO 19
<211> LENGTH: 436
<212> TYPE: PRT
<213> ORGANISM: Homo sapiens

<400> SEQUENCE: 19

Met Gly Leu Ala Arg Ala Leu Arg Arg Leu Ser Gly Ala Leu Asp Ser
1               5                   10                  15

Gly Asp Ser Arg Ala Gly Asp Glu Glu Glu Ala Gly Pro Gly Leu Cys
                20                  25                  30

Arg Asn Gly Trp Ala Pro Ala Pro Val Gln Ser Pro Val Gly Arg Arg
            35                  40                  45

Arg Gly Arg Phe Val Lys Lys Asp Gly His Cys Asn Val Arg Phe Val
        50                  55                  60

Asn Leu Gly Gly Gln Gly Ala Arg Tyr Leu Ser Asp Leu Phe Thr Thr
65                  70                  75                  80

Cys Val Asp Val Arg Trp Arg Trp Met Cys Leu Leu Phe Ser Cys Ser
                85                  90                  95

Phe Leu Ala Ser Trp Leu Leu Phe Gly Leu Ala Phe Trp Leu Ile Ala
            100                 105                 110

Ser Leu His Gly Asp Leu Ala Ala Pro Pro Pro Ala Pro Cys Phe
        115                 120                 125

Ser His Val Ala Ser Phe Leu Ala Ala Phe Leu Phe Ala Leu Glu Thr
        130                 135                 140
```

Gln Thr Ser Ile Gly Tyr Gly Val Arg Ser Val Thr Glu Glu Cys Pro
145                 150                 155                 160

Ala Ala Val Ala Ala Val Val Leu Gln Cys Ile Ala Gly Cys Val Leu
            165                 170                 175

Asp Ala Phe Val Val Gly Ala Val Met Ala Lys Met Ala Lys Pro Lys
            180                 185                 190

Lys Arg Asn Glu Thr Leu Val Phe Ser Glu Asn Ala Val Val Ala Leu
            195                 200                 205

Arg Asp His Arg Leu Cys Leu Met Trp Arg Val Gly Asn Leu Arg Arg
210                 215                 220

Ser His Leu Val Glu Ala His Val Arg Ala Gln Leu Leu Gln Pro Arg
225                 230                 235                 240

Val Thr Pro Glu Gly Glu Tyr Ile Pro Leu Asp His Gln Asp Val Asp
            245                 250                 255

Val Gly Phe Asp Gly Gly Thr Asp Arg Ile Phe Leu Val Ser Pro Ile
            260                 265                 270

Thr Ile Val His Glu Ile Asp Ser Ala Ser Pro Leu Tyr Glu Leu Gly
            275                 280                 285

Arg Ala Glu Leu Ala Arg Ala Asp Phe Glu Leu Val Val Ile Leu Glu
290                 295                 300

Gly Met Val Glu Ala Thr Ala Met Thr Thr Gln Cys Arg Ser Ser Tyr
305                 310                 315                 320

Leu Pro Gly Glu Leu Leu Trp Gly His Arg Phe Glu Pro Val Leu Phe
            325                 330                 335

Gln Arg Gly Ser Gln Tyr Glu Val Asp Tyr Arg His Phe His Arg Thr
            340                 345                 350

Tyr Glu Val Pro Gly Thr Pro Val Cys Ser Ala Lys Glu Leu Asp Glu
            355                 360                 365

Arg Ala Glu Gln Ala Ser His Ser Leu Lys Ser Ser Phe Pro Gly Ser
370                 375                 380

Leu Thr Ala Phe Cys Tyr Glu Asn Glu Leu Ala Leu Ser Cys Cys Gln
385                 390                 395                 400

Glu Glu Asp Glu Asp Asp Glu Thr Glu Glu Gly Asn Gly Val Glu Thr
            405                 410                 415

Glu Asp Gly Ala Ala Ser Pro Arg Val Leu Thr Pro Thr Leu Ala Leu
            420                 425                 430

Thr Leu Pro Pro
        435

<210> SEQ ID NO 20
<211> LENGTH: 501
<212> TYPE: PRT
<213> ORGANISM: Homo sapiens

<400> SEQUENCE: 20

Met Ser Ala Leu Arg Arg Lys Phe Gly Asp Asp Tyr Gln Val Val Thr
1               5                   10                  15

Thr Ser Ser Ser Gly Ser Gly Leu Gln Pro Gln Gly Pro Gly Gln Asp
            20                  25                  30

Pro Gln Gln Gln Leu Val Pro Lys Lys Arg Gln Arg Phe Val Asp
        35                  40                  45

Lys Asn Gly Arg Cys Asn Val Gln His Gly Asn Leu Gly Ser Glu Thr
    50                  55                  60

Ser Arg Tyr Leu Ser Asp Leu Phe Thr Thr Leu Val Asp Leu Lys Trp
65                  70                  75                  80

```
Arg Trp Asn Leu Phe Ile Phe Ile Leu Thr Tyr Thr Val Ala Trp Leu
                85                  90                  95

Phe Met Ala Ser Met Trp Val Ile Ala Tyr Thr Arg Gly Asp Leu
            100                 105                 110

Asn Lys Ala His Val Gly Asn Tyr Thr Pro Cys Val Ala Asn Val Tyr
            115                 120                 125

Asn Phe Pro Ser Ala Phe Leu Phe Phe Ile Glu Thr Glu Ala Thr Ile
130                 135                 140

Gly Tyr Gly Tyr Arg Tyr Ile Thr Asp Lys Cys Pro Glu Gly Ile Ile
145                 150                 155                 160

Leu Phe Leu Phe Gln Ser Ile Leu Gly Ser Ile Val Asp Ala Phe Leu
                165                 170                 175

Ile Gly Cys Met Phe Ile Lys Met Ser Gln Pro Lys Lys Arg Ala Glu
            180                 185                 190

Thr Leu Met Phe Ser Glu His Ala Val Ile Ser Met Arg Asp Gly Lys
            195                 200                 205

Leu Thr Leu Met Phe Arg Val Gly Asn Leu Arg Asn Ser His Met Val
    210                 215                 220

Ser Ala Gln Ile Arg Cys Lys Leu Leu Lys Ser Arg Gln Thr Pro Glu
225                 230                 235                 240

Gly Glu Phe Leu Pro Leu Asp Gln Leu Glu Leu Asp Val Gly Phe Ser
                245                 250                 255

Thr Gly Ala Asp Gln Leu Phe Leu Val Ser Pro Leu Thr Ile Cys His
                260                 265                 270

Val Ile Asp Ala Lys Ser Pro Phe Tyr Asp Leu Ser Gln Arg Ser Met
            275                 280                 285

Gln Thr Glu Gln Phe Glu Ile Val Val Ile Leu Glu Gly Ile Val Glu
    290                 295                 300

Thr Thr Gly Met Thr Cys Gln Ala Arg Thr Ser Tyr Thr Glu Asp Glu
305                 310                 315                 320

Val Leu Trp Gly His Arg Phe Phe Pro Val Ile Ser Leu Glu Glu Gly
                325                 330                 335

Phe Phe Lys Val Asp Tyr Ser Gln Phe His Ala Thr Phe Glu Val Pro
                340                 345                 350

Thr Pro Pro Tyr Ser Val Lys Glu Gln Glu Glu Met Leu Leu Met Ser
            355                 360                 365

Ser Pro Leu Ile Ala Pro Ala Ile Thr Asn Ser Lys Glu Arg His Asn
    370                 375                 380

Ser Val Glu Cys Leu Asp Gly Leu Asp Asp Ile Thr Thr Lys Leu Pro
385                 390                 395                 400

Ser Lys Leu Gln Lys Ile Thr Gly Arg Glu Asp Phe Pro Lys Lys Leu
                405                 410                 415

Leu Arg Met Ser Ser Thr Thr Ser Glu Lys Ala Tyr Ser Leu Gly Asp
            420                 425                 430

Leu Pro Met Lys Leu Gln Arg Ile Ser Ser Val Pro Gly Asn Ser Glu
            435                 440                 445

Glu Lys Leu Val Ser Lys Thr Thr Lys Met Leu Ser Asp Pro Met Ser
450                 455                 460

Gln Ser Val Ala Asp Leu Pro Pro Lys Leu Gln Lys Met Ala Gly Gly
465                 470                 475                 480

Ala Ala Arg Met Glu Gly Asn Leu Pro Ala Lys Leu Arg Lys Met Asn
                485                 490                 495
```

Ser Asp Arg Phe Thr
                500

<210> SEQ ID NO 21
<211> LENGTH: 419
<212> TYPE: PRT
<213> ORGANISM: Homo sapiens

<400> SEQUENCE: 21

Met Ala Gly Asp Ser Arg Asn Ala Met Asn Gln Asp Met Glu Ile Gly
1               5                   10                  15

Val Thr Pro Trp Asp Pro Lys Lys Ile Pro Lys Gln Ala Arg Asp Tyr
            20                  25                  30

Val Pro Ile Ala Thr Asp Arg Thr Arg Leu Leu Ala Glu Gly Lys Lys
        35                  40                  45

Pro Arg Gln Arg Tyr Met Glu Lys Ser Gly Lys Cys Asn Val His His
    50                  55                  60

Gly Asn Val Gln Glu Thr Tyr Arg Tyr Leu Ser Asp Leu Phe Thr Thr
65                  70                  75                  80

Leu Val Asp Leu Lys Trp Arg Phe Asn Leu Leu Val Phe Thr Met Val
                85                  90                  95

Tyr Thr Val Thr Trp Leu Phe Phe Gly Phe Ile Trp Trp Leu Ile Ala
            100                 105                 110

Tyr Ile Arg Gly Asp Leu Asp His Val Gly Asp Gln Gly Trp Ile Pro
        115                 120                 125

Cys Val Glu Asn Leu Ser Gly Phe Val Ser Ala Phe Leu Phe Ser Ile
    130                 135                 140

Glu Thr Glu Thr Thr Ile Gly Tyr Gly Phe Arg Val Ile Thr Glu Lys
145                 150                 155                 160

Cys Pro Glu Gly Ile Ile Leu Leu Leu Val Gln Ala Ile Leu Gly Ser
                165                 170                 175

Ile Val Asn Ala Phe Met Val Gly Cys Met Phe Val Lys Ile Ser Gln
            180                 185                 190

Pro Lys Lys Arg Ala Glu Thr Leu Met Phe Ser Asn Asn Ala Val Ile
        195                 200                 205

Ser Met Arg Asp Glu Lys Leu Cys Leu Met Phe Arg Val Gly Asp Leu
210                 215                 220

Arg Asn Ser His Ile Val Glu Ala Ser Ile Arg Ala Lys Leu Ile Lys
225                 230                 235                 240

Ser Arg Gln Thr Lys Glu Gly Glu Phe Ile Pro Leu Asn Gln Thr Asp
                245                 250                 255

Ile Asn Val Gly Phe Asp Thr Gly Asp Asp Arg Leu Phe Leu Val Ser
            260                 265                 270

Pro Leu Ile Ile Ser His Glu Ile Asn Gln Lys Ser Pro Phe Trp Glu
        275                 280                 285

Met Ser Gln Ala Gln Leu His Gln Glu Glu Phe Glu Val Val Val Ile
    290                 295                 300

Leu Glu Gly Met Val Glu Ala Thr Gly Met Thr Cys Gln Ala Arg Ser
305                 310                 315                 320

Ser Tyr Met Asp Thr Glu Val Leu Trp Gly His Arg Phe Thr Pro Val
                325                 330                 335

Leu Thr Leu Glu Lys Gly Phe Tyr Glu Val Asp Tyr Asn Thr Phe His
            340                 345                 350

Asp Thr Tyr Glu Thr Asn Thr Pro Ser Cys Cys Ala Lys Glu Leu Ala
        355                 360                 365

Glu Met Lys Arg Glu Gly Arg Leu Leu Gln Tyr Leu Pro Ser Pro Pro
    370                 375                 380

Leu Leu Gly Gly Cys Ala Glu Ala Gly Leu Asp Ala Glu Ala Glu Gln
385                 390                 395                 400

Asn Glu Glu Asp Glu Pro Lys Gly Leu Gly Gly Ser Arg Glu Ala Arg
                405                 410                 415

Gly Ser Val

<210> SEQ ID NO 22
<211> LENGTH: 379
<212> TYPE: PRT
<213> ORGANISM: Homo sapiens

<400> SEQUENCE: 22

Met Thr Ser Val Ala Lys Val Tyr Tyr Ser Gln Thr Thr Gln Thr Glu
1               5                   10                  15

Ser Arg Pro Leu Met Gly Pro Gly Ile Arg Arg Arg Val Leu Thr
                20                  25                  30

Lys Asp Gly Arg Ser Asn Val Arg Met Glu His Ile Ala Asp Lys Arg
            35                  40                  45

Phe Leu Tyr Leu Lys Asp Leu Trp Thr Thr Phe Ile Asp Met Gln Trp
    50                  55                  60

Arg Tyr Lys Leu Leu Phe Ser Ala Thr Phe Ala Gly Thr Trp Phe
65                  70                  75                  80

Leu Phe Gly Val Val Trp Tyr Leu Val Ala Val Ala His Gly Asp Leu
                85                  90                  95

Leu Glu Leu Asp Pro Pro Ala Asn His Thr Pro Cys Val Val Gln Val
            100                 105                 110

His Thr Leu Thr Gly Ala Phe Leu Phe Ser Leu Glu Ser Gln Thr Thr
        115                 120                 125

Ile Gly Tyr Gly Phe Arg Tyr Ile Ser Glu Glu Cys Pro Leu Ala Ile
    130                 135                 140

Val Leu Leu Ile Ala Gln Leu Val Leu Thr Thr Ile Leu Glu Ile Phe
145                 150                 155                 160

Ile Thr Gly Thr Phe Leu Ala Lys Ile Ala Arg Pro Lys Lys Arg Ala
                165                 170                 175

Glu Thr Ile Arg Phe Ser Gln His Ala Val Val Ala Ser His Asn Gly
            180                 185                 190

Lys Pro Cys Leu Met Ile Arg Val Ala Asn Met Arg Lys Ser Leu Leu
        195                 200                 205

Ile Gly Cys Gln Val Thr Gly Lys Leu Leu Gln Thr His Gln Thr Lys
    210                 215                 220

Glu Gly Glu Asn Ile Arg Leu Asn Gln Val Asn Val Thr Phe Gln Val
225                 230                 235                 240

Asp Thr Ala Ser Asp Ser Pro Phe Leu Ile Leu Pro Leu Thr Phe Tyr
                245                 250                 255

His Val Val Asp Glu Thr Ser Pro Leu Lys Asp Leu Pro Leu Arg Ser
            260                 265                 270

Gly Glu Gly Asp Phe Glu Leu Val Leu Ile Leu Ser Gly Thr Val Glu
        275                 280                 285

Ser Thr Ser Ala Thr Cys Gln Val Arg Thr Ser Tyr Leu Pro Glu Glu
    290                 295                 300

Ile Leu Trp Gly Tyr Glu Phe Thr Pro Ala Ile Ser Leu Ser Ala Ser
305                 310                 315                 320

```
Gly Lys Tyr Ile Ala Asp Phe Ser Leu Phe Asp Gln Val Val Lys Val
                325                 330                 335

Ala Ser Pro Ser Gly Leu Arg Asp Ser Thr Val Arg Tyr Gly Asp Pro
            340                 345                 350

Glu Lys Leu Lys Leu Glu Glu Ser Leu Arg Glu Gln Ala Glu Lys Glu
            355                 360                 365

Gly Ser Ala Leu Ser Val Arg Ile Ser Asn Val
        370                 375

<210> SEQ ID NO 23
<211> LENGTH: 375
<212> TYPE: PRT
<213> ORGANISM: Homo sapiens

<400> SEQUENCE: 23

Met Asp Ala Ile His Ile Gly Met Ser Ser Thr Pro Leu Val Lys His
1               5                   10                  15

Thr Ala Gly Ala Gly Leu Lys Ala Asn Arg Pro Arg Val Met Ser Lys
            20                  25                  30

Ser Gly His Ser Asn Val Arg Ile Asp Lys Val Asp Gly Ile Tyr Leu
        35                  40                  45

Leu Tyr Leu Gln Asp Leu Trp Thr Thr Val Ile Asp Met Lys Trp Arg
    50                  55                  60

Tyr Lys Leu Thr Leu Phe Ala Ala Thr Phe Val Met Thr Trp Phe Leu
65                  70                  75                  80

Phe Gly Val Ile Tyr Tyr Ala Ile Ala Phe Ile His Gly Asp Leu Glu
                85                  90                  95

Pro Gly Glu Pro Ile Ser Asn His Thr Pro Cys Ile Met Lys Val Asp
            100                 105                 110

Ser Leu Thr Gly Ala Phe Leu Phe Ser Leu Glu Ser Gln Thr Thr Ile
        115                 120                 125

Gly Tyr Gly Val Arg Ser Ile Thr Glu Glu Cys Pro His Ala Ile Phe
    130                 135                 140

Leu Leu Val Ala Gln Leu Val Ile Thr Thr Leu Ile Glu Ile Phe Ile
145                 150                 155                 160

Thr Gly Thr Phe Leu Ala Lys Ile Ala Arg Pro Lys Lys Arg Ala Glu
                165                 170                 175

Thr Ile Lys Phe Ser His Cys Ala Val Ile Thr Lys Gln Asn Gly Lys
            180                 185                 190

Leu Cys Leu Val Ile Gln Val Ala Asn Met Arg Lys Ser Leu Leu Ile
        195                 200                 205

Gln Cys Gln Leu Ser Gly Lys Leu Leu Gln Thr His Val Thr Lys Glu
    210                 215                 220

Gly Glu Arg Ile Leu Leu Asn Gln Ala Thr Val Lys Phe His Val Asp
225                 230                 235                 240

Ser Ser Ser Glu Ser Pro Phe Leu Ile Leu Pro Met Thr Phe Tyr His
                245                 250                 255

Val Leu Asp Glu Thr Ser Pro Leu Arg Asp Leu Thr Pro Gln Asn Leu
            260                 265                 270

Lys Glu Lys Glu Phe Glu Leu Val Val Leu Leu Asn Ala Thr Val Glu
        275                 280                 285

Ser Thr Ser Ala Val Cys Gln Ser Arg Thr Ser Tyr Ile Pro Glu Glu
    290                 295                 300

Ile Tyr Trp Gly Phe Glu Phe Val Pro Val Val Ser Leu Ser Lys Asn
```

```
                305                 310                 315                 320
Gly Lys Tyr Val Ala Asp Phe Ser Gln Phe Glu Gln Ile Arg Lys Ser
                    325                 330                 335

Pro Asp Cys Thr Phe Tyr Cys Ala Asp Ser Glu Lys Gln Gln Leu Glu
                340                 345                 350

Glu Lys Tyr Arg Gln Glu Asp Gln Arg Glu Arg Glu Leu Arg Thr Leu
            355                 360                 365

Leu Leu Gln Gln Ser Asn Val
        370                 375

<210> SEQ ID NO 24
<211> LENGTH: 418
<212> TYPE: PRT
<213> ORGANISM: Homo sapiens

<400> SEQUENCE: 24

Met Ser Tyr Tyr Gly Ser Ser Tyr His Ile Ile Asn Ala Asp Ala Lys
1               5                   10                  15

Tyr Pro Gly Tyr Pro Pro Glu His Ile Ala Glu Lys Arg Arg Ala
            20                  25                  30

Arg Arg Arg Leu Leu His Lys Asp Gly Ser Cys Asn Val Tyr Phe Lys
        35                  40                  45

His Ile Phe Gly Glu Trp Gly Ser Tyr Val Val Asp Ile Phe Thr Thr
    50                  55                  60

Leu Val Asp Thr Lys Trp Arg His Met Phe Val Ile Phe Ser Leu Ser
65                  70                  75                  80

Tyr Ile Leu Ser Trp Leu Ile Phe Gly Ser Val Phe Trp Leu Ile Ala
                85                  90                  95

Phe His His Gly Asp Leu Leu Asn Asp Pro Asp Ile Thr Pro Cys Val
            100                 105                 110

Asp Asn Val His Ser Phe Thr Gly Ala Phe Leu Phe Ser Leu Glu Thr
        115                 120                 125

Gln Thr Thr Ile Gly Tyr Gly Tyr Arg Cys Val Thr Glu Glu Cys Ser
    130                 135                 140

Val Ala Val Leu Met Val Ile Leu Gln Ser Ile Leu Ser Cys Ile Ile
145                 150                 155                 160

Asn Thr Phe Ile Ile Gly Ala Ala Leu Ala Lys Met Ala Thr Ala Arg
                165                 170                 175

Lys Arg Ala Gln Thr Ile Arg Phe Ser Tyr Phe Ala Leu Ile Gly Met
            180                 185                 190

Arg Asp Gly Lys Leu Cys Leu Met Trp Arg Ile Gly Asp Phe Arg Pro
        195                 200                 205

Asn His Val Val Glu Gly Thr Val Arg Ala Gln Leu Leu Arg Tyr Thr
    210                 215                 220

Glu Asp Ser Glu Gly Arg Met Thr Met Ala Phe Lys Asp Leu Lys Leu
225                 230                 235                 240

Val Asn Asp Gln Ile Ile Leu Val Thr Pro Val Thr Ile Val His Glu
                245                 250                 255

Ile Asp His Glu Ser Pro Leu Tyr Ala Leu Asp Arg Lys Ala Val Ala
            260                 265                 270

Lys Asp Asn Phe Glu Ile Leu Val Thr Phe Ile Tyr Thr Gly Asp Ser
        275                 280                 285

Thr Gly Thr Ser His Gln Ser Arg Ser Ser Tyr Val Pro Arg Glu Ile
    290                 295                 300
```

```
Leu Trp Gly His Arg Phe Asn Asp Val Leu Glu Val Lys Arg Lys Tyr
305                 310                 315                 320

Tyr Lys Val Asn Cys Leu Gln Phe Glu Gly Ser Val Glu Val Tyr Ala
            325                 330                 335

Pro Phe Cys Ser Ala Lys Gln Leu Asp Trp Lys Asp Gln Gln Leu His
            340                 345                 350

Ile Glu Lys Ala Pro Pro Val Arg Glu Ser Cys Thr Ser Asp Thr Lys
        355                 360                 365

Ala Arg Arg Ser Phe Ser Ala Val Ala Ile Val Ser Ser Cys Glu
370                 375                 380

Asn Pro Glu Glu Thr Thr Thr Ser Ala Thr His Glu Tyr Arg Glu Thr
385                 390                 395                 400

Pro Tyr Gln Lys Ala Leu Leu Thr Leu Asn Arg Ile Ser Val Glu Ser
                405                 410                 415

Gln Met
```

```
<210> SEQ ID NO 25
<211> LENGTH: 424
<212> TYPE: PRT
<213> ORGANISM: Homo sapiens

<400> SEQUENCE: 25

Met Leu Ala Arg Lys Ser Ile Ile Pro Glu Glu Tyr Val Leu Ala Arg
1               5                   10                  15

Ile Ala Ala Glu Asn Leu Arg Lys Pro Arg Ile Arg Asp Arg Leu Pro
            20                  25                  30

Lys Ala Arg Phe Ile Ala Lys Ser Gly Ala Cys Asn Leu Ala His Lys
        35                  40                  45

Asn Ile Arg Glu Gln Gly Arg Phe Leu Gln Asp Ile Phe Thr Thr Leu
    50                  55                  60

Val Asp Leu Lys Trp Arg His Thr Leu Val Ile Phe Thr Met Ser Phe
65                  70                  75                  80

Leu Cys Ser Trp Leu Leu Phe Ala Ile Met Trp Trp Leu Val Ala Phe
                85                  90                  95

Ala His Gly Asp Ile Tyr Ala Tyr Met Glu Lys Ser Gly Met Glu Lys
            100                 105                 110

Ser Gly Leu Glu Ser Thr Val Cys Val Thr Asn Val Arg Ser Phe Thr
        115                 120                 125

Ser Ala Phe Leu Phe Ser Ile Glu Val Gln Val Thr Ile Gly Phe Gly
    130                 135                 140

Gly Arg Met Met Thr Glu Glu Cys Pro Leu Ala Ile Thr Val Leu Ile
145                 150                 155                 160

Leu Gln Asn Ile Val Gly Leu Ile Ile Asn Ala Val Met Leu Gly Cys
                165                 170                 175

Ile Phe Met Lys Thr Ala Gln Ala His Arg Arg Ala Glu Thr Leu Ile
            180                 185                 190

Phe Ser Arg His Ala Val Ile Ala Val Arg Asn Gly Lys Leu Cys Phe
        195                 200                 205

Met Phe Arg Val Gly Asp Leu Arg Lys Ser Met Ile Ile Ser Ala Ser
    210                 215                 220

Val Arg Ile Gln Val Val Lys Lys Thr Thr Thr Pro Glu Gly Glu Val
225                 230                 235                 240

Val Pro Ile His Gln Leu Asp Ile Pro Val Asp Asn Pro Ile Glu Ser
                245                 250                 255
```

```
Asn Asn Ile Phe Leu Val Ala Pro Leu Ile Ile Cys His Val Ile Asp
                260                 265                 270

Lys Arg Ser Pro Leu Tyr Asp Ile Ser Ala Thr Asp Leu Ala Asn Gln
            275                 280                 285

Asp Leu Glu Val Ile Val Ile Leu Glu Gly Val Val Glu Thr Thr Gly
        290                 295                 300

Ile Thr Thr Gln Ala Arg Thr Ser Tyr Ile Ala Glu Glu Ile Gln Trp
305                 310                 315                 320

Gly His Arg Phe Val Ser Ile Val Thr Glu Glu Gly Val Tyr Ser
                325                 330                 335

Val Asp Tyr Ser Lys Phe Gly Asn Thr Val Lys Val Ala Ala Pro Arg
            340                 345                 350

Cys Ser Ala Arg Glu Leu Asp Glu Lys Pro Ser Ile Leu Ile Gln Thr
        355                 360                 365

Leu Gln Lys Ser Glu Leu Ser His Gln Asn Ser Leu Arg Lys Arg Asn
    370                 375                 380

Ser Met Arg Arg Asn Asn Ser Met Arg Arg Asn Asn Ser Ile Arg Arg
385                 390                 395                 400

Asn Asn Ser Ser Leu Met Val Pro Lys Val Gln Phe Met Thr Pro Glu
                405                 410                 415

Gly Asn Gln Asn Thr Ser Glu Ser
            420

<210> SEQ ID NO 26
<211> LENGTH: 390
<212> TYPE: PRT
<213> ORGANISM: Homo sapiens

<400> SEQUENCE: 26

Met Leu Ser Arg Lys Gly Ile Ile Pro Glu Glu Tyr Val Leu Thr Arg
1               5                   10                  15

Leu Ala Glu Asp Pro Ala Lys Pro Arg Tyr Arg Ala Arg Gln Arg Arg
            20                  25                  30

Ala Arg Phe Val Ser Lys Lys Gly Asn Cys Asn Val Ala His Lys Asn
        35                  40                  45

Ile Arg Glu Gln Gly Arg Phe Leu Gln Asp Val Phe Thr Thr Leu Val
    50                  55                  60

Asp Leu Lys Trp Pro His Thr Leu Leu Ile Phe Thr Met Ser Phe Leu
65                  70                  75                  80

Cys Ser Trp Leu Leu Phe Ala Met Ala Trp Trp Leu Ile Ala Phe Ala
                85                  90                  95

His Gly Asp Leu Ala Pro Ser Glu Gly Thr Ala Glu Pro Cys Val Thr
            100                 105                 110

Ser Ile His Ser Phe Ser Ser Ala Phe Leu Phe Ser Ile Glu Val Gln
        115                 120                 125

Val Thr Ile Gly Phe Gly Gly Arg Met Val Thr Glu Glu Cys Pro Leu
    130                 135                 140

Ala Ile Leu Ile Leu Ile Val Gln Asn Ile Val Gly Leu Met Ile Asn
145                 150                 155                 160

Ala Ile Met Leu Gly Cys Ile Phe Met Lys Thr Ala Gln Ala His Arg
                165                 170                 175

Arg Ala Glu Thr Leu Ile Phe Ser Lys His Ala Val Ile Ala Leu Arg
            180                 185                 190

His Gly Arg Leu Cys Phe Met Leu Arg Val Gly Asp Leu Arg Lys Ser
        195                 200                 205
```

Met Ile Ile Ser Ala Thr Ile His Met Gln Val Val Arg Lys Thr Thr
210                 215                 220

Ser Pro Glu Gly Glu Val Pro Leu His Gln Val Asp Ile Pro Met
225                 230                 235                 240

Glu Asn Gly Val Gly Gly Asn Ser Ile Phe Leu Val Ala Pro Leu Ile
                245                 250                 255

Ile Tyr His Val Ile Asp Ala Asn Ser Pro Leu Tyr Asp Leu Ala Pro
                260                 265                 270

Ser Asp Leu His His His Gln Asp Leu Glu Ile Ile Val Ile Leu Glu
                275                 280                 285

Gly Val Val Glu Thr Thr Gly Ile Thr Thr Gln Ala Arg Thr Ser Tyr
290                 295                 300

Leu Ala Asp Glu Ile Leu Trp Gly Gln Arg Phe Val Pro Ile Val Ala
305                 310                 315                 320

Glu Glu Asp Gly Arg Tyr Ser Val Asp Tyr Ser Lys Phe Gly Asn Thr
                325                 330                 335

Val Lys Val Pro Thr Pro Leu Cys Thr Ala Arg Gln Leu Asp Glu Asp
                340                 345                 350

His Ser Leu Leu Glu Ala Leu Thr Leu Ala Ser Ala Arg Gly Pro Leu
                355                 360                 365

Arg Lys Arg Ser Val Pro Met Ala Lys Ala Lys Pro Lys Phe Ser Ile
370                 375                 380

Ser Pro Asp Ser Leu Ser
385                 390

<210> SEQ ID NO 27
<211> LENGTH: 360
<212> TYPE: PRT
<213> ORGANISM: Homo sapiens

<400> SEQUENCE: 27

Met Asp Ser Ser Asn Cys Lys Val Ile Ala Pro Leu Leu Ser Gln Arg
1               5                   10                  15

Tyr Arg Arg Met Val Thr Lys Asp Gly His Ser Thr Leu Gln Met Asp
                20                  25                  30

Gly Ala Gln Arg Gly Leu Ala Tyr Leu Arg Asp Ala Trp Gly Ile Leu
            35                  40                  45

Met Asp Met Arg Trp Arg Trp Met Met Leu Val Phe Ser Ala Ser Phe
50                  55                  60

Val Val His Trp Leu Val Phe Ala Val Leu Trp Tyr Val Leu Ala Glu
65                  70                  75                  80

Met Asn Gly Asp Leu Glu Leu Asp His Asp Ala Pro Pro Glu Asn His
                85                  90                  95

Thr Ile Cys Val Lys Tyr Ile Thr Ser Phe Thr Ala Ala Phe Ser Phe
                100                 105                 110

Ser Leu Glu Thr Gln Leu Thr Ile Gly Tyr Gly Thr Met Phe Pro Ser
            115                 120                 125

Gly Asp Cys Pro Ser Ala Ile Ala Leu Leu Ala Ile Gln Met Leu Leu
130                 135                 140

Gly Leu Met Leu Glu Ala Phe Ile Thr Gly Ala Phe Val Ala Lys Ile
145                 150                 155                 160

Ala Arg Pro Lys Asn Arg Ala Phe Ser Ile Arg Phe Thr Asp Thr Ala
                165                 170                 175

Val Val Ala His Met Asp Gly Lys Pro Asn Leu Ile Phe Gln Val Ala

```
            180             185             190
Asn Thr Arg Pro Ser Pro Leu Thr Ser Val Arg Val Ser Ala Val Leu
        195                 200                 205
Tyr Gln Glu Arg Glu Asn Gly Lys Leu Tyr Gln Thr Ser Val Asp Phe
        210                 215                 220
His Leu Asp Gly Ile Ser Ser Asp Glu Cys Pro Phe Phe Ile Phe Pro
225                 230                 235                 240
Leu Thr Tyr Tyr His Ser Ile Thr Pro Ser Ser Pro Leu Ala Thr Leu
            245                 250                 255
Leu Gln His Glu Asn Pro Ser His Phe Glu Leu Val Val Phe Leu Ser
        260                 265                 270
Ala Met Gln Glu Gly Thr Gly Glu Ile Cys Gln Arg Arg Thr Ser Tyr
        275                 280                 285
Leu Pro Ser Glu Ile Met Leu His His Cys Phe Ala Ser Leu Leu Thr
        290                 295                 300
Arg Gly Ser Lys Gly Glu Tyr Gln Ile Lys Met Glu Asn Phe Asp Lys
305                 310                 315                 320
Thr Val Pro Glu Phe Pro Thr Pro Leu Val Ser Lys Ser Pro Asn Arg
                325                 330                 335
Thr Asp Leu Asp Ile His Ile Asn Gly Gln Ser Ile Asp Asn Phe Gln
                340                 345                 350
Ile Ser Glu Thr Gly Leu Thr Glu
            355                 360

<210> SEQ ID NO 28
<211> LENGTH: 427
<212> TYPE: PRT
<213> ORGANISM: Gallus gallus

<400> SEQUENCE: 28

Met Gly Ser Val Arg Thr Asn Arg Tyr Ser Ile Val Ser Ser Glu Glu
1               5                   10                  15
Asp Gly Met Lys Leu Ala Thr Met Ala Val Ala Asn Gly Phe Gly Asn
            20                  25                  30
Gly Lys Ser Lys Val His Thr Arg Gln Gln Cys Arg Ser Arg Phe Val
        35                  40                  45
Lys Lys Asp Gly His Cys Asn Val Gln Phe Ile Asn Val Gly Glu Lys
    50                  55                  60
Gly Gln Arg Tyr Leu Ala Asp Ile Phe Thr Thr Cys Val Asp Ile Arg
65                  70                  75                  80
Trp Arg Trp Met Leu Val Ile Phe Cys Leu Thr Phe Ile Leu Ser Trp
                85                  90                  95
Leu Phe Phe Gly Cys Val Phe Trp Leu Ile Ala Leu Leu His Gly Asp
            100                 105                 110
Leu Glu Asn Gln Glu Asn Asn Lys Pro Cys Val Ser Gln Val Ser Ser
        115                 120                 125
Phe Thr Ala Ala Phe Leu Phe Ser Ile Glu Thr Gln Thr Thr Ile Gly
    130                 135                 140
Tyr Gly Phe Arg Cys Val Thr Asp Glu Cys Pro Ile Ala Val Phe Met
145                 150                 155                 160
Val Val Phe Gln Ser Ile Val Gly Cys Ile Ile Asp Ala Phe Ile Ile
                165                 170                 175
Gly Ala Val Met Ala Lys Met Ala Lys Pro Lys Lys Arg Asn Glu Thr
            180                 185                 190
```

Leu Val Phe Ser His Asn Ala Val Ala Met Arg Asp Gly Lys Leu
        195                 200                 205

Cys Leu Met Trp Arg Val Gly Asn Leu Arg Lys Ser His Leu Val Glu
210                 215                 220

Ala His Val Arg Ala Gln Leu Leu Lys Ser Arg Ile Thr Ser Glu Gly
225                 230                 235                 240

Glu Tyr Ile Pro Leu Asp Glu Ile Asp Ile Asn Val Gly Phe Asp Ser
                245                 250                 255

Gly Ile Asp Arg Ile Phe Leu Val Ser Pro Ile Thr Ile Val His Glu
                260                 265                 270

Ile Asp Glu Asp Ser Pro Leu Tyr Asp Leu Ser Lys Gln Asp Met Asp
        275                 280                 285

Asn Ala Asp Phe Glu Ile Val Val Ile Leu Glu Gly Met Val Glu Ala
        290                 295                 300

Thr Ala Met Thr Thr Gln Cys Arg Ser Ser Tyr Leu Ala Asn Glu Ile
305                 310                 315                 320

Leu Trp Gly His Arg Tyr Glu Pro Val Leu Phe Glu Glu Lys Asn Tyr
                325                 330                 335

Tyr Lys Val Asp Tyr Ser Arg Phe His Lys Thr Tyr Glu Val Pro Asn
                340                 345                 350

Thr Pro Ile Cys Ser Ala Arg Asp Leu Ala Glu Lys Lys Tyr Ile Leu
        355                 360                 365

Ser Asn Ala Asn Ser Phe Cys Tyr Glu Asn Glu Val Ala Leu Thr Ser
        370                 375                 380

Lys Glu Glu Asp Glu Ile Asp Thr Gly Val Pro Glu Ser Thr Ser Thr
385                 390                 395                 400

Asp Thr His Pro Asp Met Asp His His Asn Gln Ala Gly Val Pro Leu
                405                 410                 415

Glu Pro Arg Pro Leu Arg Arg Glu Ser Glu Ile
                420                 425

<210> SEQ ID NO 29
<211> LENGTH: 429
<212> TYPE: PRT
<213> ORGANISM: Gallus gallus

<400> SEQUENCE: 29

Met Thr Ala Gly Arg Val Asn Pro Tyr Ser Ile Val Ser Ser Glu Glu
1               5                   10                  15

Asp Gly Leu Arg Leu Thr Thr Met Pro Gly Ile Asn Gly Phe Gly Asn
                20                  25                  30

Gly Lys Ile His Thr Arg Arg Lys Cys Arg Asn Arg Phe Val Lys Lys
            35                  40                  45

Asn Gly Gln Cys Asn Val Glu Phe Thr Asn Met Asp Asp Lys Pro Gln
        50                  55                  60

Arg Tyr Ile Ala Asp Met Phe Thr Thr Cys Val Asp Ile Arg Trp Arg
65                  70                  75                  80

Tyr Met Leu Leu Leu Phe Ser Leu Ala Phe Leu Val Ser Trp Leu Leu
                85                  90                  95

Phe Gly Leu Ile Phe Trp Leu Ile Ala Leu Ile His Gly Asp Leu Glu
                100                 105                 110

Asn Pro Gly Gly Asp Asp Thr Phe Lys Pro Cys Val Leu Gln Val Asn
            115                 120                 125

Gly Phe Val Ala Ala Phe Leu Phe Ser Ile Glu Thr Gln Thr Thr Ile
        130                 135                 140

Gly Tyr Gly Phe Arg Cys Val Thr Glu Glu Cys Pro Leu Ala Val Phe
145                 150                 155                 160

Met Val Val Val Gln Ser Ile Val Gly Cys Ile Ile Asp Ser Phe Met
            165                 170                 175

Ile Gly Ala Ile Met Ala Lys Met Ala Arg Pro Lys Lys Arg Ala Gln
        180                 185                 190

Thr Leu Leu Phe Ser His Asn Ala Val Val Ala Met Arg Asp Gly Lys
    195                 200                 205

Leu Cys Leu Met Trp Arg Val Gly Asn Leu Arg Lys Ser His Ile Val
210                 215                 220

Glu Ala His Val Arg Ala Gln Leu Ile Lys Pro Arg Ile Thr Glu Glu
225                 230                 235                 240

Gly Glu Tyr Ile Pro Leu Asp Gln Ile Asp Ile Asp Val Gly Phe Asp
            245                 250                 255

Lys Gly Leu Asp Arg Ile Phe Leu Val Ser Pro Ile Thr Ile Leu His
        260                 265                 270

Glu Ile Asn Glu Asp Ser Pro Leu Phe Gly Ile Ser Arg Gln Asp Leu
    275                 280                 285

Glu Thr Asp Asp Phe Glu Ile Val Val Ile Leu Glu Gly Met Val Glu
290                 295                 300

Ala Thr Ala Met Thr Thr Gln Ala Arg Ser Ser Tyr Leu Ala Ser Glu
305                 310                 315                 320

Ile Leu Trp Gly His Arg Phe Glu Pro Val Leu Phe Glu Lys Asn
            325                 330                 335

Gln Tyr Lys Val Asp Tyr Ser His Phe His Lys Thr Tyr Glu Val Pro
        340                 345                 350

Ser Thr Pro Arg Cys Ser Ala Lys Asp Leu Val Glu Asn Lys Phe Leu
    355                 360                 365

Leu Pro Ser Thr Asn Ser Phe Cys Tyr Glu Asn Glu Leu Ala Phe Met
370                 375                 380

Ser Arg Asp Glu Asp Glu Glu Asp Asp Ser Arg Gly Leu Asp Asp
385                 390                 395                 400

Leu Ser Pro Asp Asn Arg His Glu Phe Asp Arg Leu Gln Ala Thr Ile
            405                 410                 415

Ala Leu Asp Gln Arg Ser Tyr Arg Arg Glu Ser Glu Ile
        420                 425

<210> SEQ ID NO 30
<211> LENGTH: 1176
<212> TYPE: DNA
<213> ORGANISM: Homo sapiens

<400> SEQUENCE: 30
atgaatgctt ccagtcggaa tgtgtttgac acgttgatca gggtgttgac agaaagtatg      60
ttcaaacatc ttcggaaatg ggtcgtcact cgcttttttg ggcattctcg gcaaagagca     120
aggctagtct ccaaagatgg aaggtgcaac atagaatttg gcaatgtgga ggcacagtca     180
aggtttatat tctttgtgga catctggaca acggtacttg acctcaagtg gagatacaaa     240
atgaccattt tcatcacagc cttcttgggg agttggtttt tctttggtct cctgtggtat     300
gcagtagcgt acattcacaa agacctcccg gaattccatc cttctgccaa tcacactccc     360
tgtgtggaga atattaatgg cttgacctca gcttttctgt ttctctgga gactcaagtg     420 accattgatg atggattcag gtgtgtgaca gaacagtgtg ccactgccat ttttctgctt     480

-continued

| | |
|---|---|
| atctttcagt ctatacttgg agttataatc aattctttca tgtgtggggc catcttagcc | 540 |
| aagatctcca ggcccaaaaa acgtgccaag accattacgt tcagcaagaa cgcagtgatc | 600 |
| agcaaacggg gagggaagct tgcctcctaa tccgagtgg ctaatctcag gaagagcctt | 660 |
| cttattggca gtcacattta tggaaagctt ctgaagacca cagtcactcc tgaaggagag | 720 |
| accattattt tggaccagat caatatcaac tttgtagttg acgctgggaa tgaaaattta | 780 |
| ttcttcatct ccccattgac aatttaccat gtcattgatc acaacagccc tttcttccac | 840 |
| atggcagcgg agaccttct ccagcaggac tttgaattag tggtgttttt agatggcaca | 900 |
| gtggagtcca ccagtgctac ctgccaagtc cggacatcct atgtcccaga ggaggtgctt | 960 |
| tggggctacc gttttgctcc catagtatcc aagacaaagg aagggaaata ccgagtggat | 1020 |
| ttccataact ttagcaagac agtggaagtg gagaccctc actgtgccat gtgcctttat | 1080 |
| aatgagaaag atgttagagc caggatgaag agaggctatg acaaccccaa cttcatcttg | 1140 |
| tcagaagtca atgaaacaga tgacaccaaa atgtaa | 1176 |

<210> SEQ ID NO 31
<211> LENGTH: 1282
<212> TYPE: DNA
<213> ORGANISM: Homo sapiens

<400> SEQUENCE: 31

| | |
|---|---|
| cttttctgat cccagctccg ggtttaagag tcctggcacg gcccgtcgca cagctctgct | 60 |
| cctaactcct gcccgccccg tccgtccatc tgtcccgctg cccgcggcc catccaaggg | 120 |
| gccactccac ctcggaccca agatgacgtc agttgccaag gtgtattaca gtcagaccac | 180 |
| tcagacagaa agccggcccc taatgggccc agggatacga cggcggagag tcctgacaaa | 240 |
| agatggtcgc agcaacgtga gaatggagca cattgccgac aagcgcttcc tctacctcaa | 300 |
| ggacctgtgg acaaccttca ttgacatgca gtggcgctac aagcttctgc tcttctctgc | 360 |
| gacctttgca ggcacatggt tcctctttgt cgtggtgtgg tatctggtag ctgtggcaca | 420 |
| tggggacctg ctggagctgg accccccggc caaccacacc cctgtgtgg tacaggtgca | 480 |
| cacactcact ggagccttcc tcttctccct tgaatcccaa accaccattg gctatggctt | 540 |
| ccgctacatc agtgaggaat gtccactagc cattgtgctt cttattgccc agctggtgct | 600 |
| caccaccatc ctgaaatct tcatcacagg taccttcctg gcgaagattg cccggcccaa | 660 |
| gaagcgggct gagaccattc gtttcagcca gcatgcagtt gtggcctccc acaatggcaa | 720 |
| gccctgcctc atgatccgag ttgccaatat gcgcaaaagc ctcctcattg gctgccaggt | 780 |
| gacaggaaaa ctgcttcaga cccaccaaac caaggaaggg gagaacatcc ggctcaacca | 840 |
| ggtcaatgtg acttttccaag tagacacagc ctctgacagc cccttcctta ttctaccct | 900 |
| taccttctat catgtggtag atgagaccag tcccttgaaa gatctccctc ttcgcagtgg | 960 |
| tgagggtgac tttgagctgg tgctgatcct aagtgggaca gtggagtcca ccagtgccac | 1020 |
| ctgtcaggtg cgcacttcct acctgccaga ggagatcctt tggggctacg agttcacacc | 1080 |
| tgccatctca ctgtcagcca gtggtaaata catagctgac tttagccttt tgaccaagt | 1140 |
| tgtgaaagtg gcctctccta gtggcctccg tgacagcact gtacgctacg agaccctga | 1200 |
| aaagctcaag ttggaggagt cattaaggga gcaagctgag aaggagggca gtgcccttag | 1260 |
| tgtgcgcatc agcaatgtct ga | 1282 |

<210> SEQ ID NO 32
<211> LENGTH: 1326

```
<212> TYPE: DNA
<213> ORGANISM: Homo sapiens

<400> SEQUENCE: 32
atgggcagtg tgcgaaccaa ccgctacagc atcgtctctt cagaagaaga cggtatgaag      60
ttggccacca tggcagttgc aaatggcttt gggaacggga agagtaaagt ccacacccga     120
caacagtgca ggagccgctt tgtgaagaaa gatggccact gtaatgttca gttcatcaat     180
gtgggtgaga aggggcaacg gtacctcgca gacatcttca ccacgtgtgt ggacattcgc     240
tggcggtgga tgctggttat cttctgcctg gctttcgtcc tgtcatggct gttttttggc     300
tgtgtgtttt ggttgatagc tctgctccat ggggacctgg atgcatccaa agagggcaaa     360
gcttgtgtgt ccgaggtcaa cagcttcacg gctgccttcc tcttctccat tgagacccag     420
acaaccatag gctatggttt cagatgtgtc acggatgaat gcccaattgc tgttttcatg     480
gtggtgttcc agtcaatcgt gggctgcatc atcgatgctt tcatcattgg cgcagtcatg     540
gccaagatgg caaagccaaa gaagagaaac gagactcttg tcttcagtca aatgccgtg      600
attgccatga gagacggcaa gctgtgtttg atgtggcgag tgggcaatct tcggaaaagc     660
cacttggtgg aagctcatgt tcgagcacag ctcctcaaat ccagaattac ttctgaaggg     720
gagtatatcc ctctggatca aatagacatc aatgttgggt ttgacagtgg aatcgatcgt     780
atatttctgg tgtccccaat cactatagtc catgaaatag atgaagacag tcctttatat     840
gatttgagta acaggacat tgacaacgca gactttgaaa tcgtggtcat actggaaggc      900
atggtggaag ccactgccat gacgacacag tgccgtagct cttatctagc aaatgaaatc     960
ctgtggggcc accgctatga gcctgtgctc tttgaagaga agcactacta caaagtggac    1020
tattccaggt tccacaaaac ttacgaagtc cccaacactc cccttgtag tgccagagac      1080
ttagcagaaa agaaatatat cctctcaaat gcaaattcat tttgctatga aaatgaagtt    1140
gccctcacaa gcaagagga gacgacagt gaaaatggag ttccagaaag cactagtacg       1200
gacacgcccc ctgacataga ccttcacaac caggcaagtg tacctctaga gcccaggccc    1260
ttacggcgag agtcggagat atgagtcctg gagcagcggc cctacagacg ggagtcagag    1320
atctga                                                               1326

<210> SEQ ID NO 33
<211> LENGTH: 1302
<212> TYPE: DNA
<213> ORGANISM: Homo sapiens

<400> SEQUENCE: 33
atgaccgcgg ccagccgggc caaccccctac agcatcgtgt catcggagga ggacgggctg      60
cacctggtca ccatgtcggg cgccaacggc ttcggcaacg gcaaggtgca cacgcggcgc     120
aggtgccgca accgcttcgt caagaagaat ggccagtgca acattgagtt cgccaacatg     180
gacgagaagt cacagcgcta cctggctgac atgttcacca cctgtgtgga catccgctgg     240
cggtacatgc tgctcatctt ctcgctggcc ttccttgcct cctggctgct gttcggcatc     300
atcttctggg tcatcgcggt ggcacacggt gaccttgagc cggctgaggg ccggggccgc     360
acaccctgtg tgatgcaggt gcacggcttc atggcggcct cctcttctc catcgagacg       420
cagaccacca tcggctacgg gctgcgctgt gtgacggagg agtgcccggt ggccgtcttc      480
atggtggtgg cccagtccat cgtgggctgc atcatcgact ccttcatgat tggtgccatc     540
atggccaaga tggcaaggcc caagaagcgg gcacagacgc tgctgttcag ccacaacgcc     600
```

```
gtggtggccc tgcgtgacgg caagctctgc ctcatgtggc gtgtgggtaa cctgcgcaag    660
agccacattg tggaggccca tgtgcgcgcg cagctcatca agccgcgggt caccgaggag    720
ggcgagtaca tcccgctgga ccagatcgac atcgatgtgg gcttcgacaa gggcctggac    780
cgcatctttc tggtgtcgcc catcaccatc ttgcatgaga ttgacgaggc cagcccgctc    840
ttcggcatca gccggcagga cctggagacg gacgactttg agatcgtggt catcctggaa    900
ggcatggtgg aggccacagc catgaccacc caggcccgca gctcctacct ggccaatgag    960
atcctgtggg gtcaccgctt tgagcccgtg ctcttcgagg agaagaacca gtacaagatt   1020
gactactcgc acttccacaa gacctatgag gtgccctcta cgccccgctg cagtgcgaag   1080
gatctggtag agaacaagtt cctgctgccc agcgccaact ccttctgcta cgagaacgag   1140
ctggccttcc tgagccgtga cgaggaggat gaggcggacg agaccaggga cggccgaagc   1200
cgggacggcc tcagccccca ggccaggcat gactttgaca gactccaggc tggcggcggg   1260
gtcctggagc agcggcccta cagacgggag tcagagatct ga                      1302
```

<210> SEQ ID NO 34
<211> LENGTH: 1338
<212> TYPE: DNA
<213> ORGANISM: Homo sapiens

<400> SEQUENCE: 34

```
atgcacggac acagccgcaa cggccaggcc cacgtgcccc ggcggaagcg ccgcaaccgc     60
ttcgtcaaga agaacggcca atgcaacgtg tacttcgcca acctgagcaa caagtcgcag    120
cgctacatgg cggacatctt caccacctgc gtggacacgc gctggcgcta catgctcatg    180
atcttctccg cggccttcct tgtctcctgg ctctttttcg gcctcctctt ctggtgtatc    240
gccttcttcc acgtgaccct ggaggccagc ccaggggtgc ctgcggcggg ggccccggcg    300
gcgggtggtg gcggagcagc cccggtggcc cccaagccct gcatcatgca cgtgaacggc    360
ttcctgggtg ccttcctgtt ctcggtggag acgcagacga ccatcggcta tgggttccgg    420
tgcgtgacag aggagtgccc gctggcagtc atcgctgtgg tggtccagtc catcgtgggc    480
tgcgtcatcg actccttcat gattggcacc atcatggcca gatgcgcgcg gcccaagaag    540
cgggcgcaga cgttgctgtt cagccaccac gcggtcattt cggtgcgcga cggcaagctc    600
tgcctcatgt ggcgcgtggg caacctgcgc aagagccaca ttgtggaggc ccacgtgcgg    660
gcccagctca tcaagcccta catgacccag gagggcgagt acctgccccc tggaccagcgg    720 gacctcaacg tgggctatga catcggcctg accgcatct cctggtgtc gcccatcatc      780
```

```
attgtccacg agatcgacga ggacagcccg ctttatggca tgggcaagga ggagctggag    840
tcggaggact ttgagatcgt ggtcatcctg gagggcatgg tggaggccac ggccatgacc    900
acccaggccc gcagctccta cctggccagc gagatcctgt ggggccaccg ctttgagcct    960
gtggtcttcg aggagaagag ccactacaag gtggactact cacgttttca caagacctac   1020
gaggtggccg gcacgccctg ctgctcggcc cgggagctgc aggagagtaa gatcaccgtg   1080
ctgcccgccc caccgccccc tcccagtgcc ttctgctacg agaacgagct ggcccttatg   1140
agccaggagg aagaggagat ggaggaggag gcagctgcgg cggccgcggt ggccgcaggc   1200
ctgggcctgg aggcgggttc caaggaggag gcgggcatca tccggatgct ggagttcggc   1260
agccacctgg acctggagcg catgcaggct tccctcccgc tggacaacat ctcctaccgc   1320
agggagtctg ccatctga                                                 1338
```

<210> SEQ ID NO 35
<211> LENGTH: 1311
<212> TYPE: DNA
<213> ORGANISM: Homo sapiens

<400> SEQUENCE: 35

```
atgggcctgg ccagggccct acgccgcctc agcggcgccc tggattcggg agacagccgg      60
gcgggcgatg aagaggaggc cgggcccggg ttgtgccgca acgggtgggc gccggcaccg     120
gtgcagtcac ccgtgggccg cgccgcggt cgcttcgtca agaaagacgg gcactgcaac      180
gtgcgtttcg taaacctggg tggccagggc gcgcgctacc tgagcgacct gttcaccaca     240
tgcgtggacg tgcgctggcg ctggatgtgc ctgctcttct cctgctcctt cctcgcctcc     300
tggctgctct tcggcctggc cttctggctc attgcctcgc tgcacggcga cctggccgcc     360
ccgccaccgc ccgcgccctg cttctcacac gtggccagct tcctggccgc cttcctcttc     420
gcgctggaga cgcagacgtc catcggctac ggcgtgcgca gcgtcaccga ggagtgcccg     480
gccgctgtgg ccgccgtggt gctgcagtgc attgccggct gcgtgctcga cgccttcgtc     540
gtgggtgctg tcatggccaa gatggccaaa cccaagaagc gcaacgagac gctggtcttc     600
agcgagaacg ccgtcgtggc gctgcgcgac accgcctct gcctcatgtg gcgcgtcggc      660
aacctgcgcc gcagccacct ggtcgaggcc cacgtgcgtg cccagctgct gcagccccgt     720
gtgaccccag agggtgagta catcccgctg gaccaccagg atgtggatgt gggctttgat     780
ggaggcaccg atcgtatctt cctcgtgtcc cccatcacca tcgtccatga gatcgactct     840
gccagtcctc tgtatgagct aggacgtgcc gagctggcca gggctgactt tgagctggtg     900
gtcattctcg aggggatggt tgaggccaca gccatgacca cacagtgtcg ctcgtcctac     960
ctccctggtg aactgctctg gggccatcgt tttgagccag ttctcttcca gcgtggctcc    1020
cagtatgagg tcgactatcg ccacttccat cgcacttatg aggtcccagg acaccggtc     1080
tgcagtgcta aggagctgga tgaacgggca gagcaggctt cccacagcct caagtctagt    1140
ttccccggct ctctgactgc attttgttat gagaatgaac ttgctctgag ctgctgccag    1200
gaggaagatg aggacgatga gactgaggaa gggaatgggg tggaaacaga agatggggct    1260
gctagccccc gagttctcac accaaccctg gcgctgaccc tgcctccatg a             1311
```

<210> SEQ ID NO 36
<211> LENGTH: 1506
<212> TYPE: DNA
<213> ORGANISM: Homo sapiens

<400> SEQUENCE: 36

```
atgtctgcac tccgaaggaa atttggggac gattatcagg tagtgaccac atcgtccagc      60
ggctcgggct tgcagcccca ggggccaggc caggaccctc agcagcagct tgtgcccaag     120
aagaagcggc agcggttcgt ggacaagaac ggccggtgca atgtacagca cggcaacctg     180
ggcagcgaga caagccgcta cctctcggac ctcttcacca cgctggtgga cctcaagtgg     240
cgctggaacc tcttcatctt cattctcacc tacaccgtgg cctggctttt catggcgtcc     300
atgtggtggg tgatcgccta cactcggggc gacctgaaca agcccacgt cggtaactac     360
acgccttgcg tggccaatgt ctataacttc ccttctgcct cctcttctt catcgagacg     420
gaggccacca tcggctatgg ctaccgatac atcacagaca agtgccccga gggcatcatc     480
ctcttcctct tccagtccat cctgggctcc atcgtgacg ccttcctcat cggctgcatg     540
ttcatcaaga tgtcccagcc caagaagcgc gccgagaccc tcatgttcag cgagcacgcg     600
```

```
gtgatctcca tgagggacgg aaaactcacg cttatgttcc gggtgggcaa cctgcgcaac      660
agccacatgg tctccgcgca gattcgctgc aagctgctca aatctcggca gacacctgag      720
ggtgagttcc ttccccttga ccaacttgaa ctggatgtag gttttagtac aggggcagat      780
caactttttc ttgtgtcccc cctcacaatt tgccacgtga tcgatgccaa agccccttt       840 tatgacctat cccagcgaag catgcaaact gaacagttcg agattgtcgt catcctagaa      900
ggcattgtgg aaacaactgg gatgacttgt caagctcgaa catcatatac tgaagatgaa      960
gttctttggg gtcatcgttt ttttcctgta atttccttag aagagggatt ctttaaagtt     1020
gattactccc agttccatgc aacatttgaa gtccccaccc caccttacag tgtgaaagag     1080
caggaggaaa tgcttctcat gtcgtcccct ttaatagcac cagccataac taacagcaaa     1140
gaaagacata attctgtgga atgcttagat ggactagatg atattactac aaaactacca     1200
tctaagctgc agaaaattac tggaagagaa gactttccca aaaaactctt gaggatgagt     1260
tctacaactt cagaaaaagc ctacagcttg ggagacttgc ccatgaaact tcaacgaata     1320
agttcagttc cggcaactc agaagaaaaa ctggtatcta aaccaccaa gatgttatct       1380 gatcccatga gccagtctgt ggctgatttg ccaccaaagc ttcaaaagat ggctggagga     1440
gcagctagga tggaagggaa ccttccagcc aaattaagaa aaatgaactc tgatcgcttc     1500
acataa                                                               1506

<210> SEQ ID NO 37
<211> LENGTH: 1260
<212> TYPE: DNA
<213> ORGANISM: Homo sapiens

<400> SEQUENCE: 37
atggctggcg attctaggaa tgccatgaac caggacatgg agattggagt cactccctgg       60
gaccccaaga agattccaaa acaggcccgc gattatgtcc ccattgccac agaccgtacg      120
cgcctgctgg ccgagggcaa gaagccacgc cagcgctaca tggagaagag tggcaagtgc      180
aacgtgcacc acggcaacgt ccaggagacc taccggtacc tgagtgacct cttcaccacc      240
ctggtggacc tcaagtggcg cttcaacttg ctcgtcttca ccatggttta cactgtcacc      300
tggctgttct tcggcttcat ttggtggctc attgcttata tccggggtga cctggaccat      360
gttggcgacc aagagtggat tccttgtgtt gaaaacctca gtggcttcgt gtccgctttc      420
ctgttctcca ttgagaccga aacaaccatt gggtatggct tccgagtcat cacagagaag      480
tgtccagagg ggattatact cctcttggtc caggccatcc tgggctccat cgtcaatgcc      540
ttcatggtgg ggtgcatgtt tgtcaagatc agccagccca agaagagagc ggagaccctc      600
atgttttcca acaacgcagt catctccatg cgggacgaga agctgtgcct catgttccgg      660
gtgggcgacc tccgcaactc ccacatcgtg gaggcctcca tccgggccaa gctcatcaag      720
tcccggcaga ccaaagaggg ggagttcatc ccctgaacc agacagacat caacgtgggc      780
tttgacacgg cgacgaccg cctcttcctt gtgtctcctc tgatcatctc ccatgagatc      840
aaccagaaga gccctttctg ggagatgtct caggctcagc tgcatcagga gagtttgaa      900 gttgtggtca ttctagaagg gatggtgaa gccacaggca tgacctgcca agcccggagc      960
tcctacatgg atacagaggt gctctgggc caccgattca caccagtcct caccttggaa     1020
aagggcttct atgaggtgga ctacaacacc ttccatgata cctatgagac caacacaccc     1080
agctgctgtg ccaaggagct ggcagaaatg aagagggaag gccggctcct ccagtacctc     1140
cccagccccc cactgctggg gggctgtgct gaggcagggc tggatgcaga ggctgagcag     1200
```
aatgaagaag atgagcccaa ggggctgggt gggtccaggg aggccagggg ctcggtgtga   1260

<210> SEQ ID NO 38
<211> LENGTH: 1140
<212> TYPE: DNA
<213> ORGANISM: Homo sapiens

<400> SEQUENCE: 38
atgacgtcag ttgccaaggt gtattacagt cagaccactc agacagaaag ccggcccta     60 atgggcccag ggatacgacg gcggagagtc ctgacaaaag atggtcgcag caacgtgaga   120
atggagcaca ttgccgacaa cgcgcttcctc tacctcaagg acctgtggac aaccttcatt   180
gacatgcagt ggcgctacaa gcttctgctc ttctctgcga cctttgcagg cacatggttc   240
ctctttggcg tggtgtggta tctggtagct gtggcacatg gggacctgct ggagctggac   300
cccccggcca accacacccc ctgtgtggta caggtgcaca cactcactgg agccttcctc   360
ttctcccttg aatcccaaac caccattggc tatggcttcc gctacatcag tgaggaatgt   420
ccactggcca ttgtgcttct tattgcccag ctggtgctca ccaccatcct ggaaatcttc   480
atcacaggta ccttcctggc gaagattgcc cggcccaaga gcgggctga gaccattcgt    540 ttcagccagc atgcagttgt ggcctcccac aatggcaagc cctgcctcat gatccgagtt   600
gccaatatgc gcaaaagcct cctcattggc tgccaggtga caggaaaact gcttcagacc   660 caccaaaacca aggaagggga gaacatccgg ctcaaccagg tcaatgtgac tttccaagta   720
gacacagcct ctgacagccc cttccttatt ctacccctta ccttctatca tgtggtagat   780
gagaccagtc ccttgaaaga tctccctctt cgcagtggtg agggtgactt tgagctggtg   840
ctgatcctaa gtgggacagt ggagtccacc agtgccacct gtcaggtgcg cacttcctac   900
ctgccagagg agatcctttg gggctacgag ttcacacctg ccatctcact gtcagccagt   960
ggtaaataca tagctgactt tagccttttt gaccaagttg tgaaagtggc ctctcctagt  1020
ggcctccgtg acagcactgt acgctacgga gaccctgaaa agctcaagtt ggaggagtca  1080
ttaagggagc aagctgagaa ggagggcagt gcccttagtg tgcgcatcag caatgtctga  1140

<210> SEQ ID NO 39
<211> LENGTH: 1128
<212> TYPE: DNA
<213> ORGANISM: Homo sapiens

<400> SEQUENCE: 39
atggatgcca ttcacatcgg catgtccagc accccctgg tgaagcacac tgctgggct     60 gggctcaagg ccaacagacc ccgcgtcatg tccaagagtg ggcacagcaa cgtgagaatt   120
gacaaagtgg atgcatata cctactctac ctgcaagacc tgtggaccac agttatcgac   180
atgaagtgga gatacaaact caccctgttc gctgccactt ttgtgatgac ctggttcctt   240
tttggagtca tctactatgc catcgcgttt attcatgggg acttagaacc cggtgagccc   300
atttcaaatc ataccccctg catcatgaaa gtggactctc tcactggggc gtttctcttt   360
tccctggaat cccagacaac cattggctat ggagtccgtt ccatcacaga ggaatgtcct   420
catgccatct tcctgttggt tgctcagttg gtcatcacga ccttgattga gatcttcatc   480
accggaacct tcctggccaa atcgccaga cccaaaaagc gggctgagac catcaagttc   540
agccactgtg cagtcatcac caagcagaat gggaagctgt gcttggtgat tcaggtagcc   600
aatatgagga gagcctcttt gattcagtgc cagctctctg gcaagctcct gcagacccac   660

| | |
|---|---|
| gtcaccaagg agggggagcg gattctcctc aaccaagcca ctgtcaaatt ccacgtggac | 720 |
| tcctcctctg agagcccctt cctcattctg cccatgacat tctaccatgt gctggatgag | 780 |
| acgagccccc tgagagacct cacaccccaa aacctaaagg agaaggagtt tgagcttgtg | 840 |
| gtcctcctca atgccactgt ggaatccacc agcgctgtct gccagagccg aacatcttat | 900 |
| atcccagagg aaatctactg gggttttgag tttgtgcctg tggtatctct ctccaaaaat | 960 |
| ggaaaatatg tggctgattt cagtcagttt gaacagattc ggaaaagccc agattgcaca | 1020 |
| ttttactgtg cagattctga gaaacagcaa ctcgaggaga agtacaggca ggaggatcag | 1080 |
| agggaaagag aactgaggac acttttatta caacagagca atgtctga | 1128 |

<210> SEQ ID NO 40
<211> LENGTH: 1257
<212> TYPE: DNA
<213> ORGANISM: Homo sapiens

<400> SEQUENCE: 40

| | |
|---|---|
| atgagctatt acggcagcag ctatcatatt atcaatgcgg acgcaaaata cccaggctac | 60 |
| ccgccagagc acattatagc tgagaagaga agagcaagaa gacgattact tcacaaagat | 120 |
| ggcagctgta atgtctactt caagcacatt tttggagaat ggggaagcta tgtggttgac | 180 |
| atcttcacca ctcttgtgga caccaagtgg cgccatatgt ttgtgatatt ttctttatct | 240 |
| tatattctct cgtggttgat atttggctct gtcttttggc tcatagcctt tcatcatggc | 300 |
| gatctattaa atgatccaga catcacacct tgtgttgaca acgtccattc tttcacaggg | 360 |
| gcctttttgt tctccctaga gacccaaacc accataggat atggttatcg ctgtgttact | 420 |
| gaagaatgtt ctgtggccgt gctcatggtg atcctccagt ccatcttaag ttgcatcata | 480 |
| aatacctttt tcattggagc tgccttggcc aaaatggcaa ctgctcgaaa gagagcccaa | 540 |
| accattcgtt tcagctactt tgcacttata ggtatgagag atgggaagct tgcctcatg | 600 |
| tggcgcattg tgattttcg gccaaaccac gtggtagaag aacagttag agcccaactt | 660 |
| ctccgctata cagaagacag tgaagggagg atgacgatgg catttaaaga cctcaaatta | 720 |
| gtcaacgacc aaatcatcct ggtcaccccg gtaactattg tccatgaaat tgaccatgag | 780 |
| agccctctgt atgcccttga ccgcaaagca gtagccaaag ataactttga gattttggtg | 840 |
| acatttatct atactggtga ttccactgga acatctcacc aatctagaag ctcctatgtt | 900 |
| ccccgagaaa ttctctgggg ccataggttt aatgatgtct tggaagttaa gaggaagtat | 960 |
| tacaaagtga actgcttaca gtttgaagga agtgtggaag tatatgcccc cttttgcagt | 1020 |
| gccaagcaat tggactggaa agaccagcag ctccacatag aaaaagcacc accagttcga | 1080 |
| gaatcctgca cgtcggacac caaggcgaga cgaaggtcat ttagtgcagt tgccattgtc | 1140 |
| agcagctgtg aaaaccctga ggagaccacc acttccgcca cacatgaata tagggaaaca | 1200 |
| ccttatcaga aagctctcct gactttaaac agaatctctg tagaatccca aatgtag | 1257 |

<210> SEQ ID NO 41
<211> LENGTH: 1275
<212> TYPE: DNA
<213> ORGANISM: Homo sapiens

<400> SEQUENCE: 41

| | |
|---|---|
| atgttggcca gaaagagtat catcccggag gagtatgtgc tggcgcgcat cgccgcagag | 60 |
| aacctgcgca gccgcgcat ccgagaccgc ctccccaaag cccgcttcat cgccaagagc | 120 |
| ggggcctgca acctggcgca taagaacatc cgtgagcaag gacgctttct acaggacatc | 180 |

| | |
|---|---|
| ttcaccacct tggtggacct gaaatggcgc cacacgctgg tcatctttac catgtccttc | 240 |
| ctctgcagct ggctgctctt cgctatcatg tggtggctgg tggcctttgc ccatggggac | 300 |
| atctatgctt acatggagaa aagtggaatg gagaaaagtg gtttggagtc cactgtgtgt | 360 |
| gtgactaatg tcaggtcttt cacttctgct tttctcttct ccattgaagt tcaagttacc | 420 |
| attgggtttg gagggaggat gatgacagag gaatgccctt tggccatcac ggttttgatt | 480 |
| ctccagaata ttgtgggttt gatcatcaat gcagtcatgt taggctgcat ttcatgaaa | 540 |
| acagctcagg ctcacagaag ggcagaaact ttgattttca gccgccatgc tgtgattgcc | 600 |
| gtccgaaatg gcaagctgtg cttcatgttc cgagtgggtg acctgaggaa agcatgatc | 660 |
| attagtgcct ctgtgcgcat ccaggtggtc aagaaaacaa ctacacctga ggggaggtg | 720 |
| gttcctattc accaactgga cattcctgtt gataacccaa tcgagagcaa taacattttt | 780 |
| ctggtggccc ctttgatcat ctgccacgtg attgacaagc gcagtcccct gtatgacatc | 840 |
| tcagcaactg acctggccaa ccaagacttg gaggtcatag ttattctgga aggagtggtt | 900 |
| gaaactactg gcatcaccac acaagcacga acctcctaca ttgctgagga gatccaatgg | 960 |
| ggccaccgct ttgtgtccat tgtgactgag gaagaaggag tgtattctgt ggattactcc | 1020 |
| aaatttggca acactgttaa agtagctgct ccacggtgca gtgcccgaga gctggatgag | 1080 |
| aaaccttcca tccttattca gaccctccaa aagagtgaac tgtctcatca aaattctctg | 1140 |
| aggaagcgca actccatgag aagaaacaat tccatgagga ggaacaattc tatccgaagg | 1200 |
| aacaattctt ccctcatggt accaaaggtg caatttatga ctccagaagg aaatcaaaac | 1260 |
| acatcggaat catga | 1275 |

<210> SEQ ID NO 42
<211> LENGTH: 1173
<212> TYPE: DNA
<213> ORGANISM: Homo sapiens

<400> SEQUENCE: 42

| | |
|---|---|
| atgctgtccc gcaagggcat catccccgag gaatacgtgc tgacacgcct ggcagaggac | 60 |
| cctgccaagc ccaggtaccg tgcccgccag cggagggccc gctttgtgtc caagaaaggc | 120 |
| aactgcaacg tggcccacaa gaacatccgg gagcagggcc gcttcctgca ggacgtgttc | 180 |
| accacgctgg tggacctcaa gtggccacac acattgctca tcttcaccat gtccttcctg | 240 |
| tgcagctggc tgctcttcgc catggcctgg tggctcatcg ccttcgccca cggtgacctg | 300 |
| gcccccagcg agggcactgc tgagccctgt gtcaccagca tccactcctt ctcgtctgcc | 360 |
| ttccttttct ccattgaggt ccaagtgact attggctttg ggggcgcat ggtgactgag | 420 |
| gagtgcccac tggccatcct gatcctcatc gtgcagaaca tcgtggggct catgatcaac | 480 |
| gccatcatgc ttggctgcat cttcatgaag actgcccaag cccaccgcag ggctgagacc | 540 |
| ctcatcttca gcaagcatgc ggtgatcgcc ctgcgcacg gccgcctctg cttcatgcta | 600 |
| cgtgtgggtg acctccgcaa gagcatgatc atcagcgcca ccatccacat gcaggtggta | 660 |
| cgcaagacca ccagccccga gggcgaggtg gtgcccctcc accaggtgga catccccatg | 720 |
| gagaacggcg tgggtggcaa cagcatcttc ctggtggccc cgctgatcat ctaccatgtc | 780 |
| attgatgcca acagcccact ctacgacctg gcacccagcg acctgcacca ccaccaggac | 840 |
| ctcgagatca tcgtcatcct ggaaggcgtg gtggaaccca gggcatcac cacccaggcc | 900 |
| cgcacctcct acctggccga tgagatcctg tggggccagc gctttgtgcc cattgtagct | 960 |

-continued

```
gaggaggacg gacgttactc tgtggactac tccaagtttg gcaacaccgt caaagtgccc    1020
acaccactct gcacggcccg ccagcttgat gaggaccaca gcctactgga agctctgacc    1080
ctcgcctcag cccgcgggcc cctgcgcaag cgcagcgtgc ccatggccaa ggccaagccc    1140
aagttcagca tctctccaga ttccctgtcc tga                                 1173
```

<210> SEQ ID NO 43
<211> LENGTH: 1083
<212> TYPE: DNA
<213> ORGANISM: Homo sapiens

<400> SEQUENCE: 43

```
atggacagca gtaattgcaa agttattgct cctctcctaa gtcaaagata ccggaggatg     60
gtcaccaagg atggccacag cacacttcaa atggatggcg ctcaaagagg tcttgcatat    120
cttcgagatg cttggggaat cctaatggac atgcgctggc gttggatgat gttggtcttt    180
tctgcttctt tgttgtcca ctggcttgtc tttgcagtgc tctggtatgt tctggctgag    240
atgaatggtg atctggaact agatcatgat gccccacctg aaaaccacac tatctgtgtc    300
aagtatatca ccagtttcac agctgcattc tccttctccc tggagacaca actcacaatt    360
ggttatggta ccatgttccc cagtggtgac tgtccaagtg caatcgcctt acttgccata    420
caaatgctcc taggcctcat gctagaggct tttatcacag gtgcttttgt ggcgaagatt    480
gcccggccaa aaatcgagc tttttcaatt cgctttactg acacagcagt agtagctcac    540
atggatggca aacctaatct tatcttccaa gtggccaaca cccgacctag ccctctaacc    600
agtgtccggg tctcagctgt actctatcag gaaagagaaa atggcaaact ctaccagacc    660
agtgtggatt ccaccttga tggcatcagt tctgacgaat gtccattctt catctttcca    720
ctaacgtact atcactccat taccatca agtcctctgg ctactctgct ccagcatgaa    780
aatccttctc actttgaatt agttgtattc ctttcagcaa tgcaggaggg cactggagaa    840
atatgccaaa ggaggacatc ctacctaccg tctgaaatca tgttacatca ctgttttgca    900
tctctgttga cccgaggttc caaaggtgaa atcaaatca agatggagaa ttttgacaag    960
actgtccctg aatttccaac tcctctggtt tctaaaagcc caaacaggac tgacctggat   1020
atccacatca atggacaaag cattgacaat tttcagatct ctgaaacagg actgacagaa   1080
taa                                                                1083
```

<210> SEQ ID NO 44
<211> LENGTH: 1284
<212> TYPE: DNA
<213> ORGANISM: Gallus gallus

<400> SEQUENCE: 44

```
atgggcagcg tgcgaaccaa ccgctacagc atcgtgtctt cggaagagga cggcatgaag     60
ctggcaacca tggccgttgc caatggcttt gggaatggaa aaagtaaggt acacaccagg    120
cagcagtgca ggagccgctt tgtcaaaaaa gatggccact gcaacgtcca gtttattaat    180
gtgggtgaga agggacagcg atacctcgca gacatcttca ccacttgcgt ggacatccgc    240
tggaggtgga tgctggttat cttctgcctg acattcatcc tctcctggct tttcttggc    300
tgtgtgttt ggttgattgc gctgttgcac ggggatctgg agaaccaaga aaataacaaa    360
ccgtgtgtct cgcaagtgag cagcttcact gcagcctttc tgttctccat tgagacccag    420
accacgatcg gctatggctt caggtgcgtc acagacgagt gccccattgc tgttttcatg    480
gtggttttcc agtctatagt aggctgcatc attgacgcct tcatcattgg tgccgtcatg    540
```

```
gcaaagatgg ctaagccaaa aaagagaaac gaaactcttg tcttcagcca caatgccgtg    600
gtggccatga gagatgggaa actgtgcctg atgtggcgtg tcggaaacct gaggaaaagc    660
cacttggttg aggcacacgt gcgagcacag ctcctcaagt ccaggatcac gtcagaaggg    720
gagtacatcc ctttggatga aatagacatc aatgtagggt ttgacagcgg gatagaccgc    780
atattcctgg tctccccaat tacaatagta cacgaaatag atgaagatag tcctttgtat    840
gacttgagca aacaagacat ggacaatgct gactttgaaa ttgtagtcat tttagagggc    900
atggtggaag ccactgccat gactacccag tgccgcagct catatctggc aaatgaaatc    960
ctctggggcc accgctatga gcccgtactc tttgaagaaa aaaactacta caaagtggac   1020
tattcaaggt tccacaaaac atacgaagtg cccaacacac ccatctgcag tgccagagac   1080
ttagcagaaa agaaatacat tctctcgaac gcaaactcct tttgctacga gaacgaagtg   1140
gccctcacca gcaaggagga ggacgagatc gacacggggg tgcccgagag cacaagcaca   1200
gacacccacc ccgacatgga ccaccacaac caggcaggag tgcccctaga gccacggccg   1260
ctgcggcgtg agtcggaaat atga                                          1284
```

```

<210> SEQ ID NO 45
<211> LENGTH: 1290
<212> TYPE: DNA
<213> ORGANISM: Gallus gallus

<400> SEQUENCE: 45
atgactgcag gcagggtcaa cccttacagc atagtgtcct ccgaggaaga cggactgagg     60
ttgaccacca tgccagggat taacggcttt ggcaatggga aaatccacac caggaggaaa    120
tgcaggaaca ggtttgtaaa gaagaacggt cagtgcaatg tggagttcac caacatggat    180
gacaagccac agaggtacat tgcagacatg ttcaccacgt gcgttgacat ccgttggagg    240
tatatgctct tgctcttctc cctggcattt ctggtatcct ggttattgtt tgggctgatt    300
ttctggctaa ttgcactcat tcatggagat ctagaaaacc caggtggaga tgataccttc    360
aagccttgcg ttctgcaggt caatggcttt gtggctgctt ttctgttctc catcgagacc    420
caaacgacta ttggttatgg cttccgctgt gtgacagagg agtgcccgct cgcagtcttc    480
atggtggtgg ttcagtccat cgtggggtgt ataatcgact ctttcatgat tggtgcaata    540
atggcaaaga tggccaggcc caaaaaaagg gcccagacat tgcttttcag ccataatgca    600
gtagtggcaa tgagagatgg aaaactctgc ctgatgtgga gagttgggaa tctccggaaa    660
agccacatag tagaagccca cgtacgagct caattaatta agcccagaat cacagaagaa    720
ggggagtaca tcccactcga ccaaatagac atcgacgtgg ggtttgacaa aggcttggac    780
cgaatcttct tggtgtcccc cattaccatt ctccatgaga tcaacgaaga cagcccgctg    840
ttcgggatca gccgccagga cttggagacg gatgactttg agattgtggt catcctcgaa    900
ggcatggtag aagccaccgc gatgacgaca caagctcgga gctcctacct ggccagcgag    960
atcctgtggg gccaccgctt cgagcccgtc ttgttcgagg agaaaaacca gtacaaagta   1020
gactattccc acttccacaa aacatacgag gtcccgtcca caccccgctg cagcgccaag   1080
gacttggtgg agaacaaatt cctgctgccc agcaccaact ccttctgcta cgagaatgag   1140
ctggccttca tgagccgcga tgaggatgag gaggatgatg acagcagggg tttggacgac   1200
ctgagcccag acaacaggca cgagttcgac cggcttcagg caacgatagc gttggatcag   1260
aggtcatacc ggagggagtc agaaatatga                                    1290
```

<210> SEQ ID NO 46
<211> LENGTH: 22
<212> TYPE: PRT
<213> ORGANISM: Homo sapiens

<400> SEQUENCE: 46

His Lys Asp Leu Pro Glu Phe His Pro Ser Ala Asn His Thr Pro Cys
1               5                   10                  15

Val Glu Asn Ile Asn Gly
            20

<210> SEQ ID NO 47
<211> LENGTH: 22
<212> TYPE: PRT
<213> ORGANISM: Homo sapiens

<400> SEQUENCE: 47

His Gly Asp Leu Leu Glu Leu Asp Pro Pro Ala Asn His Thr Pro Cys
1               5                   10                  15

Val Val Gln Val His Thr
            20

<210> SEQ ID NO 48
<211> LENGTH: 19
<212> TYPE: PRT
<213> ORGANISM: Homo sapiens

<400> SEQUENCE: 48

His Gly Asp Leu Asp Ala Ser Lys Glu Gly Lys Ala Cys Val Ser Glu
1               5                   10                  15

Val Asn Ser

<210> SEQ ID NO 49
<211> LENGTH: 21
<212> TYPE: PRT
<213> ORGANISM: Homo sapiens

<400> SEQUENCE: 49

His Gly Asp Leu Glu Pro Ala Glu Gly Arg Gly Arg Thr Pro Cys Val
1               5                   10                  15

Met Gln Val His Gly
            20

<210> SEQ ID NO 50
<211> LENGTH: 37
<212> TYPE: PRT
<213> ORGANISM: Homo sapiens

<400> SEQUENCE: 50

His Gly Asp Leu Glu Ala Ser Pro Gly Val Pro Ala Ala Gly Gly Pro
1               5                   10                  15

Ala Ala Gly Gly Gly Gly Ala Ala Pro Val Ala Pro Lys Pro Cys Ile
            20                  25                  30

Met His Val Asn Gly
            35

<210> SEQ ID NO 51
<211> LENGTH: 19
<212> TYPE: PRT
<213> ORGANISM: Homo sapiens

<400> SEQUENCE: 51

His Gly Asp Leu Ala Ala Pro Pro Pro Ala Pro Cys Phe Ser His
1               5                   10                  15

Val Ala Ser

<210> SEQ ID NO 52
<211> LENGTH: 21
<212> TYPE: PRT
<213> ORGANISM: Homo sapiens

<400> SEQUENCE: 52

Arg Gly Asp Leu Asn Lys Ala His Val Gly Asn Tyr Thr Pro Cys Val
1               5                   10                  15

Ala Asn Val Tyr Asn
            20

<210> SEQ ID NO 53
<211> LENGTH: 21
<212> TYPE: PRT
<213> ORGANISM: Homo sapiens

<400> SEQUENCE: 53

Arg Gly Asp Leu Asp His Val Gly Asp Gln Glu Trp Ile Pro Cys Val
1               5                   10                  15

Glu Asn Leu Ser Gly
            20

<210> SEQ ID NO 54
<211> LENGTH: 29
<212> TYPE: PRT
<213> ORGANISM: Homo sapiens

<400> SEQUENCE: 54

His Gly Asp Ile Tyr Ala Tyr Met Glu Lys Ser Gly Met Glu Lys Ser
1               5                   10                  15

Gly Leu Glu Ser Thr Val Cys Val Thr Asn Val Arg Ser
            20                  25

<210> SEQ ID NO 55
<211> LENGTH: 20
<212> TYPE: PRT
<213> ORGANISM: Homo sapiens

<400> SEQUENCE: 55

His Gly Asp Leu Ala Pro Ser Glu Gly Thr Ala Glu Pro Cys Val Thr
1               5                   10                  15

Ser Ile His Ser
            20

<210> SEQ ID NO 56
<211> LENGTH: 24
<212> TYPE: PRT
<213> ORGANISM: Homo sapiens

<400> SEQUENCE: 56

Asn Gly Asp Leu Glu Leu Asp His Asp Ala Pro Pro Glu Asn His Thr
1               5                   10                  15

Ile Cys Val Lys Tyr Ile Thr Ser
            20

<210> SEQ ID NO 57
<211> LENGTH: 19

```
<212> TYPE: PRT
<213> ORGANISM: Gallus gallus

<400> SEQUENCE: 57

His Gly Asp Leu Glu Asn Gln Glu Asn Asn Lys Pro Cys Val Ser Gln
1               5                   10                  15

Val Ser Ser

<210> SEQ ID NO 58
<211> LENGTH: 22
<212> TYPE: PRT
<213> ORGANISM: Gallus gallus

<400> SEQUENCE: 58

His Gly Asp Leu Glu Asn Pro Gly Gly Asp Asp Thr Phe Lys Pro Cys
1               5                   10                  15

Val Leu Gln Val Asn Gly
            20

<210> SEQ ID NO 59
<211> LENGTH: 309
<212> TYPE: PRT
<213> ORGANISM: Unknown
<220> FEATURE:
<223> OTHER INFORMATION: Description of Artificial Sequence: Note =
      Synthetic Construct

<400> SEQUENCE: 59

Ser Pro Ala Arg Lys Pro Pro Arg Gly Gly Arg Arg Ile Trp Ser Gly
1               5                   10                  15

Thr Arg Glu Val Ile Ala Tyr Gly Met Pro Ala Ser Val Trp Arg Asp
                20                  25                  30

Leu Tyr Tyr Trp Ala Leu Lys Val Ser Trp Pro Val Phe Phe Ala Ser
            35                  40                  45

Leu Ala Ala Leu Phe Val Val Asn Asn Thr Leu Phe Ala Leu Leu Tyr
        50                  55                  60

Gln Leu Gly Asp Ala Pro Ile Ala Asn Gln Ser Pro Pro Gly Phe Val
65                  70                  75                  80

Gly Ala Phe Phe Phe Ser Val Glu Thr Leu Ala Thr Val Gly Tyr Gly
                85                  90                  95

Asp Met His Pro Gln Thr Val Tyr Ala His Ala Ile Ala Thr Leu Glu
            100                 105                 110

Ile Phe Val Gly Met Ser Gly Ile Ala Leu Ser Thr Gly Leu Val Phe
        115                 120                 125

Ala Arg Phe Ala Arg Pro Arg Ala Lys Ile Met Phe Ala Arg His Ala
130                 135                 140

Ile Val Arg Pro Phe Asn Gly Arg Met Thr Leu Met Val Arg Ala Ala
145                 150                 155                 160

Asn Ala Arg Gln Asn Val Ile Ala Glu Ala Arg Ala Lys Met Arg Leu
                165                 170                 175

Met Arg Arg Glu His Ser Ser Glu Gly Tyr Ser Leu Met Lys Ile His
            180                 185                 190

Asp Leu Lys Leu Val Arg Asn Glu His Pro Ile Phe Leu Leu Gly Trp
        195                 200                 205

Asn Met Met His Val Ile Asp Glu Ser Ser Pro Leu Phe Gly Glu Thr
    210                 215                 220

Pro Glu Ser Leu Ala Glu Gly Arg Ala Met Leu Leu Val Met Ile Glu
225                 230                 235                 240
```

```
Gly Ser Asp Glu Thr Thr Ala Gln Val Met Gln Ala Arg His Ala Trp
            245                 250                 255

Glu His Asp Asp Ile Arg Trp His His Arg Tyr Val Asp Leu Met Ser
            260                 265                 270

Asp Val Asp Gly Met Thr His Ile Asp Tyr Thr Arg Phe Asn Asp Thr
            275                 280                 285

Glu Pro Val Glu Pro Pro Gly Ala Ala Pro Asp Ala Gln Ala Phe Ala
            290                 295                 300

Ala Lys Pro Gly Glu
305

<210> SEQ ID NO 60
<211> LENGTH: 124
<212> TYPE: PRT
<213> ORGANISM: Unknown
<220> FEATURE:
<223> OTHER INFORMATION: Description of Artificial Sequence: Note =
      Synthetic Construct

<400> SEQUENCE: 60

Met Ala Pro Met Leu Ser Gly Leu Leu Ala Arg Leu Val Lys Leu Leu
1               5                   10                  15

Leu Gly Arg His Gly Ser Ala Leu His Trp Arg Ala Ala Gly Ala Ala
            20                  25                  30

Thr Val Leu Leu Val Ile Val Leu Leu Ala Gly Ser Tyr Leu Ala Val
            35                  40                  45

Leu Ala Glu Arg Gly Ala Pro Gly Ala Gln Leu Ile Thr Tyr Pro Arg
        50                  55                  60

Ala Leu Trp Trp Ser Val Glu Thr Ala Thr Thr Val Gly Tyr Gly Asp
65                  70                  75                  80

Leu Tyr Pro Val Thr Leu Trp Gly Arg Cys Val Ala Val Val Val Met
                85                  90                  95

Val Ala Gly Ile Thr Ser Phe Gly Leu Val Thr Ala Ala Leu Ala Thr
            100                 105                 110

Trp Phe Val Gly Arg Glu Gln Glu Arg Arg Gly His
            115                 120

<210> SEQ ID NO 61
<211> LENGTH: 100
<212> TYPE: PRT
<213> ORGANISM: Unknown
<220> FEATURE:
<223> OTHER INFORMATION: Description of Artificial Sequence: Note =
      Synthetic Contruct

<400> SEQUENCE: 61

Met Arg Glu Leu Gly Leu Leu Ile Phe Phe Leu Phe Ile Gly Val Ile
1               5                   10                  15

Leu Phe Ser Ser Ala Val Tyr Phe Ala Glu Ala Asp Glu Arg Asp Ser
            20                  25                  30

Gln Phe Pro Ser Ile Pro Asp Ala Phe Trp Trp Ala Val Val Ser Met
            35                  40                  45

Thr Thr Val Gly Tyr Gly Asp Met Val Pro Thr Thr Ile Gly Gly Lys
        50                  55                  60

Ile Val Gly Ser Leu Cys Ala Ile Ala Gly Val Leu Thr Ile Ala Leu
65                  70                  75                  80
```

-continued

```
Pro Val Pro Val Ile Val Ser Asn Phe Asn Tyr Phe Tyr His Arg Glu
            85                  90                  95
Thr Glu Gly Glu
            100
```